United States Patent
Momose et al.

(10) Patent No.: US 7,396,848 B1
(45) Date of Patent: *Jul. 8, 2008

(54) NEUROTROPHIN PRODUCTION/SECRETION PROMOTING AGENT

(75) Inventors: Yu Momose, Takarazuka (JP); Katsuhito Murase, Dallas, TX (US)

(73) Assignee: Takeda Pharmaceutical Company Limited, Osaka (JP)

( * ) Notice: Subject to any disclaimer, the term of this patent is extended or adjusted under 35 U.S.C. 154(b) by 666 days.

This patent is subject to a terminal disclaimer.

(21) Appl. No.: 10/616,769

(22) Filed: Jul. 10, 2003

Related U.S. Application Data

(62) Division of application No. 09/868,304, filed as application No. PCT/JP00/05681 on Aug. 24, 2000, now Pat. No. 6,605,629.

(51) Int. Cl.
*A61K 31/42* (2006.01)
*A61K 31/415* (2006.01)

(52) U.S. Cl. ..................... 514/374; 514/396

(58) Field of Classification Search .......... 514/374, 514/396
See application file for complete search history.

(56) References Cited

U.S. PATENT DOCUMENTS

| 3,575,991 A | 4/1971 | Kim .................. 260/294.8 |
| 6,605,629 B1 * | 8/2003 | Momose et al. ......... 514/374 |

FOREIGN PATENT DOCUMENTS

| EP | 0 033 617 | 8/1981 |
| EP | 0 555 149 | 8/1993 |
| EP | 0 906 755 | 4/1999 |
| GB | 1 574 583 | 9/1980 |
| JP | 62-178590 | 8/1987 |
| JP | 62-234018 | 10/1987 |

(Continued)

OTHER PUBLICATIONS

Pillay et al. "Molecular mechanisms, Emerging Etiological insights and model to test potential therapeutical interventions in Alzheimer's disease," Current Alzheimer Research, 2004, vol. 1, No. 4, pp. 295-306.*

(Continued)

*Primary Examiner*—Shengjun Wang
(74) *Attorney, Agent, or Firm*—David G. Conlin; Gregory B. Butler; Edwards Angell Palmer & Dodge LLP

(57) ABSTRACT

A neurotrophin production/secretion promoting agent which comprises an azole derivative of the formula:

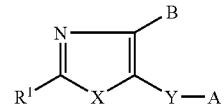

wherein $R^1$ represents a halogen atom, a heterocyclic group which may optionally be substituted, a hydroxy group which may optionally be substituted, a thiol group which may optionally be substituted, or an amino group which may optionally be substituted; A represents an acyl group which may optionally be substituted, a heterocyclic group which may optionally be substituted, a hydroxy group which may optionally be substituted, or a carboxyl group which may optionally be esterified or amidated; B represents an aromatic group which may optionally be substituted; X represents oxygen atom, sulfur atom, or nitrogen atom which may optionally be substituted; and Y represents a divalent hydrocarbon group or heterocyclic group, or a salt thereof; which is useful as an agent for preventing or treating neuropathy.

11 Claims, 1 Drawing Sheet

FOREIGN PATENT DOCUMENTS

| | | |
|---|---|---|
| JP | 7-242663 | 9/1995 |
| WO | WO-95/01979 | 1/1995 |
| WO | WO 97 36882 | 10/1997 |
| WO | WO 99/16460 * | 4/1999 |
| WO | WO 00 01679 | 1/2000 |
| WO | WO 01 19806 | 3/2001 |

OTHER PUBLICATIONS

Gieldanowski, Jerzy, et al. "Pharmacological Activity in the Group of New Substituted Thiazoloacetic and Thiazinocarboxyl Acid Derivatives" Archivum Immunologiae et Thereapiae Experiementalis 26:921-929 (1978).

Brown, Kevan, et al. "Nonsteroidal Antiinflammatory Agents. 1. 2,4-Diphenylthiazole-5-acetic Acid and Related Compounds" Journal of Medicinal Chemistry 17(11): 1177-1181(1974).

Sharma, Pawan K., et al. "Synthesis and Antiinflammatory Activity of Some 1,4-Dihydro-3-methyl-1-(2-thiazolyl)pyrazolo[4,3-c][1,2]benzothiazine 5,5-Diozides" Bull. Chem. Soc. Jpn. 66(12): 3843-3846 (1993).

Sawhney, S.N., et al. "Synthesis & Antiinflammatory Activity of Some 5-Thiazoleacetic Acids" Indian Journal of Chemistry 22B: 1044-1049(1983).

Jakobiec, Tadeusz, et al. "Studies on the Derivatives of 2-Amino-4-P-Chlorophenylthiazole-5-Acetic Acid" Archivum Immunologiae et Thereapiae Experiementalis, 27: 777-794 (1979).

Hirai, Kentaro, et al. "Synthesis of 2-Disubstituted-amino-4-arylthiazol-5-ylalkanoic Acids" Chem. Pharm. Bull. 25(9):2292-2299(1977).

Sharma P K et al. "Potent antiinflammatory 3-thiazole-4(5)-acetic acids of 1,2-benzisothiazole" Biorganic & Medicinal Chem. Let., Gb, Oxford (1997) 7(18), 2427-2430.

Kawakita, T et al., "Preparation of benzoxazine derivatives as phospholipase A2 and interleukin 1 inhibitors" CHEMABS Database accession No. 124:117333—JP07 242663 A, Sep. 19, 1995.

Gieldanowski, Jerzy et al: "Pharmacological activity in the group of new substituted thiazoloacetic and thiazinocardboxyl acid derivatives" CHEMABS Database accession No. 91:68296,—Arch. Immunol. Ther. Exp. (1978) 26(1-6), 921-9.

Hirai, Kentaro et al., "2-Dialkylamino-4aryl-5-thiazoleacetic acids" CHEMABS Database accession No. 86:89798,—JP 51 088964 A, Aug. 4, 1976.

Brown, Kevan, et al. "Nonsteroidal antiinflammatory agents.1. 2,4-Diphenylthiazole-5-acetic acid and related compounds" CHEMABS Database accession No. 82:38473,—J. Med. Chem. (1974) 17(11), 1177-1181.

Sharma, Pawan K. et al, "Synthesis and antiinflammatory activity of some 1,4-dihydro-3-methyl-1-(2-thiazolyl)pyrazolo'4,3-c(1,2) benzothiazine 5,5-dioxides" CHEMABS Database accession No. 121:9292,—Chem. Soc. JPN (1993) 66(12), 3842-6.

Sawhney, S.N. et al., "Synthesis and antiinflammatory activity of some 5-thiazoleacetic acids" CHEMABS Database accession No. 100:139014,—Indiana J. Chem., Sect. B (1983) 22B(10), 1044-9.

Stankiewicz, Julian et al., "Studies on derivatives of 2-amino-4-(p-chlorophenyl)thiazole-5-acetic acid" CHEMABS Database accession No. 98:53756,—Arch. Immunol. ther. Exp. (1981) 29(6), 827-33.

Jacobiec, Tadeusz et al., "Studies on the derivatives of 2-amino-4-p-chlorophenylthiazole-5-acetic acid" CHEMABS Database accession No. 93:36820,—Arch Immunol. Ther. Exp. (1979) 27(6), 777-94.

Hirai, Kentaro et al., "Studies on heterocyclic cation systems. XI. Synthesis of 2-disubstituted-amino-4-arylthiazol-5-ylal kanoic acids" CHEMABS database accession No. 88:50706,—Chem. Pharm. Bull. (1977) 25(9), 2292-9.

Kondo Sei,—JP 08 175992 A, Jul. 9, 1996, abstract in Patent Abstracts of Japn. vol. 1996, No. 11, Nov. 29, 1996.

\* cited by examiner

NEUROTROPHIN PRODUCTION/SECRETION PROMOTING AGENT

This application is a divisional of U.S. patent application Ser. No. 09/868,304, now U.S. Pat. No. 6,605,629, issued Aug. 12, 2003, which was the National Phase filing of International Patent Application No. PCT/JP00/05681, filed Aug. 24, 2000.

TECHNICAL FIELD

The present invention relates to a neurotrophin production/secretion promoting agent which comprises an azole derivative or a salt thereof and is useful in the treatment or prevention of neuropathy and so forth, and to novel thiazole derivatives and oxazole derivatives having neurotrophin production/secretion promoting activity.

BACKGROUND ART

Neurotrophin is a generic term denoting nerve growth factor (NGF) gene families, meaning proteins which play an important role in the differentiation and functional homeostasis of central and peripheral nerve cells, synapse formation, and regeneration or repair of injured nerve cells. In addition to NGF, so far discovered in mammals are brain-derived neurotrophic factor (BDNF), neurotrophin-3 (NT-3) and neurotrophin-4/5 (NT-4/5) (while neurotrophin-6 (NT-6) has been discovered in fish, it is not known whether this exists in mammals as well). While these are similar in structure and in physiological activity, it is known that they differ in specificity to responding neurons. On the other hand, TrkA, TrkB and TrkC, which are trk family gene products, have been identified as neurotrophin receptors. NGF has high affinity for TrkA, BDNF and NT-4/5 have high affinity for TrkB, and NT-3 has high affinity for TrkC. The complicated actions of neurotrophins on the nervous system are considered to result from the functions, distributions and expression regulating mechanisms involved of neurotrophins and their receptors.

The possibility of clinical application of neurotrophins has been suggested based on the diversity of their actions on the nervous system. In fact, in animal experiments, it has been revealed that NGF, upon intracranial administration, improves the memory and ability to learn and prevents death of neurons due to brain ischemia (Brain Res., vol. 293, p. 305 (1985); Science, vol. 235, p. 214 (1986); Proc. Natl. Acad. Sci. USA, vol. 83, p. 9231 (1986); and etc.). Further, it was confirmed by Lans Olsson et al. that direct injection of NGF into the brain of patients with Alzheimer's disease resulted in amelioration of symptoms of dementia (1991 Symposium on Alzheimer's Disease). Further, patients with diabetic neuropathy show a decreased serum NGF level and, in animal experiments, the pathology of diabetic neuropathy is improved by administration of NGF (Acta Neurol. Scand., vol. 81, p. 402 (1990); Brain Res., vol. 634, p. 7 (1994)) and, based on these and other findings, NGF is considered to effectively act on peripheral nervous system diseases as well as the central nervous system diseases. On the other hand, it is known that when the rat sciatic nerve is injured, Schwann cells transiently synthesize and secrete NGF and thereafter synthesize and secrete BDNF over a long period (J. Cell Biol., vol. 119, p. 45 (1992)). It is further known that BDNF, when intramuscularly administered to wobbler mice genetically developing motor nerve degeneration, prevents the nerve degeneration (Neurology, 50 (4S) A 246 (1998)), that it shows a protective effect on the motor nerve degeneration and nerve cells death in rats (40th Meeting of the Japanese Neurochemical Society, 238 (1997); 15th Meeting of the International Society for Neurochemistry, S85 (1995)) and that it shows a protective effect on motor functions and sensory nerve cells in an acrylamide neuropathy model (60th Meeting of the Japanese Pharmacological Society, P-532, 1996).

In view of these findings, NGF is currently under clinical investigation as a therapeutic agent for peripheral neuropathy caused by cancer chemotherapy or diabetes mellitus (Genentech), and BDNF as a therapeutic agent for nerve degeneration diseases or amyotrophic lateral sclerosis (ALS) (Sumitomo Pharmaceutical, Regeneron).

However, these neurotrophins each is a macromolecular protein having a molecular weight of 10,000 or more and it is known that applying these neurotrophins as therapeutic agents can lead to problems, such as limited methods of administration and safety problems. Therefore, searching for low molecular compounds capable of promoting the production/secretion of neurotrophins in a specific tissue is of great significance in developing prophylactic/therapeutic agents for diseases of the central or peripheral nervous system. Low molecular compounds hitherto known to have NGF production/secretion promoting activity include catechol derivatives (Furukawa, Y., J. Biol. Chem., vol. 261, p. 6039 (1986); JP Kokai S63-83020; JP Kokai S63-156751; JP Kokai H02-53767; JP Kokai H02-104568; JP Kokai H02-149561; JP Kokai H03-99046; JP Kokai H03-83921; JP Kokai H03-86853; JP Kokai H05-32646), quinone derivatives (JP Kokai H03-81218; JP Kokai H04-330010; JP Kokai H07-285912), glutamic acid derivatives (JP Kokai H07-228561), unsaturated fatty acid derivatives (JP Kokai H08-143454), eudesmane derivatives (JP Kokai H08-73395), condensed-ring oxazole derivatives (JP Kokai H08-175992), carbazole derivatives (JP Kokai H08-169879), indole derivatives (JP Kokai H07-118152; JP Kokai H08-239362), and natural product-derived terpene derivatives (JP Kokai H07-149633; JP Kokai H08-319289). However, their activities are not satisfactory enough, and more potent compounds are desired. It is also known that leteprinim (NeuroTherapeutics, USA), which is a purine derivative, promotes intracranial neurotrophin production in an animal model.

Meanwhile, some of the compounds of the formula (I) or salts thereof described hereafter, wherein X is O, which are active ingredients in the present invention, are disclosed in JP Kokai H09-323983 (WO97/36882), hence already known. However, the neurotrophin production/secretion promoting activity of these known compounds is so far unknown.

It is an object of the present invention to provide neurotrophin production/secretion promoting agents which are useful in the prevention and treatment of diabetic neuropathy, other kinds of peripheral neuropathy resulting from cancer chemotherapy, diabetic cardiomyopathy, nerve degeneration diseases, amyotrophic lateral sclerosis, multiple sclerosis, cerebral ischemic diseases, Alzheimer's disease, Parkinson's disease, Huntington's chorea, depression, inflammatory bowel disease and so forth.

DISCLOSURE OF INVENTION

The present inventors found that a specific class of azole derivatives or salts thereof have excellent neurotrophin production/secretion promoting activity and, as a result of further investigations, have now completed the present invention.

Namely, the present invention relates to:

(1) a neurotrophin production/secretion promoting agent which comprises an azole derivative of the formula:

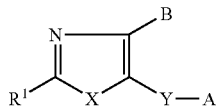

wherein R¹ represents a halogen atom, a heterocyclic group which may optionally be substituted, a hydroxy group which may optionally be substituted, a thiol group which may optionally be substituted, or an amino group which may optionally be substituted; A represents an acyl group which may optionally be substituted, a heterocyclic group which may optionally be substituted, a hydroxy group which may optionally be substituted, or a carboxyl group which may optionally be esterified or amidated; B represents an aromatic group which may optionally be substituted; X represents oxygen atom, sulfur atom, or nitrogen atom which may optionally be substituted; and Y represents a divalent hydrocarbon group or heterocyclic group, or a salt thereof;

(2) a neurotrophin production/secretion promoting agent which comprises a prodrug of an azole derivative or a salt thereof as defined in the above (1);

(3) an agent according to the above (1), wherein R¹ is a nitrogen-containing heterocyclic group which may optionally be substituted;

(4) an agent according to the above (1), wherein R¹ is an aromatic heterocyclic group which may optionally be substituted;

(5) an agent according to the above (1), wherein R¹ is a nitrogen-containing 5-membered aromatic heterocyclic group which may optionally be substituted;

(6) an agent according to the above (1), wherein R¹ is an imidazolyl group which may optionally be substituted;

(7) an agent according to the above (1), wherein A is a heterocyclic group which may optionally be substituted, or a hydroxy group which may optionally be substituted;

(8) an agent according to the above (1), wherein A is an aryloxy group which may optionally be substituted;

(9) an agent according to the above (1), wherein A is a phenoxy group substituted with an alkyl group which may optionally be substituted;

(10) an agent according to the above (1), wherein B is a phenyl group which may optionally be substituted;

(11) an agent according to the above (1), wherein Y is a divalent aliphatic hydrocarbon group;

(12) an agent according to the above (1), wherein X is —O—;

(13) an agent according to the above (1), wherein X is —S—;

(14) an agent according to the above (1), wherein X is —NR⁴— wherein R⁴ represents a hydrogen atom, a hydrocarbon group which may optionally be substituted, an acyl group which may optionally be substituted, or a heterocyclic group which may optionally be substituted;

(15) an agent according to the above (1), wherein the azole derivative is 4-(4-chlorophenyl)-2-(2-methyl-1-imidazolyl)-5-oxazolepropanol, 4-(4-chlorophenyl)-2-(2-methyl-1-imidazolyl)-5-oxazolebutanol, 4-(4-chlorophenyl)-5-[3-(1-imidazolyl)propyl]-2-(2-methyl-1-imidazolyl)oxazole, 4-(4-chlorophenyl)-2-(2-methyl-1-imidazolyl)-5-oxazolepentanol, 4-(4-chlorophenyl)-5-[4-(1-imidazolyl)butyl]-2-(2-methyl-1-imidazolyl)oxazole, 3-[3-[4-(4-chlorophenyl)-2-(2-methyl-1-imidazolyl)-5-oxazolyl]propyl]-1-methyl-2,4-imidazolidinedione, 4-(4-chlorophenyl)-5-[3-(2-methoxyphenoxy)propyl]-2-(2-methyl-1-imidazolyl)oxazole, 4-(4-chlorophenyl)-5-[3-(3-methoxyphenoxy)propyl]-2-(2-methyl-1-imidazolyl)oxazole, 4-(4-chlorophenyl)-5-[3-(4-methoxyphenoxy)propyl]-2-(2-methyl-1-imidazolyl)oxazole, or 4-(4-chlorophenyl)-2-(2-methyl-1-imidazolyl)-5-[3-(2-methylphenoxy)propyl]oxazole;

(16) an agent according to the above (1) which is a prophylactic/therapeutic agent for neuropathy;

(17) an agent according to the above (1) which is a prophylactic/therapeutic agent for peripheral neuropathy;

(18) a thiazole derivative of the formula:

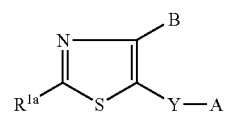

wherein R¹ᵃ represents a heterocyclic group which may optionally be substituted; A represents an acyl group which may optionally be substituted, a heterocyclic group which may optionally be substituted, a hydroxy group which may optionally be substituted, or a carboxyl group which may optionally be esterified or amidated; B represents an aromatic group which may optionally be substituted; and Y represents a divalent hydrocarbon group or heterocyclic group, or a salt thereof;

(19) a prodrug of a thiazole derivative or a salt thereof as defined in the above (18);

(20) a compound according to the above (18), wherein R¹ᵃ is a nitrogen-containing 5-membered aromatic heterocyclic group which may optionally be substituted;

(21) a compound according to the above (18), wherein R¹ᵃ is an imidazolyl group which may optionally be substituted;

(22) a compound according to the above (18), wherein A is an aryloxy group which may optionally be substituted;

(23) a compound according to the above (18), wherein B is a phenyl group which may optionally be substituted;

(24) a compound according to the above (18), wherein Y is a divalent aliphatic hydrocarbon group;

(25) a pharmaceutical composition which comprises a thiazole derivative or a salt thereof as defined in the above (18);

(26) a composition according to the above (25) which is a neurotrophin production/secretion promoting agent;

(27) a composition according to the above (25) which is a prophylactic/therapeutic agent for neuropathy;

(28) a composition according to the above (25) which is a prophylactic/therapeutic agent for peripheral neuropathy;

(29) an oxazole derivative of the formula

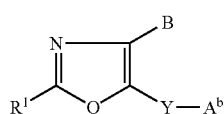
(Ib)

wherein R¹ represents a halogen atom, a heterocyclic group which may optionally be substituted, a hydroxy group which may optionally be substituted, a thiol group which may optionally be substituted, or an amino group which may optionally be substituted; $A^b$ represents an aryloxy group which is substituted by an alkyl group and may further be substituted; B represents an aromatic group which may optionally be substituted; and Y represents a divalent hydrocarbon group or heterocyclic group, or a salt thereof;

(30) a compound according to the above (29), wherein $A^b$ is an aryloxy group which is substituted by an alkyl group;

(31) a prodrug of an oxazole derivative or a salt thereof as defined in the above (29);

(32) a compound according to the above (29), wherein R¹ is a nitrogen-containing 5-membered aromatic heterocyclic group which may optionally be substituted;

(33) a compound according to the above (29), wherein R¹ is an imidazolyl group which may optionally be substituted;

(34) a compound according to the above (33), wherein R¹ is an imidazolyl group which may optionally be substituted by a $C_{1-10}$ alkyl;

(35) a compound according to the above (29), wherein B is a phenyl group which may optionally be substituted;

(36) a compound according to the above (35), wherein B is a phenyl group which may optionally be substituted by halogens;

(37) a compound according to the above (29), wherein Y is a divalent aliphatic hydrocarbon group;

(38) a compound according to the above (37), wherein Y is a divalent $C_{1-4}$ aliphatic hydrocarbon group;

(39) a pharmaceutical composition which comprises an oxazole derivative or a salt thereof as defined in the above (29);

(40) a composition according to the above (39) which is a neurotrophin production/secretion promoting agent;

(41) a composition according to the above (39) which is a prophylactic/therapeutic agent for neuropathy;

(42) a composition according to the above (39) which is a prophylactic/therapeutic agent for peripheral neuropathy;

(43) 4-(4-chlorophenyl)-2-(2-methyl-1-imidazolyl)-5-[3-(2-methylphenoxy)propyl]oxazole or a salt thereof;

(44) a crystal of 4-(4-chlorophenyl)-2-(2-methyl-1-imidazolyl)-5-[3-(2-methylphenoxy)propyl]oxazole or a salt thereof;

(45) 4-(4-chlorophenyl)-2-(2-methyl-1-imidazolyl)-5-[3-(3-methylphenoxy)propyl]oxazole or a salt thereof;

(46) a crystal of 4-(4-chlorophenyl)-2-(2-methyl-1-imidazolyl)-5-[3-(3-methylphenoxy)propyl]oxazole or a salt thereof;

(47) 5-[3-(4-chloro-2-methylphenoxy)propyl]-4-(4-chlorophenyl)-2-(2-methyl-1-imidazolyl)oxazole or a salt thereof;

(48) a crystal of 5-[3-(4-chloro-2-methylphenoxy)propyl]-4-(4-chlorophenyl)-2-(2-methyl-1-imidazolyl)oxazole or a salt thereof;

(49) a method for promoting neurotrophin production/secretion in a mammal in need thereof, which comprises administering to said mammal an effective amount of an azole derivative or a salt thereof as defined in the above (1);

(50) a method for promoting neurotrophin production/secretion in a mammal in need thereof, which comprises administering to said mammal an effective amount of a thiazole derivative or a salt thereof as defined in the above (18);

(51) a method for promoting neurotrophin production/secretion in a mammal in need thereof, which comprises administering to said mammal an effective amount of an oxazole derivative or a salt thereof as defined in the above (29);

(52) a method for preventing or treating neuropathy in a mammal in need thereof, which comprises administering to said mammal an effective amount of a thiazole derivative or a salt thereof as defined in the above (18);

(53) a method for preventing or treating neuropathy in a mammal in need thereof, which comprises administering to said mammal an effective amount of an oxazole derivative or a salt thereof as defined in the above (29);

(54) use of an azole derivative or a salt thereof as defined in the above (1) for the manufacture of a neurotrophin production/secretion promoting agent;

(55) use of a thiazole derivative or a salt thereof as defined in the above (18) for the manufacture of a neurotrophin production/secretion promoting agent;

(56) use of an oxazole derivative or a salt thereof as defined in the above (29) for the manufacture of a neurotrophin production/secretion promoting agent;

(57) use of a thiazole derivative or a salt thereof as defined in the above (18) for the manufacture of a pharmaceutical preparation for preventing or treating neuropathy;

(58) use of an oxazole derivative or a salt thereof as defined in the above (29) for the manufacture of a pharmaceutical preparation for preventing or treating neuropathy; etc.

BEST MODE FOR CARRYING OUT THE INVENTION

Figure 1:
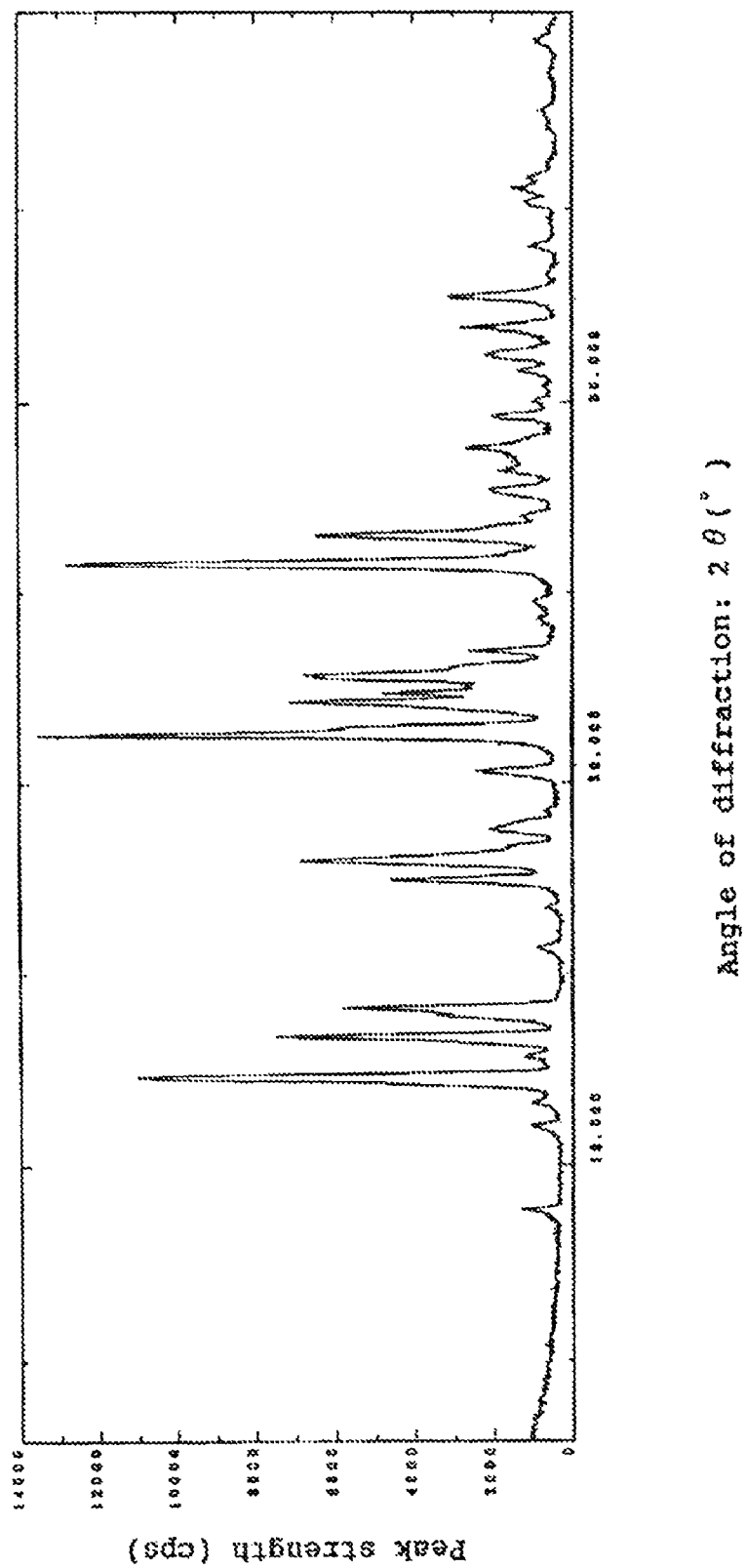
FIG. 1 shows the powder X-ray diffraction pattern of the crystals obtained in Example 122.

In the above formula (I), the respective substituents are defined as follows:

1) Heterocyclic Group (R¹, A)

The heterocyclic group which may optionally be substituted, for R¹ or A includes 5- or 6-membered rings containing 1 to 4 atoms each selected from among nitrogen, oxygen and sulfur atoms as ring-constituting atoms in addition to carbon atoms, and condensed rings derived therefrom. As the condensed rings, there may be mentioned, condensed rings comprising such a 5- or 6-membered ring and a 6-membered ring containing 1 or 2 nitrogen atoms or a benzene ring or a 5-membered ring containing one sulfur atom.

Specific examples of the heterocyclic group include aromatic heterocyclic groups such as pyridyl (e.g. 2-pyridyl, 3-pyridyl, 4-pyridyl), pyrimidinyl (e.g. 2-pyrimidinyl, 5-pyrimidinyl, 6-pyrimidinyl), pyridazinyl (e.g. 3-pyridazinyl, 4-pyridazinyl), pyrazinyl (e.g. 2-pyrazinyl), pyrrolyl (e.g. 1-pyrrolyl, 2-pyrrolyl), imidazolyl (e.g. 1-imidazolyl, 2-imidazolyl, 4-imidazolyl, 5-imidazolyl), pyrazolyl (e.g. 1-pyrazolyl, 3-pyrazolyl, 4-pyrazolyl), isoxazolyl, isothiazolyl, thiazolyl (e.g. 2-thiazolyl, 4-thiazolyl, 5-thiazolyl), oxazolyl (e.g. 2-oxazolyl, 4-oxazolyl, 5-oxazolyl), 1,2,4-oxadiazolyl (e.g. 1,2,4-oxadiazol-5-yl), 1,2,4-triazolyl (e.g. 1,2,4-triazol-1-yl, 1,2,4-triazol-3-yl), 1,2,3-triazolyl (e.g. 1,2,3-triazol-2-yl, 1,2,3-triazol-4-yl), tetrazolyl (e.g. tetrazol-1-yl, tetrazol-5-yl), benzimidazoyl (e.g. benzimidazol-1-yl, benzimidazol-2-yl), indolyl (e.g. indol-1-yl, indol-3-yl), 1H-indazolyl (e.g. 1H-indazol-1-yl), 1H-pyrrolo[2,3-b]pyrazinyl (e.g. 1H-pyrrolo[2,3-b]pyrazin-1-yl), 1H-pyrrolo[2,3-b]pyridyl (e.g. 1H-pyrrolo[2,3-b]pyridin-1-yl), 1H-imidazo[4,5-b]pyridyl (e.g. 1H-imidazo[4,5-b]pyridin-1-yl), 1H-imidazo[4,5-c]pyridyl (e.g. 1H-imidazo[4,5-c]pyridin-1-yl), 1H-imidazo[4,5-b]pyrazolyl (e.g. 1H-imidazo[4,5-b]pyrazin-1-yl), benzotriazolyl, etc.; and non-aromatic heterocyclic groups such as pyrrolidinyl (e.g. 1-pyrrolidinyl), piperidyl (e.g. 1-piperidyl), morpholinyl (e.g. morpholin-4-yl), thiomorpholinyl (e.g. thiomorpholin-4-yl), piperazinyl (e.g. 1-piperazinyl), hexamethyleniminyl (e.g. hexamethylenimin-1-yl), oxazolidinyl (e.g. oxazolidin-3-yl), thiazolidinyl (e.g. thiazolidin-3-yl, thiazolidin-2-yl), imidazolidinyl (e.g. imidazolidin-3-yl), imidazolinyl (e.g. imidazolin-1-yl, imidazolin-2-yl), oxazolinyl (e.g. oxazolin-2-yl), thiazolinyl (e.g. thiazolin-2-yl), oxazinyl (e.g. oxazin-2-yl), etc. Preferred are azolyl groups (e.g. pyrrolyl, imidazolyl, pyrazolyl, isoxazolyl, isothiazolyl, thiazolyl, oxazolyl, 1,2,4-oxadiazolyl, 1,2,4-triazolyl, 1,2,3-triazolyl, tetrazolyl), azolinyl groups (e.g. imidazolinyl, oxazolinyl, thiazolinyl), and azolidinyl (e.g. pyrollidinyl, oxazolidinyl, thiazolidinyl, imidazolidinyl).

1-1) Substituents on the Heterocyclic Group

The heterocyclic group for $R^1$ or A may have 1 to 3 substituents at substitutable positions. Examples of the substituents include aliphatic hydrocarbon groups, alicyclic hydrocarbon groups, aryl groups, aromatic heterocyclic groups, non-aromatic heterocyclic groups, halogen atoms, nitro group, an amino group which may optionally be substituted, acyl groups, which may optionally be substituted, a hydroxy group which may optionally be substituted, a thiol group which may optionally be substituted, a carboxy group which may optionally be esterified or amidated, and oxo group.

As said oxo-substituted heterocyclic groups, there may be mentioned, for example, azolidinyl groups substituted by one or two oxo groups. Typical examples thereof are 2-oxoimidazolidinyl (e.g. 2-oxoimidazolidin-1-yl), 2,4-dioxoimidazolidinyl (e.g. 2,4-dioxoimidazolidin-3-yl), 2,4-dioxooxazoldinyl (e.g. 2,4-dioxooxazolidin-3-yl) and 2,4-dioxothiazolidinyl (e.g. 2,4-dioxothiazolidin-3-yl).

Said aliphatic hydrocarbon groups include straight-chain or branched aliphatic hydrocarbon groups containing 1 to 15 carbon atoms, for example alkyl groups, alkenyl groups, alkynyl groups, and the like.

Preferred examples of the alkyl groups are $C_{1-10}$ alkyl groups such as methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2,-dimethylbutyl, 3,3-dimethylbutyl, 2-ethylbutyl, heptyl, octyl, nonyl and decyl.

Preferred examples of the alkenyl groups are $C_{2-10}$ alkenyl groups such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

Preferred examples of the alkynyl groups are $C_{2-10}$ alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

Said alicyclic hydrocarbon groups include saturated or unsaturated alicyclic hydrocarbon groups containing 3 to 12 carbon atoms, such as cycloalkyl groups, cycloalkenyl groups and cycloalkadienyl groups.

Preferred examples of the cycloalkyl groups are $C_{3-10}$ cycloalkyl groups such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl and bicyclo [4.3.1]decyl.

Preferred examples of the cycloalkenyl groups are $C_{3-10}$ cycloalkenyl groups such as 2-cyclopenten-1-yl, 3-cyclopenten-1-yl, 2-cyclohexen-1-yl and 3-cyclohexen-1-yl.

Preferred examples of the cycloalkadienyl groups are $C_{4-10}$ cycloalkadienyl groups such as 2,4-cyclopentadien-1-yl, 2,4-cyclohexadien-1-yl and 2,5-cyclohexadien-1-yl.

The "aryl group" means a monocyclic or condensed polycyclic aromatic hydrocarbon group, and preferred examples thereof include $C_{6-14}$ aryl groups such as phenyl, naphthyl, anthryl, phenanthryl and acenaphthylenyl. Among these, preferred are phenyl, 1-naphthyl, 2-naphthyl.

Preferred examples of the aromatic heterocyclic groups include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.; aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenathridinyl, phenathrolinyl, indolidinyl, pyrrolo[1,2-b]pyridazinyl, pyrazolo[1,5-a]pyridyl, imidazo[1,2-a]pyridyl imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl; and so forth.

Preferred examples of the non-aromatic heterocyclic groups include oxiranyl, azetidinyl, oxetanyl, thietanyl, tetrahydrofuryl, thiolanyl, piperidyl, tetrahydropyranyl, morpholinyl, thiomorpholinyl, piperazinyl and pyrrolidinyl.

Examples of the halogen atoms include fluorine, chlorine, bromine and iodine. Especially preferred are fluorine and chlorine.

Examples of the amino group which may optionally be substituted, include an amino group (—$NH_2$ group) which may be mono- or di-substituted by a substituent selected from the group consisting of $C_{1-10}$ alkyl groups which may be substituted by hydroxy, $C_{2-10}$ alkenyl groups, $C_{3-10}$ cycloalkyl groups, $C_{1-10}$ acyl groups (e.g. formyl, $C_{1-9}$ alkyl-carbonyl), $C_{6-12}$ aromatic groups (e.g. $C_{6-12}$ aryl groups such as phenyl), $C_{7-10}$ aralkyl groups (e.g., benzyl). Specific examples of the substituted amino group include methylamino, dimethylamino, ethylamino, diethylamino, dibutylamino, diallylamino, cyclohexylamino, acetylamino, propionylamino, benzoylamino, phenylamino, N-methyl-N-phenylamino, N-methyl-N-benzylamino, N-methyl-N-hydroxyethylamino.

Examples of the acyl groups in the acyl groups which may optionally be substituted, include $C_{1-3}$ acyl groups, specifically formyl and groups resulting from binding of a $C_{1-10}$ alkyl group, a $C_{3-10}$ cycloalkyl group, a $C_{2-10}$ alkenyl group, a $C_{3-10}$ cycloalkenyl group or a $C_{6-12}$ aromatic group (e.g. a $C_{6-12}$ aryl group such as phenyl) to carbonyl group (e.g. $C_{1-10}$ alkyl-carbonyl groups such as acetyl, propionyl, butyryl, isobutyryl, valeryl, isovaleryl, pivaloyl, hexanoyl, heptanoyl, octanoyl; $C_{3-10}$ cycloalkyl-carbonyl groups such as cyclobutanecarbonyl, cyclopentanecarbonyl, cyclohexanecarbonyl and cycloheptanecarbonyl; $C_{2-10}$ alkenyl-carbonyl groups such as crotonyl; $C_{3-10}$ cycloalkenyl-carbonyl groups such as 2-cyclohexenecarbonyl; and $C_{6-12}$ aryl-carbonyl groups such as benzoyl, nicotinoyl); phosphono group, etc. Examples of the substituents in the substituted acyl groups include $C_{1-3}$ alkyl groups, $C_{1-3}$ alkoxy groups, halogen (e.g. chlorine, fluorine, bromine), nitro, hydroxy, amino.

Referring to the hydroxy group which may optionally be substituted, examples of the substituted hydroxy group include alkoxy groups which may be substituted by optionally halogenated $C_{1-6}$ alkyl-carbonylamino (e.g., trifluoroacetylamino); alkenyloxy groups; aralkyloxy groups; acyloxy groups; aryloxy groups; alkylsulfonyloxy groups; arylsulfonyloxy groups; indanyloxy group; a tetrahydronaphthoxy group which may be substituted by 1 to 4 $C_{1-6}$ alkyl (e.g., methyl).

Preferred examples of the alkoxy groups are $C_{1-10}$ alkoxy groups such as methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutoxy, cyclopentyloxy, cyclohexyloxy.

Preferred examples of the alkenyloxy groups are $C_{2-10}$ alkenyloxy groups such as allyloxy, crotyloxy, 2-pentenyloxy, 3-hexenyloxy, 2-cyclopentenylmethoxy, 2-cyclohexenylmethoxy.

Preferred examples of the aralkyloxy groups are $C_{1-10}$ aralkyloxy groups such as phenyl-$C_{1-4}$ alkyloxy groups (e.g. benzyloxy, phenethyloxy).

Preferred examples of the acyloxy groups are $C_{2-13}$ acyloxy groups, more preferably $C_{2-4}$ alkanoyloxy groups (e.g. acetyloxy, propionyloxy, butyryloxy, isobutyryloxy).

Preferred examples of the aryloxy groups are $C_{6-14}$ aryloxy groups such as phenoxy, naphthyloxy. Said aryloxy groups (preferably phenoxy) may have 1 or 3 (preferably 1 or 2) substituents. Examples of such substituents include halogens (e.g. chlorine, fluorine, bromine), optionally halogenated $C_{1-4}$ alkoxy groups (e.g., methoxy, ethoxy, propoxy, isopropoxy, trifluoromethoxy); $C_{1-4}$ alkyl groups (e.g., methyl, ethyl, propyl, isopropyl, butyl, isobutyl, tert-butyl) which may be substituted by hydroxy, carboxy, $C_{1-6}$ alkoxy-carbonyl (e.g., methoxycarbonyl) or cyano; cyano; carboxy; hydroxy; $C_{6-10}$ aryloxy (e.g., phenoxy); $C_{1-6}$ alkoxy-carbonyl (e.g., methoxycarbonyl); $C_{1-6}$ alkylsulfanyl (e.g., methylsulfanyl); $C_{1-6}$ alkyl-carbonyloxy (e.g., acetyloxy). As the substituted aryloxy groups, there may be mentioned, 2-,3- or 4-chlorophenoxy; 2-,3- or 4-methoxyphenoxy; 2,3- or 4-methylphenoxy; 2-,3- or 4-cyanophenoxy; 2-,3- or 4-hydroxyphenoxy.

Preferred examples of the alkylsulfonyloxy groups are $C_{1-10}$ alkylsulfonyloxy groups such as methylsulfonyloxy and ethylsulfonyloxy.

Preferred examples of the arylsulfonyloxy groups are $C_{1-10}$ arylsulfonyloxy groups (said $C_{6-12}$ arylsulfonyloxy groups may be substituted by $C_{1-6}$ alkyl such as methyl), such as phenylsulfonyloxy and 4-methylphenylsulfonyloxy.

Referring to the thiol group which may optionally be substituted (mercapto group which may optionally be substituted), examples of the substituted thiol group include alkylsulfanyl groups which may be substituted by hydroxy, arylsulfanyl groups, heteroaryl sulfanyl groups, aralkylsulfanyl groups, heteroarylalkylsulfanyl groups and acylsulfanyl groups.

Preferred examples of the alkylsulfanyl groups are $C_{1-10}$ alkylsulfanyl groups (e.g. methylsulfanyl, ethylsulfanyl, propylsulfanyl, isopropylsulfanyl, butylsulfanyl, isobutylsulfanyl, sec-butylsulfanyl, tert-butylsulfanyl, pentylsulfanyl, isopentylsulfanyl, neopentylsulfanyl, hexylsulfanyl, heptylsulfanyl, nonylsulfanyl, cyclobutylsulfanyl, cyclopentylsulfanyl, cyclohexylsulfanyl).

Preferred examples of the arylsulfanyl groups are $C_{6-14}$ arylsulfanyl groups which may optionally be substituted by a $C_{1-6}$ alkyl group, such as phenylsulfanyl, naphthylsulfanyl and 4-methylphenylsulfanyl.

Examples of the heteroarylsulfanyl groups include a thiol group substituted by the aromatic heterocyclic groups mentioned above. Among these, preferred are 2-pyridylsulfanyl, 3-pyridylsulfanyl, 2-imidazolylsulfanyl, 1,2,4-triazol-5-ylsulfanyl, 2-pyrimidinylsulfanyl.

Preferred examples of the aralkylsulfanyl groups are $C_{7-10}$ aralkylsulfanyl groups such as phenyl-$C_{1-4}$ alkylsulfanyl groups (e.g. benzylsulfanyl, phenethylsulfanyl).

Examples of the heteroarylalkylsulfanyl groups include an alkylsulfanyl group substituted by the aromatic heterocyclic groups mentioned above. Said alkyl sulfanyl group includes those alkylsulfanyl groups mentioned above.

Preferred examples of the heteroarylalkylsulfanyl groups include pyridyl-$C_{1-4}$ alkylsulfanyl groups (e.g. 2-pyridylmethylsulfanyl, 3-pyridylmethylsulfanyl).

Preferred examples of the acylsulfanyl groups include $C_{2-13}$ acylsulfanyl groups, more preferably $C_{2-4}$ alkanoylsulfanyl groups (e.g. acetylsulfanyl, propionylsulfanyl, butyrylsulfanyl, isobutyrylsulfanyl).

Referring to the carboxy group which may be esterified or amidated, examples of the esterified carboxy group include alkoxycarbonyl groups, aralkyloxycarbonyl groups, aryloxycarbonyl groups and heteroarylalkyloxycarbonyl groups.

Preferred examples of the alkoxycarboyl groups are $C_{2-5}$ alkoxycarbonyl groups, namely $C_{1-4}$ alkoxy-carbonyl groups, such as methoxycarbonyl, ethoxycarbonyl, propoxycarbonyl and butoxycarbonyl.

Preferred examples of the aralkyloxycarbonyl groups are $C_{8-10}$ aralkyloxycarbonyl groups, namely $C_{7-9}$ aralkyloxy-carbonyl groups such as benzyloxycarbonyl.

Preferred examples of the aryloxycarbonyl groups are $C_{7-15}$ aryloxycarbonyl groups, namely $C_{6-14}$ aryloxy-carbonyl groups which may optionally be substituted by $C_{1-6}$ alkyl groups, such as phenoxycarbonyl and p-tolyloxycarbonyl.

Examples of the heteroarylalkyloxycarbonyl groups include alkyloxycarbonyl groups substituted by the aromatic heterocyclic groups mentioned above. As said alkyloxycarbonyl groups, there may be mentioned the same groups as those alkoxycarbonyl groups mentioned above. Preferred examples of the heteroarylalkyloxycarbonyl groups include pyridyl-$C_{1-4}$ alkoxy-carbonyl groups (e.g. 2-pyridylmethoxycarbonyl, 3-pyridylmethoxycarbonyl).

Referring to the carboxyl group which may be esterified or amidated, the amidated carboxyl group includes groups of the formula: —CON(R5)(R$^6$) wherein R$^5$ and R$^6$ are the same or different and each represents hydrogen atom, a hydrocarbon group which may optionally be substituted, a hydroxy group which may optionally be substituted, or a heterocyclic group which may optionally be substituted. Examples of the hydrocarbon group in the hydrocarbon group which may optionally be substituted for R$^5$ or R$^6$, include the aliphatic hydrocarbon groups, alicyclic hydrocarbon groups and aryl groups mentioned as examples of the substituents on the heterocyclic group for R$^1$ or A. The hydroxy group which may optionally be substituted for R$^5$ or R$^6$ includes the same groups as the hydroxy group which may optionally be substituted for R$^1$ or A. Further, examples of the heterocyclic group in the heterocyclic group which may optionally be substituted for R$^5$ or R$^6$, include the aromatic heterocyclic groups mentioned as examples of the substituents on the heterocyclic group for R$^1$ or A. As the substituents in R$^5$ or R$^6$, there may be mentioned one to three substituents selected from halogen atoms (e.g. chlorine, fluorine, bromine, iodine), $C_{1-4}$ alkyl groups and $C_{1-4}$ alkoxy groups.

1-2) Substituents of the Substituents on the Heterocyclic Group

Referring to formula (I), the substituents on the heterocyclic group for R$^1$ or A, when they are substituents containing an aliphatic hydrocarbon group, an alicyclic hydrocarbon group, an aryl group, an aromatic heterocyclic group, a non-aromatic heterocyclic group, may further have one or more, preferably 1 to 3, appropriate substituents. Examples of such substituents include $C_{1-6}$ alkyl groups which may optionally be halogenated or substituted by a substituent selected from carboxyl, $C_{2-8}$ alkoxycarbonyl, hydroxy and optionally be halogenated $C_{1-4}$ alkoxy; $C_{2-6}$ alkenyl groups; $C_{2-6}$ alkynyl groups; $C_{3-7}$ cycloalkyl groups; $C_{6-14}$ aryl groups (e.g. phenyl, naphthyl); aromatic heterocyclic groups (e.g. thienyl, furyl, pyridyl, oxazolyl, thiazolyl); non-aromatic heterocyclic groups (e.g. tetrahydrofuryl, morpholinyl, thiomorpholinyl, piperidyl, pyrrolidinyl, piperazinyl); $C_{7-9}$ aralkyl groups (e.g. benzyl); amino group; N-mono($C_{1-4}$)alkylamino groups; N,N-di($C_{1-4}$)alkylamino groups; $C_{2-8}$ acylamino groups (e.g. $C_{1-7}$ alkyl-carbonylamino such as acetylamino and propionylamino; benzoylamino); amidino group; $C_{2-8}$ acyl groups (e.g. $C_{1-7}$ alkyl-carbonyl such as acetyl); carbamoyl group; N-mono($C_{1-4}$)alkylcarbamoyl groups; N,N-di($C_{1-4}$)alkylcarbamoyl groups; sulfamoyl group; N-mono($C_{1-4}$)alkylsulfamoyl groups; N,N-di($C_{1-4}$)alkylsulfamoyl groups; carboxyl group; $C_{2-8}$ alkoxycarbonyl groups; hydroxy group; optionally halogenated $C_{1-4}$ alkoxy groups; $C_{2-5}$ alkenyloxy groups; $C_{3-7}$ cycloalkyloxy groups; $C_{7-9}$ aralkyloxy groups (e.g. benzyloxy); $C_{6-14}$ aryloxy groups (e.g. phenyloxy, naphthyloxy); mercapto group; optionally halogenated $C_{1-4}$ alkylsulfanyl groups; $C_{7-9}$ aralkylsulfanyl groups (e.g. benzylsulfanyl); $C_{6-14}$ arylsulfanyl groups (e.g. phenylsulfanyl, naphthylsulfanyl); sulfo group; cyano group; azido group; nitro group; nitroso group; and halogen atoms (e.g. fluorine, chlorine, bromine, iodine).

2) Definition of R$^1$

Referring to formula (I), the halogen atom, the hydroxy group which may optionally be substituted, the thiol group which may optionally be substituted, and the amino group which may optionally be substituted, for R$^1$ respectively include those mentioned as examples of the substituents on the heterocyclic group for R$^1$ or A.

Referring to formula (I), R$^1$ is preferably a heterocyclic group which may optionally be substituted. R$^1$ is preferably a nitrogen-containing heterocyclic group which may optionally be substituted, as well as an aromatic heterocyclic group which may optionally be substituted. Among these, R$^1$ is more preferably a 5-membered nitrogen-containing aromatic heterocyclic group which may optionally be substituted, especially preferably an imidazolyl group which may optionally be substituted.

2') Definition of A

Referring to formula (I), the acyl group which may optionally be substituted, the hydroxy group which may optionally be substituted, and the carboxy group which may optionally be esterified or amidated, for A respectively include those mentioned as examples of the substituents on the heterocyclic group for R$^1$ or A.

Referring to formula (I), A is preferably a heterocyclic group which may optionally be substituted, or a hydroxy group which may optionally be substituted. Among these, A is preferably an aryloxy group which may optionally be substituted. Especially preferred is a phenoxy group which may optionally be substituted by an alkyl group which may optionally be substituted (preferably a phenoxy group which may optionally substituted by an alkyl group).

3) Aromatic Group for B

Referring to the formula (I), examples of the aromatic group in the aromatic group which may optionally be substituted, for B include an aromatic hydrocarbon group, an aromatic heterocyclic group, etc.

Preferred examples of the aromatic hydrocarbon group are $C_{6-14}$ aromatic hydrocarbon groups such as $C_{6-14}$ aryl groups (e.g. phenyl, naphthyl).

Preferred examples of the aromatic heterocyclic group are those mentioned as examples of the substituents on the heterocyclic group for R$^1$ or A. Among these, preferred are, for example, furyl, thienyl, pyridyl, quinolyl.

3-1) Substituents on the Aromatic Group for B

Examples of the substituents in the aromatic group which may optionally be substituted, for B include one to three substituents selected from halogen atoms, nitro group, cyano group, alkoxy groups which may optionally be substituted, alkyl groups which may optionally be substituted, cycloalkyl groups which may optionally be substituted, and the like.

Examples of the halogen atoms include fluorine, chlorine, bromine, iodine, etc.

Examples of the alkoxy groups in the alkoxy groups which may optionally be substituted, include those mentioned as examples of the substituents on the heterocyclic group for R$^1$ or A. Among these, preferred are straight-chain or branched $C_{1-6}$ alkoxy groups.

Examples of the alkyl groups in the alkyl groups which may optionally be substituted, include those mentioned as examples of the substituents on the heterocyclic group for R$^1$ or A. Among these, preferred are straight-chain or branched $C_{1-6}$ alkyl groups.

Examples of the cycloalkyl groups in the cycloalkyl groups which may optionally be substituted, include those mentioned as examples of the substituents on the heterocyclic group for R$^1$ or A. Among these, preferred are $C_{3-7}$ cycloalkyl groups.

Examples of the substituents in the above mentioned alkoxy groups which may optionally be substituted, the alkyl groups which may optionally be substituted, and the cycloalkyl groups which may optionally be substituted, include one to three substituents selected from halogen atoms (e.g. fluorine, chlorine, bromine, iodine), hydroxy group, $C_{1-6}$ alkoxy groups.

Examples of the substituted alkoxy groups include trifluoromethoxy, difluoromethoxy, 2,2,2-trifluoroethoxy and 1,1-difluoroethoxy.

Examples of the substituted alkyl groups include trifluoromethyl, difluoromethyl, 2,2,2-trifluoroethyl, trichloromethyl, 1-hydroxymethyl, methoxymethyl, ethoxymethyl, 2-methoxyethyl and 2,2-dimethoxyethyl.

Referring to the formula (I), B is preferably an aromatic hydrocarbon group which may optionally be substituted, and, in particular, a phenyl group which may optionally be substituted, is generally used.

4) Definitions of Y and X

Referring to the formula (I), examples of the divalent hydrocarbon group for Y include a divalent aliphatic hydrocarbon group, a divalent alicyclic hydrocarbon group, and a divalent aromatic hydrocarbon group.

The divalent aliphatic hydrocarbon group for Y may be straight-chain or branched, and may be saturated or unsaturated. Said aliphatic hydrocarbon group includes those divalent groups formed by removing one hydrogen atom from the aliphatic hydrocarbon groups mentioned as examples of the substituents on the heterocyclic group for $R^1$ or A, and preferably contain 1 to 7 carbon atoms. As specific examples, there may be mentioned saturated ones such as —$CH_2$—, —$CH(CH_3)$—, —$(CH_2)_2$—, —$CH(C_2H_5)$—, —$(CH_2)_3$—, —$(CH_2)_4$—, —$(CH_2)_5$—, —$(CH_2)_6$— and —$(CH_2)_7$—; and unsaturated ones such as —CH=CH—, —$C(CH_3)$=CH—, —CH=CH—$CH_2$—, —$C(C_2H_5)$=CH—, —$CH_2$—CH=CH—$CH_2$—, —$CH_2$—$CH_2$—CH=CH—$CH_2$—, —CH=CH—CH=CH—$CH_2$— and —CH=CH—CH=CH—CH=CH—$CH_2$—, among others. Y is preferably a divalent $C_{1-4}$ aliphatic hydrocarbon group, more preferably a saturated one. Examples of the preferred species of Y include —$(CH_2)_3$— and —$(CH_2)_4$—.

The divalent alicyclic hydrocarbon group for Y includes those divalent groups formed by removing one hydrogen atom from the alicyclic hydrocarbon groups mentioned as examples of the substituents on the heterocyclic group for $R^1$ or A.

The divalent aromatic hydrocarbon group for Y includes those divalent groups formed by removing one hydrogen atom from the aryl groups mentioned as examples of the substituents on the heterocyclic group for $R^1$ or A.

Referring to the formula (I), examples of the divalent heterocyclic group for Y include a divalent aromatic heterocyclic group, a divalent non-aromatic hydrocarbon group.

The divalent aromatic heterocyclic group for Y includes those divalent groups formed by removing one hydrogen atom from the aromatic heterocyclic groups mentioned as examples of the substituents on the heterocyclic group for $R^1$ or A.

The divalent non-aromatic hydrocarbon group for Y includes those divalent groups formed by removing one hydrogen atom from the non-aromatic hydrocarbon groups mentioned as examples of the substituents on the heterocyclic group for $R^1$ or A.

Referring to the formula (I), Y is preferably a divalent aliphatic hydrocarbon group. Especially, an alkylene group is generally used.

Referring to the formula (I), X represents an oxygen atom, a sulfur atom, or a nitrogen atom which may optionally be substituted, and preferably is an oxygen atom or sulfur atom.

Examples of the nitrogen atom which may optionally be substituted, for X include —$NR^4$— wherein $R^4$ represents a hydrogen atom, a hydrocarbon group which may optionally be substituted, an acyl group which may optionally be substituted, or a heterocyclic group which may optionally be substituted.

Said hydrocarbon group which may optionally be substituted, for $R^4$ includes those hydrocarbon groups which may optionally be substituted, mentioned as examples of the substituents on the heterocyclic group for $R^1$ or A.

Said acyl group which may optionally be substituted, for $R^4$ includes those acyl groups which may optionally be substituted, mentioned as examples of the substituents on the heterocyclic group for $R^1$ or A.

Said heterocyclic group which may optionally be substituted, for $R^4$ includes the same as the heterocyclic groups which may optionally be substituted, for $R^1$ or A.

$R^4$ is preferably a hydrogen atom and hydrocarbon groups which may optionally be substituted. Among these, preferred are a hydrogen atom and alkyl groups which may optionally be substituted. Especially preferred are a hydrogen atom and lower ($C_{1-4}$) alkyl groups.

5) Preferred Compounds

Preferred embodiments of the compound of the formula (I) of the present invention (hereinafter sometimes referred to as "compound (I)") include the following cases.

(1) The case in which, in the formula (I), $R^1$ is a heterocyclic group which may optionally be substituted, and in which said heterocyclic group is (i) a 5- or 6-membered ring containing, as ring-constituting atoms in addition to carbon atoms, 1 to 4 hetero atoms selected from nitrogen atom, oxygen atom and sulfur atom, or (ii) a condensed ring of such 5- or 6-membered ring and a 6-membered ring containing 1 or 2 nitrogen atoms, benzene ring or a 5-membered ring containing one nitrogen atom (more preferably an azolyl group).

(2) The case in which, in the formula (I), A is a heterocyclic group which may optionally be substituted, and in which said heterocyclic group is (i) a 5- or 6-membered ring containing, as a ring-constituting atoms in addition to carbon atoms, 1 to 4 hetero atoms selected from nitrogen atom, oxygen atom and sulfur atom, or (ii) a condensed ring of 5- or 6-membered ring and a 6-membered ring containing 1 or 2 nitrogen atoms, benzene ring or a 5-membered ring containing one nitrogen atom (more preferably an azolyl group, azolinyl group or azolidinyl group).

(3) The case in which, in the formula (I), A is a hydroxy group which may optionally be substituted, more preferably (i) hydroxy group, (ii) a $C_{1-10}$ alkoxy group, (iii) a $C_{2-10}$ alkenyloxy group, (iv) a $C_{7-10}$ aralkyloxy group, (v) a $C_{2-13}$ acyloxy group, (vi) a $C_{6-14}$ aryloxy group which may optionally be substituted by 1 to 3 halogens, $C_{1-6}$ alkyl or $C_{1-4}$ alkoxy, or (vii) a $C_{1-10}$ alkylsulfonyloxy group;

(4) The case in which, in the formula (I), Y is a divalent aliphatic hydrocarbon group containing 1 to 7 carbon atoms, more preferably a divalent aliphatic hydrocarbon group containing 2 to 4 carbon atoms.

(5) The case in which, in the formula (I), $R^1$ is (i) a halogen atom, (ii) an imidazolyl, pyrazolyl, 1,2,4-triazolyl, 1,2,3-triazolyl, benzimidazolyl, pyrrolidinyl, piperidinyl, morpholinyl or hexamethyleniminyl group, which may optionally have 1 to 3 substituents selected from $C_{1-10}$ alkyl, $C_{6-14}$ aryl and $C_{1-10}$ alkylsulfanyl, (iii) a $C_{1-10}$ alkoxy group, (iv) a $C_{6-14}$ aryloxy group, (v) a $C_{1-10}$ alkylsulfanyl group, (vi) a $C_{6-14}$ arylsulfanyl group which may optionally be substituted by $C_{1-6}$ alkyl, (vii) a thiol group substituted by an imidazolyl, 1,2,3-triazolyl, 1,2,4-triazolyl or pyridyl, which may optionally be substituted by $C_{1-6}$ alkyl or $C_{6-14}$ aryl, (viii) a pyridyl- $C_{1-4}$ alkylsulfanyl group or (ix) an amino group which may optionally be substituted by 1 or 2 $C_{1-10}$ alkyl or $C_{3-10}$ cycloalkyl;

A is (i) formyl group, (ii) an imidazolyl, pyrazolyl, 1,2,4-triazolyl, 1,2,3-triazolyl, thiazolidinyl, oxazolinyl, thiazolinyl, 2,4-dioxoimidazolidinyl, 2,4-dioxooxazolidinyl or 2,4-dioxothiazolidinyl group, which may be substituted by $C_{1-10}$ alkyl, (iii) hydroxy group, (iv) a $C_{6-14}$ aryloxy group which may optionally be substituted by halogens, $C_{1-6}$ alkyl or $C_{1-4}$ alkoxy, (v) a $C_{1-10}$ alkylsulfonyloxy group, (vi) a $C_{1-4}$ alkoxycarbonyl group, (vii) a $C_{7-9}$ aralkyloxy-carbonyl group or (viii) a group of the formula: —CON($R^5$)($R^6$) wherein $R^5$ and $R^6$ independently represent hydrogen atom or a $C_{1-10}$ alkyl group which may optionally be substituted by $C_{1-10}$ alkoxy or halogens;

B is a phenyl group which may optionally be substituted by halogens; and

Y is —(CH$_2$)$_2$—, —(CH$_2$)$_3$—, —(CH$_2$)$_4$—, —(CH$_2$)$_5$— or —(CH$_2$)$_6$—.

(6) The case in which, in the formula (I), $R^1$ is a heterocyclic group which may optionally be substituted; A is a heterocyclic group which may optionally be substituted; and Y is a divalent aliphatic hydrocarbon group containing 1 to 7 carbon atoms.

(7) The case in which, in the above case (6), the heterocyclic groups for $R^1$ and A are independently an azolyl group, an azolinyl group or an azolidinyl group.

(8) The case in which, in the above case (6), the heterocyclic group for $R^1$ is an azolyl group and the heterocyclic group for A is an azolyl group, an azolinyl group or an azolidinyl group.

(9) The case in which, in the above case (7), the azolyl group, azolinyl group and azolidinyl group for $R^1$ and A are pyrrolyl, imidazolyl, pyrazolyl, isoxazolyl, isothiazolyl, thiazolyl, oxazolyl, 1,2,4-oxadiazolyl, 1,2,4-triazolyl, 1,2,3-triazolyl, tetrazolyl, pyrrolidinyl, oxazolidinyl, thiazolidinyl, imidazolidinyl, oxazolinyl and thiazolinyl groups.

(10) The case in which, in the above case (6), $R^1$ is an azolyl group which may optionally have 1 to 3 substituents selected from $C_{1-10}$ alkyl, $C_{6-14}$ aryl and $C_{1-10}$ alkylsulfanyl.

(11) The case in which, in the above case (10), the azolyl group is imidazolyl, pyrazolyl, 1,2,4-triazolyl or 1,2,3-triazolyl.

(12) The case in which, in the above case (6), A is an azolyl, azolinyl or azolidinyl group which may optionally be substituted by 1 or 2 $C_{1-10}$ alkyl or oxo groups, more preferably an imidazolyl, pyrazolyl, 1,2,4-triazolyl, 1,2,3-triazolyl, thiazolidinyl, oxazolinyl, thiazolinyl, 2,4-dioxoimidazolidinyl, 2,4-dioxooxazolidinyl or 2,4-dioxothiazolidinyl group which may optionally be substituted by $C_{1-10}$ alkyl.

(13) The case in which, in the above case (6), B is a phenyl group which may optionally be substituted, more preferably a phenyl group which may optionally be substituted by halogens.

(14) The case in which, in the above case (6), Y is a divalent aliphatic hydrocarbon group containing 3 to 5 carbon atoms, more preferably —(CH$_2$)$_3$—, —(CH$_2$)$_4$— or —(CH$_2$)$_5$—.

(15) The case in which, in the formula (I), $R^1$ is a heterocyclic group which may optionally be substituted; A is a hydroxy group which may optionally be substituted; and Y is a divalent aliphatic hydrocarbon group containing 1 to 7 carbon atoms.

(16) The case in which, in the above case (15), the heterocyclic group for $R^1$ is an azolyl group (e.g. a pyrrolyl, imidazolyl, pyrazolyl, isoxazolyl, isothiazolyl, thiazolyl, oxazolyl, 1,2,4-oxadiazolyl, 1,2,4-triazolyl, 1,2,3-triazolyl or tetrazolyl group).

(17) The case in which, in the above case (15), $R^1$ is an azolyl group (e.g. an imidazolyl, pyrazolyl, 1,2,4-triazolyl or 1,2,3-triazolyl group) which may have 1 to 3 substituents selected from $C_{1-10}$ alkyl, $C_{6-14}$ aryl and $C_{1-10}$ alkylsulfanyl.

(18) The case in which, in the above case (15), A is (i) hydroxy group, (ii) a $C_{1-10}$ alkoxy group, (iii) a $C_{2-10}$ alkenyloxy group, (iv) a $C_{7-10}$ aralkyloxy group, (v) a $C_{2-13}$ acyloxy group, (vi) a $C_{6-14}$ aryloxy group which may optionally be substituted by 1 to 3 substituents selected from halogens, $C_{1-6}$ alkyl and $C_{1-4}$ alkoxy or (vii) a $C_{1-10}$ alkylsulfonyloxy group, more preferably a $C_{6-14}$ aryloxy group which may optionally be substituted by 1 to 3 substituents selected from halogens, $C_{1-6}$ alkyl and $C_{1-4}$ alkoxy.

(19) The case in which, in the above case (15), B is a phenyl group which may optionally be substituted, more preferably a phenyl group substituted by halogens.

(20) The case in which, in the above case (15), Y is a divalent aliphatic hydrocarbon group containing 3 to 5 carbon atoms, more preferably —(CH$_2$)$_3$—, —(CH$_2$)$_4$— or —(CH$_2$)$_5$—.

(21) The case in which, in the formula (I), the compound is 4-(4-chlorophenyl)-2-(2-methyl-1-imidazolyl)-5-oxazolepropanol or a salt thereof, 4-(4-chlorophenyl)-2-(2-methyl-1-imidazolyl)-5-oxazolebutanol or a salt thereof, 4-(4-chlorophenyl)-5-[3-(1-imidazolyl)propyl]-2-(2-methyl-1-imidazolyl)oxazole or a salt thereof, 4-(4-chlorophenyl)-2-(2-methyl-1-imidazolyl)-5-oxazolepentanol or a salt thereof, or 4-(4-chlorophenyl)-5-[4-(1-imidazolyl)butyl]-2-(2-methyl-1-imidazolyl)oxazole or a salt thereof.

Preferred specific examples of the compound of the formula (I) include the following compounds (1) to (7):

(1) 4-(4-chlorophenyl)-5-[3-(2-methoxyphenoxy)propyl]-2-(2-methyl-1-imidazolyl)oxazole
(2) 3-[3-[4-(4-chlorophenyl)-2-(2-methyl-1-imidazolyl)-5-oxazolyl]propyl]-1-methyl-2,4-imidazolidinedione
(3) 4-(4-chlorophenyl)-5-[3-(3-methoxyphenoxy)propyl]-2-(2-methyl-1-imidazolyl)oxazole
(4) 4-(4-chlorophenyl)-5-[3-(4-methoxyphenoxy)propyl]-2-(2-methyl-1-imidazolyl)oxazole
(5) 4-(4-chlorophenyl)-2-(2-methyl-1-imidazolyl)-5-[3-(2-methylphenoxy)propyl]oxazole
(6) 4-(4-chlorophenyl)-2-(2-methyl-1-imidazolyl)-5-[3-(3-methylphenoxy)propyl]oxazole
(7) 5-[3-(4-chloro-2-methylphenoxy)propyl]-4-(4-chlorophenyl)-2-(2-methyl-1-imidazolyl)oxazole.

Hereinafter, these compounds are sometimes referred to simply as "compound (1)", "compound (2)", etc.

6) Novel Compounds

Among the above compounds (I) or salts thereof, thiazole derivatives of the formula (Ia):

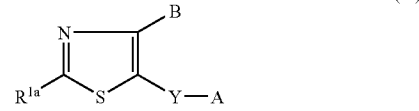

(Ia)

wherein $R^{1a}$ represents a heterocyclic group which may optionally be substituted, A represents an acyl group which may optionally be substituted, a heterocyclic group which may optionally be substituted, a hydroxy group which may optionally be substituted, or a carboxyl group which may optionally be esterified or amidated, B represents an aromatic group which may optionally be substituted, and Y represents a divalent aliphatic hydrocarbon group, or salt thereof; and oxazole derivatives of the formula (Ib):

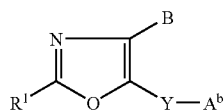

(Ib)

wherein $R^1$ represents a halogen atom, a heterocyclic group which may optionally be substituted, a hydroxy group which may optionally be substituted, a thiol group which may optionally be substituted, or an amino group which may optionally be substituted, $A^b$ represents an aryloxy group which is substituted by an alkyl group and may further be substituted, B represents an aromatic group which may optionally be substituted, and Y represents a divalent hydrocarbon group or a heterocyclic group, or salt thereof; are novel compounds.

The definition of each substituent in the above formulae is the same as that of the corresponding substituent in the compound of the formula (I) above. $R^{1a}$ is the same as the heterocyclic group which may optionally be substituted, for $R^1$. $A^b$ represents an aryloxy group which is substituted by an alkyl group and may further be substituted, among the aryloxy group which may be substituted, mentioned as examples of the above A. The alkyl group is preferably a $C_{1-4}$ alkyl group. The aryloxy group is preferably a $C_{6-14}$ aryl group. Examples of the substituents on the aryloxy group include halogen (e.g., chlorine, fluorine, bromine), a $C_{1-4}$ alkoxy group, a $C_{1-4}$ alkyl group, hydroxy, a $C_{1-6}$ alkyl-carbonyloxy group (e.g., acetyloxy).

$A^b$ is preferably an aryloxy group substituted by an alkyl group, more preferably a $C_{6-14}$ aryloxy group (preferably phenoxy) substituted by a $C_{1-4}$ alkyl group, especially preferably a group of the formula:

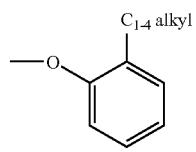

wherein $C_{1-4}$ alkyl is methyl, ethyl, propyl, isopropyl etc., preferably methyl etc.

Preferred examples of the compound (Ib) include the following compounds:

$A^b$ is a $C_{6-14}$ aryloxy group (preferably phenoxy) substituted by a $C_{1-4}$ alkyl group; $R^1$ is a 5-membered nitrogen-containing aromatic heterocyclic group which may optionally be substituted (preferably an imidazolyl group which may optionally be substituted, more preferably an imidazolyl group which may optionally be substituted by $C_{1-10}$ alkyl, especially preferably a group of the formula:

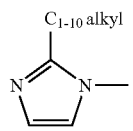

wherein $C_{1-10}$ alkyl is methyl, ethyl, propyl, isopropyl, butyl, pentyl, hexyl etc., preferably $C_{1-4}$ alkyl such as methyl, ethyl, propyl and isopropyl, more preferably methyl etc.); B is a phenyl group which may optionally be substituted (preferably a phenyl group which is optionally substituted by halogens, more preferably a group of the formula:

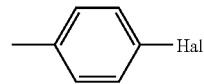

wherein Hal is a halogen atom such as fluorine, chlorine, bromine and iodine, preferably chlorine etc.); Y is a divalent aliphatic hydrocarbon group (preferably a divalent aliphatic hydrocarbon group containing 1 to 4 carbon atoms, more preferably $C_{1-4}$ alkylene group such as —$CH_2$—, —$(CH_2)_2$—, —$(CH_2)_3$— and —$(CH_2)_4$—, especially preferably —$(CH_2)_3$—).

7) Salts of the Compounds

The salt of compound (I) of the present invention is preferably a pharmacologically acceptable one and may be, for example a salt with an inorganic base, a salt with an organic base, a salt with an inorganic acid, a salt with an organic acid or a salt with a basic or acidic amino acid. Preferred examples of the salt with an inorganic base include alkali metal salts such as sodium salt and potassium salt; alkaline earth metal salts such as calcium salt and magnesium salt; and aluminum salt, ammonium salt and the like. Preferred examples of the salt with an organic base include salts with trimethylamine, triethylamine, pyridine, picoline, ethanolamine, diethanolamine, triethanolamine, dicyclohexylamine, N,N'-dibenzylethylenediamine, and the like. Preferred examples of the salt with an inorganic acid include salts with hydrochloric acid, hydrobromic acid, nitric acid, sulfuric acid, and phosphoric acid. Preferred examples of the salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like. Preferred examples of the salt with a basic amino acid include salts with arginine, lysine and ornithine, and preferred examples of the salt with an acidic amino acid include salts with aspartic acid, glutamic acid, and the like. Among these salts, a sodium salt and potassium salt are most preferred.

The compound (I) or a salt thereof, of the present invention may be in the form of a hydrate.

The compound (I) of the invention may be used in the form of a prodrug. The term "prodrug of compound (I)" as used herein means a compound capable of being converted to compound (I) in vivo by the action of an enzyme or gastric juice under physiological conditions, namely a compound capable of being converted to compound (I) upon enzymatic oxidation, reduction or hydrolysis, among others, or a compound capable of being converted to compound (I) upon hydrolysis by gastric juice. The prodrug of compound (I)

includes compounds derived by acylation, alkylation or phosphorylation of the amino group of compound (I) (e.g. compounds derived by eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation of the amino group of compound (I)), compounds derived by acylation, alkylation, phosphorylation or boration of the hydroxy group of compound (I) (e.g. compounds derived by acetylation, palmitoylation, propanoylation, pivaloylation, succinylation, fumarylation, alanylation or dimethylaminomethylcarbonylation of the hydroxy group of compound (I)), and compounds derived by esterification or amidation of the carboxyl group of compound (I) (e.g. compounds derived by ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, or methylamidation of the carboxyl group of compound (I)), among others. These compounds can be produced from compound (I) by per se known methods.

The prodrug of compound (I) may be one capable of being converted to compound (I) or salts thereof under physiological conditions, as described in "Iyakuhin no Kaihatsu (Development of Drugs)", vol 7, Molecular Designing, published by Hirokawa Shoten, 1990, pages 163-198.

The compound (I) may be labeled with an isotope (e.g. $^3$H, $^{14}$C, $^{35}$S, $^{125}$I).

The compound (I) or a salt thereof, of the present invention includes novel compounds, such as the compound of the formula (Ia) or a salt thereof, and the compound of the formula (Ib) or a salt thereof.

8) Administration Subjects

The compound (I) or a salt thereof, of the present invention (hereinafter sometimes referred to simply as "compound of the invention") is low in toxicity and can be safely administered, either as such or in the form of a preparation according to the present invention as prepared by admixing with a per se known pharmacologically acceptable carrier or the like, to mammals (e.g. human, mouse, rat, rabbit, dog, cat, cattle, horse, swine, monkey).

9) Pharmaceutical Preparations

The above-mentioned pharmacologically acceptable carrier includes those various organic or inorganic carrier substances which are conventionally used as pharmaceutical preparation materials. They are incorporated as excipients, lubricants, binders, disintegrants or the like in solid preparations; as solvents, solubilizers, suspending agents, isotonizing agents, buffers, local analgesics or the like in liquid preparations. According to necessity, additives such as preservatives, antioxidants, coloring agents and sweeteners may be used.

Preferred examples of the excipients include lactose, sucrose, D-mannitol, D-sorbitol, starch, gelatinized starch, dextrin, crystalline cellulose, low-substituted hydroxypropylcellulose, carboxymethylcellulose sodium, gum arabic, pullulan, light silicic anhydride, synthetic aluminum silicate, magnesium aluminometasilicate and the like.

Preferred examples of the lubricants include magnesium stearate, calcium stearate, talc and colloidal silica.

Preferred examples of the binders include gelatinized starch, sucrose, gelatin, gum arabic, methylcellulose, carboxymethylcellulose, carboxymethylcellulose sodium, crystalline cellulose, saccharose, D-mannitol, trehalose, dextrin, pullulan, hydroxypropylcellulose, hydroxypropylmethylcellulose, polyvinylpyrrolidone and the like.

Preferred examples of the disintegrants include lactose, sucrose, starch, carboxymethylcellulose, carboxymethylcellulose calcium, croscarmellose sodium, carboxymethylstarch sodium, low-substituted hydroxypropylcellulose and light silicic anhydride.

Preferred examples of the solvents include water for injection, physiological saline, Ringer's solution, alcohol, propylene glycol, polyethylene glycol, sesame oil, corn oil, olive oil and cotton seed oil.

Preferred examples of the solubilizers include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferred examples of the suspending agents include surfactants such as stearyltriethanolamine, sodium lauryl sulfate, laurylaminopropionic acid, lecithin, benzalkonium chloride, benzethonium chloride and glycerol monostearate; hydrophilic polymers such as polyvinyl alcohol, polyvinylpyrrolidone, carboxymethylcellulose sodium, methylcellulose, hydroxymethylcellulose, hydroxyethylcellulose and hydroxypropylcellulose; polysorbates, polyoxyethylene-hardened castor oil, and so forth.

Preferred examples of the isotonizing agents include sodium chloride, glycerol, D-mannitol, D-sorbitol and glucose.

Preferred examples of the buffers include buffer solutions of phosphate, acetate, carbonate and citrate.

Preferred examples of the local analgesics include benzyl alcohol and the like.

Preferred examples of the preservatives include para-hydroxybenzoate esters, chlorobutanol, benzyl alcohol, phenethyl alcohol, dehydroacetic acid and sorbic acid.

Preferred examples of the antioxidants include sulfite salts and ascorbate salts.

Preferred examples of the coloring agents include water-soluble colored tar dyes (e.g. food colors such as Food Color Red No. 2 and No. 3, Food Color Yellow No. 4 and No. 5, Food Color Blue No. 1 and No. 2), insoluble lake colors (e.g. the aluminum salt form of the above water-soluble edible tar colors), and natural colors (e.g. β-carotene, chlorophyll, iron oxide red).

Preferred examples of the sweeteners include saccharin sodium, dipotassium glycyrrhizinate, aspartame and stevia.

The compound of the present invention or a pharmaceutical preparation comprising the same (hereinafter referred to simply as "preparation of the invention") can be safely administered in the form of oral preparations such as tablets, capsules (including soft capsules and microcapsules), granules, powders, syrups, emulsions and suspensions; or of non-oral preparations such as injections (e.g. subcutaneous injection, intravenous injection, intramuscular injection, intraperitoneal injection), drip infusions, external application forms (e.g. nasal preparations, transdermal preparations, ointments), suppositories (e.g. rectal suppositories, vaginal suppositories), pellets, solutions for instillation, sustained-release preparations, eye drops, nasal drops, etc.

The preparation of the invention can be produced by the methods well established in fields of the pharmaceutical manufacturing techniques, for example by the methods described in the Japanese Pharmacopoeia. In the following, some typical methods for producing such preparations are described in detail.

An oral preparation, for instance, is produced by compression molding a mixture prepared by adding, to the active ingredient, an excipient, a disintegrant, a binder or a lubricant, for instance, if necessary followed by coating by a per se known method using a coating base for attaining taste masking, enteric coating or sustained release.

Examples of the coating base include a sugar coating base, a water-soluble film coating base, an enteric film coating base, or a sustained-release film coating base.

Useful as the sugar coating base is sucrose and, further, one or more ingredients selected from talc, precipitated calcium carbonate, gelatin, gum arabic, pullulan, carnauba wax and the like may be used in combination.

Examples of the water-soluble film coating base include cellulose polymers such as hydroxypropylcellulose, hydroxypropylmethylcellulose, hydroxyethylcellulose and methylhydroxyethylcellulose; synthetic polymers such as polyvinylacetal diethylaminoacetate, aminoalkyl methacrylate copolymer E [Eudragit E (trademark), Rhom Pharma] and polyvinylpyrrolidone; and polysaccharides such as pullulan.

Examples of the enteric film coating base include cellulose polymers such as hydroxypropylmethylcellulose phthalate, hydroxypropylmethylcellulose acetate succinate, carboxymethylethylcellulose, and cellulose acetate phthalate; acrylic acid polymers such as methacrylic acid copolymer L [Eudragit L (trademark), Rhom Pharma], methacrylic acid copolymer LD [Eudragit L-30D55 (trademark), Rhom Pharma] and methacrylic acid copolymer S [Eudragit S (trademark), Rhom Pharma]; and natural products such as shellac and the like.

Examples of the sustained-release film coating base include cellulose polymers such as ethylcellulose; acrylic acid polymers such as aminoalkyl methacrylate copolymer RS [Eudragit RS (trademark), Rhom Pharma] and an ethyl acrylate-methyl methacrylate copolymer suspension [Eudragit NE (trademark), Rhom Pharma]; and so forth.

Two or more of the above coating bases may be used in admixture in appropriate proportions. On the occasion of coating, a shading agent such as titanium oxide, red ferric oxide may be used.

Injections are produced by dissolving, suspending or emulsifying the active ingredient in an aqueous solvent (e.g. distilled water, physiological saline, Ringer's solution) or an oleaginous solvent (e.g. vegetable oils such as olive oil, sesame oil, cotton seed oil, corn oil; propylene glycol), together with a dispersant (e.g. polysorbate 80, polyoxyethylene-hardened castor oil 60), polyethylene glycol, carboxymethylcellulose, sodium alginate), a preservative (e.g. methylparaben, propylparaben, benzyl alcohol, chlorobutanol, phenol), an isotonizing agent (e.g. sodium chloride, glycerol, D-mannitol, D-sorbitol, glucose) and the like. If desirable, additives such as a solubilizer (e.g. sodium salicylate, sodium acetate), a stabilizer (e.g. human serum albumin), an analgesic (e.g. benzyl alcohol), may be used.

The content of compound (I) or a salt thereof in the preparation of the invention ranges, for instance, 0.1 to 100% by weight.

10) Dosage Etc.

The dose of the preparation of the invention may vary depending on the administration subject, route of administration, clinical conditions and other factors. Generally, however, in the case of oral administration to adults, the compound of the invention, which is the active ingredient, is administered in a single dose of about 0.05 to 500 mg/kg body weight, preferably about 0.5 to 100 mg/kg body weight. This dose is desirably administered once to three times a day.

When the preparation of the invention is orally administered to an adult patient suffering from peripheral neuropathy (e.g., diabetic neuropathy), the compound of the invention, which is the active ingredient, is administered in a single dose of about 0.05 to 50 mg/kg body weight, preferably 0.2 to 4 mg/kg body weight. This dose is desirably administered once to three times a day.

11) Action, Concomitant Drugs, etc.

The preparation of the invention has a neurotrophin (in particular NGF, BDNF, NT-3) production/secretion promoting activity.

The preparation of the invention also has an activity of improving a motor nerve conduction velocity and a sensory nerve conduction velocity.

The preparation of the invention scarcely produces side effects and can be used as a prophylactic/therapeutic agent for peripheral neuropathies (e.g. diabetic neuropathy, cancer therapy-induced neuropathy), a prophylactic/therapeutic agent for diabetic cardiomyopathy, a prophylactic/therapeutic agent for peripheral nerve injury, a prophylactic/therapeutic agent for spinal injury, a prophylactic/therapeutic agent for amyotrophic lateral sclerosis (ALS), a prophylactic/therapeutic agent for multiple sclerosis, a prophylactic/therapeutic agent for cerebral ischemic diseases, a prophylactic/therapeutic agent for senile dementia of Alzheimer type, a prophylactic/therapeutic agent for Parkinson's disease or Huntington's chorea, a prophylactic/therapeutic agent for depression, a prophylactic/therapeutic agent for inflammatory bowel disease, an ameliorating agent for peripheral neuropathies, or an ameliorating agent for cerebral metabolic disorders.

The preparation of the invention can also be used as a prophylactic/therapeutic agent for chronic pain (e.g., cancer pain, etc.), behavioural abnormalities accompanied by dementia (e.g. wandering, aggressiveness, etc.), anxiety, etc.

The preparation of the invention can also be used as a prophylactic/therapeutic agent for paresthesia or pain caused by wound, etc.

The preparation of the invention can also be used as an agent for preventing or treating diseases such as diabetes (e.g., insulin-dependent (type I) diabetes mellitus, noninsulin-dependent (type II) diabetes mellitus), impaired glucose tolerance, hyperlipidemia (e.g., hypertriglyceridemia, hypercholesterolemia, hypo-high-density-lipoproteinemia, postprandial hyperlipidemia, etc.), hyperinsulinemia, obesity, hyperphagia, hypertension, cardiovascular diseases (e.g., atherosclerosis, etc.); or syndromes (e.g., syndrome X, visceral fat obesity syndrome, etc.) having some of these diseases in combination.

The preparation of the invention possesses activity increasing depolarization-induced $Ca^{2+}$ influx, activity of NF (Nuclear Factor) κB inhibition, etc.

The preparation of the invention can be used in combination with a drug such as an antidiabetic, a therapeutic agent for diabetic complications, an antihyperlipidemic agent, an antihypertensive or hypotensive agent, an antiobesity agent, a diuretic agent, a chemotherapeutic agent, an immunotherapeutic agent and the like (hereinafter sometimes referred to briefly as "concomitant drug"). On such occasions, the time of administration of the preparation of the invention and that of the concomitant drug are not limited but they may be administered simultaneously or at staggered times to the administration subject. The dose of the concomitant drug can be appropriately selected based on the dose which is clinically employed. The proportion of the compound (I) or a salt thereof employed in the preparation of the invention and the concomitant drug can be appropriately selected according to the administration subject, administration route, target disease, clinical condition, combination, and other factors. In cases where the administration subject is human, for instance, the concomitant drug may be used in an amount of 0.01 to 100 parts by weight per part by weight of the compound (I) or a salt thereof.

Examples of the antidiabetic include insulin preparations (e.g. animal insulin preparations obtained by extraction from the bovine or swine pancreas; human insulin preparations synthesized by a genetic engineering technique using *Escherichia coli* or a yeast; insulin-zinc; protamine-insulin-zinc), insulin sensitizers (e.g. pioglitazone hydrochloride, troglitazone, rosiglitazone or its maleate, JTT-501, MCC-555, YM-440, GI-262570, KRP-297, FK-614, CS-011), α-glucosidase inhibitors (e.g. voglibose, acarbose, miglitol, emiglitate), biguanides (e.g. phenformin, metformin, buformin), sulfonylureas (e.g. tolbutamide, glibenclamide, gliclazide, chlorpropamide, tolazamide, acetohexamide, glyclopyramide, glimepiride), and other insulin secretagogues (e.g. repaglinide, senaglinide, mitiglinide or its calcium salt hydrate, GLP-1, nateglinide), dipeptidylpeptidase IV inhibitors (e.g. NVP-DPP-278, PT-100, P32/98), β3 agonists (e.g., CL-316243, SR-58611-A, UL-TG-307, AJ-9677, AZ40140), amyrin agonist (e.g. pramlintide), phosphotyrosine phosphatase inhibitors (e.g. vanadic acid), gluconeogenesis inhibitors (e.g. glycogen phosphorylase inhibitors, glucose-6-phosphatse inhibitors, glucagon antagonists), SGLT (sodium-glucose cotransporter) inhibitors (e.g. T-1095), etc.

Examples of the therapeutic agent for diabetic complications include aldose reductase inhibitors (e.g. tolrestat, epalrestat, zenarestat, zopolrestat, fidarestat(SNK-860), minalrestat(ARI-509), CT-112), neurotrophic factors (e.g. NGF, NT-3), AGE inhibitors (e.g. ALT-945, pimagedine, pyradoxamine, N-phenacylthiazolinium bromide(ALT-766), EXO-226), active oxygen scavengers (e.g. thioctic acid), cerebral vasodilators (e.g. tioburide), etc.

Examples of the antihyperlipidemic agent include statin compounds which are cholesterol synthesis inhibitors (e.g. pravastatin, simvastatin, lovastatin, atorvastatin, fluvastatin, cerivastatin or their salts (e.g., sodium salt)), squalene synthase inhibitors or fibrate compounds (e.g. bezafibrate, clofibrate, simfibrate, clinofibrate) having a triglyceride lowering action, etc.

Examples of the antihypertensive agent include angiotensin converting enzyme inhibitors (e.g. captopril, enalapril, delapril), angiotensin II antagonists (e.g. losartan, candesartan cilexetil), calcium antagonist (e.g., manidipine, nifedipine, amlodipine, efonidipine, nicardipine), clonidine, etc.

Examples of the antiobesity agent include antiobesity drugs acting on the central nervous system (e.g. dexfenfluramine, fenfluramine, phentermine, sibutramine, anfepramon, dexamphetamine, mazindol, phenylpropanolamine, clobenzorex), pancreatic lipase inhibitors (e.g. orlistat), β3 agonists (e.g. CL-316243, SR-58611-A, UL-TG-307, AJ-9677, AZ40140), anorectic peptides (e.g. leptin, CNTF (Ciliary Neurotrophic Factor)), cholecystokinin agonists (e.g. lintitript, FPL-15849), etc.

Examples of the diuretic agent include xanthine derivatives (e.g. theobromine and sodium salicylate, theobromine and calcium salicylate), thiazide preparations (e.g. ethiazide, cyclopenthiazide, trichlormethiazide, hydrochlorothiazide, hydroflumethiazide, benzylhydrochlorothiazide, penflutizide, polythiazide, methyclothiazide), antialdosterone preparations (e.g. spironolactone, triamterene), carbonate dehydratase inhibitors (e.g. acetazolamine), chlorobenzenesulfonamide preparations (e.g. chlorthalidone, mefruside, indapamide), azosemide, isosorbide, ethacrynic acid, piretanide, bumetanide, furosemide, etc.

Examples of the chemotherapeutic agent include alkylating agents (e.g. cyclophosphamide, ifosamide), metabolic antagonists (e.g. methotrexate, 5-fluorouracil), antitumor antibiotics (e.g. mitomycin, adriamycin), plant-derived antitumor agents (e.g. vincristine, vindesine, Taxol), cisplatin, carboplatin, etoposide, etc. Among these, 5-fluorouracil derivatives such as Furtulon and Neo-Furtulon are preferable.

Examples of the immunotherapeutic agent include microorganism- or bacterium-derived components (e.g. muramyl dipeptide derivatives, Picibanil), immunopotentiator polysaccharides (e.g. lentinan, schizophyllan, krestin), genetically engineered cytokines (e.g. interferons, interleukins (IL)), colony stimulating agents (e.g. granulocyte colony stimulating factor, erythropoietin), etc. Among these, IL-1, IL-2, IL-12 and the like are preferable.

Further, agents whose effects of ameliorating cachexia have been confirmed in animal models or clinically, namely cyclooxygenase inhibitors (e.g. indomethacin) (Cancer Research, vol. 49, pp. 5935-5939, 1989), progesterone derivatives (e.g. megestrol acetate) (Journal of Clinical Oncology, vol. 12, pp. 213-225, 1994), glucocorticoids (e.g. dexamethasone), metoclopramide pharmaceuticals, tetrahydrocannabinol pharmaceuticals (the above references are applied to both), fat metabolism ameliorating agents (e.g. eicosapentanoic acid) (British Journal of Cancer, vol. 68, pp. 314-318, 1993), growth hormones, IGF-1, and antibodies to the cachexia-inducing factor TNF-α, LIF, IL-6 or oncostatin M, can also be used in combination with the preparation of the invention.

Further, glycation inhibitors (e.g. ALT-711), nerve regeneration stimulators (e.g. Y-128, VX853, prosaptide), antidepressants (e.g. desipramine, amitriptyline, imipramine), anticonvulsant (e.g. lamotrigine), antiarrhythmics (e.g. mexiletine), acetylcholine receptor ligands (e.g. ABT-594), endothelin receptor antagonists (e.g. ABT-627), monoamine reuptake inhibitors (e.g. tramadol), narcotic analgesics (e.g. morphine), GABA receptor ligands (e.g. gabapentin), alpha-2 receptor ligands (e.g. clonidine), focal analgesics (e.g. capsaicin), protein kinase C inhibitors (e.g. LY-333531), anxiolytics (e.g. benzodiazepin), phosphodiesterase inhibitors (e.g. sildenafil), dopamine receptor ligands (e.g. apomorphine), etc. can be used in combination with the preparation of the invention.

Use of the preparation of the invention in combination with the above concomitant drug provides excellent effects such as effects of enhancing the action of the preparation of the invention or the concomitant drug, effects of reducing the dose of the preparation of the invention or the concomitant drug, effects of reducing the side effects of the action of the preparation of the invention or the concomitant drug, etc.

12) Methods of Producing Compounds

The compound (I) of the present invention can be produced by a per se known method. Examples of such methods include the methods described below or modifications thereof, and the methods described in JP Kokai S58-183676 (EP-A

Method A

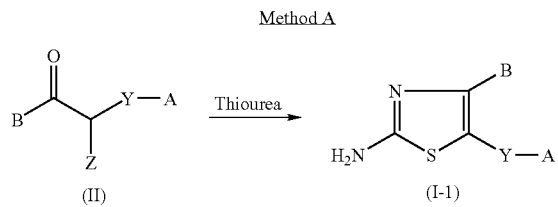

wherein Z represents a halogen atom and the other symbols have the same meanings as defined above.

The halogen atom for Z includes chlorine, bromine and iodine.

The desired compound (I-1) is produced by reacting the compound II) with thiourea. This reaction is carried out in the absence or presence of a solvent inert to the reaction. Examples of the solvent inert to the reaction include alcohols such as methanol and ethanol; aromatic hydrocarbons such as toluene and xylene; tetrahydrofuran, pyridine, N,N-dimethylformamide, dimethyl sulfoxide, acetic acid and water. Two or more of these solvents may be used in admixture in an appropriate ratio. This reaction may be carried out in the presence of a base as a deacidifying agent, and said base includes, for instance, organic amines such as triethylamine, N-methylmorpholine and N,N-dimethylaniline; sodium hydrogen carbonate, potassium carbonate, sodium carbonate, potassium acetate and sodium acetate. These bases are used in an amount of about 1 to 5 molar equivalents relative to compound II). The reaction temperature is normally about 0 to 200° C., preferably about 30 to 150° C. The reaction time is normally about 0.5 to 20 hours. The thus-obtained compound (I-1) can be isolated and purified by known separation/purification means such as concentration, concentration under reduced pressure, solvent extraction, crystallization, recrystallization, solvent substitution, chromatography, etc.

Method B

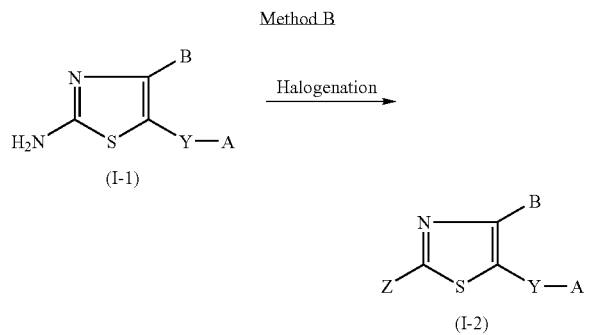

wherein the symbols have the same meanings as defined above.

The compound (I-2) is produced by conversion of the amino group of the compound (I-1). This reaction is carried out under the conditions of the per se known Sandmeyer reaction, namely in the presence of hydrochloric acid or hydrobromic acid in a solvent. Examples of the solvent include alcohols such as methanol and ethanol; ethers such as tetrahydrofuran and dioxane; aromatic amines such as quinoline and pyridine; acetone, dimethyl sulfoxide, phosphoric acid, acetic acid and water. Two or more of these solvents may be used in admixture in an adequate proportion. For the diazotization reaction, nitrous acid or a nitrite such as sodium nitrite is used as the diazotizing agent. A nitrosyl halide such as nitrosyl chloride may also be used. The amount of such diazotizing agents used is about 1 to 5 molar equivalents relative to compound (I-1). As the monovalent or divalent copper salt to be used in this reaction, there may be mentioned copper(I) chloride, copper(I) bromide, copper(I) iodide, copper(II) chloride, copper(II) bromide, copper(II) iodide, etc., and the amount of the salt used is about 1 to 5 molar equivalents relative to compound (I-1). The reaction temperature is normally about –20° C. to 200° C., preferably about 0° C. to 150° C. The reaction time is normally about 0.5 to 20 hours.

The reaction may also be carried out by reacting an alkyl nitrite in the presence of a monovalent or divalent copper salt in a solvent inert to the reaction. Examples of the solvent includes ethers such as tetrahydrofuran and dioxane; acetonitrile, acetone, dimethyl sulfoxide, etc. Two or more of these solvents may be used in admixture in an appropriate ratio. The monovalent or divalent copper salt to be used includes copper (I) chloride, copper(I) bromide, copper(I) iodide, copper(II) chloride, copper(II) bromide, copper(II) iodide, etc., and the amount of the salt used is about 1 to 5 molar equivalents relative to compound (1-1). Examples of the alkyl nitrite to be used include tert-butyl nitrite, isoamyl nitrite and the like, and the amount of the alkyl nitrite used is about 1 to 5 molar equivalents relative to compound (I-1). The reaction temperature is normally about –20° C. to 200° C., preferably about 0° C. to 150° C. The reaction time is normally about 0.5 to 20 hours. The thus-obtained compound (I-2) can be isolated and purified by known separation/purification means such as concentration, concentration under reduced pressure, solvent extraction, crystallization, recrystallization, solvent substitution, chromatography, etc.

Method C

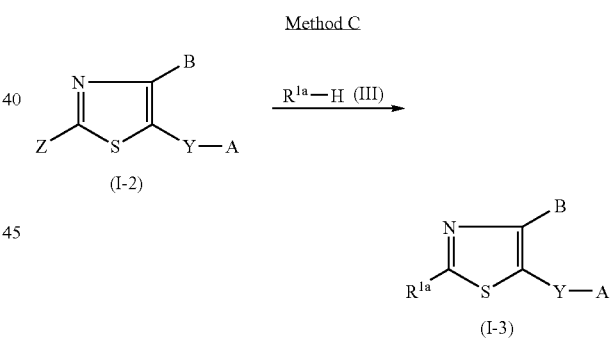

wherein the symbols have the same meanings as defined above.

The compound (I-3) is produced, for example, by reacting the compound (I-2) with the compound (III). This reaction is normally carried out in the presence of a base in a solvent inert to the reaction. When $R^{1a}$ in compound (III) is an amino group which may optionally be substituted, an excess of the compound (III) may be used as the solvent. Examples of the solvent inert to the reaction include alcohols such as methanol and ethanol; aromatic hydrocarbons such as toluene and xylene; ethers such as tetrahydrofuran and dioxane; N,N-dimethylformamide, dimethyl sulfoxide, acetone, acetonitrile and water. Two or more of these solvents may used in admixture in an appropriate ratio. Examples of the base include organic amines such as triethylamine, N-methylmorpholine and N,N-dimethylaniline; alkali metal salts such as potassium hydroxide, sodium hydroxide, lithium hydroxide, sodium hydrogen carbonate, potassium carbonate and sodium carbonate; metal hydrides such as sodium hydride; sodium methoxide and sodium ethoxide. The amount of compound (III) used is normally about 1 to 10 molar equivalents relative to compound (I-2). In cases where $R^{1a}$ in compound (III) is an amino group which may optionally be substituted, the amount of compound (III) used is normally about 1 to 50 molar equivalents relative to compound (I-2). When a base is used, the amount of the base used is normally about 1 to 5 molar equivalents relative to compound (I-2). The reaction temperature is normally about 0° C. to 200° C., preferably about 30° C. to 150° C. The reaction time is normally about 0.5 to 20 hours. The thus-obtained compound (1-3) can be isolated and purified by known separation/purification means such as concentration, concentration under reduced pressure, solvent extraction, crystallization, recrystallization, solvent substitution, chromatography, etc.

Method D

The compound of the formula (Ib) can be produced, for example, by subjecting a compound of the formula (IV):

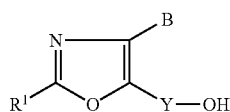

wherein the symbols have the same meanings as defined above, and a compound of the formula (V): H-$A^b$ wherein the symbol has the same meaning as defined above, to per se known Mitsunobu reaction.

This reaction is normally carried out in the presence of an organic phosphorous compound and an electrophilic agent in a solvent inert to the reaction.

Examples of the solvent inert to the reaction include halogenated hydrocarbons (e.g., dichloromethane, chloroform, 1,2-dichloroethane, 1,1,2,2-tetrachloroethane), aromatic hydrocarbons (e.g., benzene, toluene, xylene, chlorobenzene, nitrobenzene), ethers (e.g., diethyl ether, isopropyl ether, tetrahydrofuran, dioxane), N,N-dimethylformamide, N,N-dimethylacetamide, dimethyl sulfoxide. Two or more of these solvents may be used in admixture in an appropriate ratio. The solvents are preferably aromatic hydrocarbons or ethers, especially preferably toluene or tetrahydrofuran.

Examples of the organic phosphorous compound include triphenylphosphine, tributylphosphine.

Examples of the electrophilic agent include diethyl azodicarboxylate, diisopropyl azodicarboxylate, azodicarbonylpiperazine.

The amount of the organic phosphorous compound and the electrophilic agent used is normally about 1 to 5 equivalents relative to compound (IV). The reaction temperature is normally –50° C. to 150° C., preferably about –10° C. to 120° C. The reaction time is normally about 30 minutes to 20 hours.

The thus-obtained compound (Ib) can be isolated and purified by known separation/purification means such as concentration, concentration under reduced pressure, solvent extraction, crystallization, recrystallization, solvent substitution, chromatography, etc.

The material compounds and the desired compounds used in the above Methods A to D may form salts. Examples of such salts include those referred to as a salt of the above compound (I).

The above compounds (II), (III), (IV) and (V) can be produced in accordance with per se known methods (e.g., methods described in WO97/36882 or analogous methods thereto).

The following Examples are intended to describe the present invention in further detail and should by no means be construed as defining the scope of the invention. Unless mentioned otherwise, % means percent by weight. The room temperature means 1 to 30° C.

| Preparation Example 1 (Production of capsules) | |
|---|---|
| 1) Compound (1) | 30 mg |
| 2) Finely divided cellulose | 10 mg |
| 3) Lactose | 19 mg |
| 4) Magnesium stearate | 1 mg |
| Total | 60 mg |

1), 2), 3) and 4) are admixed and filled into a gelatin capsule.

| Preparation Example 2 (Production of tablets) | |
|---|---|
| 1) Compound (1) | 30 g |
| 2) Lactose | 50 g |
| 3) Corn starch | 15 g |
| 4) Carboxymethylcellulose calcium | 44 g |
| 5) Magnesium stearate | 1 g |
| 1000 tablets | 140 g |

The whole amounts of 1), 2) and 3) and 30 g of 4) are kneaded together with water and the mixture, after vacuum drying, is granulated. The granular mixture is admixed with 14 g of 4) and 1 g of 5) and the resulting mixture is tableted using a tableting machine, to give 1000 tablets each containing 30 mg of compound (1).

| Preparation Example 3 (Production of capsules) | |
|---|---|
| 1) Compound (5) | 30 mg |
| 2) Finely divided cellulose | 10 mg |
| 3) Lactose | 19 mg |
| 4) Magnesium stearate | 1 mg |
| Total | 60 mg |

1), 2), 3) and 4) are admixed and filled into a gelatin capsule.

| Preparation Example 4 (Production of tablets) | |
|---|---|
| 1) Compound (5) | 30 g |
| 2) Lactose | 50 g |
| 3) Corn starch | 15 g |
| 4) Carboxymethylcellulose calcium | 44 g |
| 5) Magnesium stearate | 1 g |
| 1000 tablets | 140 g |

The whole amounts of 1), 2) and 3) and 30 g of 4) are kneaded together with water and the mixture, after vacuum drying, is granulated. The granular mixture is admixed with 14 g of 4) and 1 g of 5) and the resulting mixture is tableted using a tableting machine, to give 1000 tablets each containing 30 mg of compound (5).

PREPARATION EXAMPLE 5

Production of Film-Coated Tablets

Production of a Coating Agent 209.6 g of hydroxypropylmethylcellulose 2910 (TC-5) and 42.0 g of Macrogol 6000 (polyethylene glycol 6000) were dissolved in 2520 g of purified water. In the solution thus obtained, 28.0 g of titanium oxide and 0.4 g of yellow ferric oxide were dispersed to give a coating agent.

Production of Plain Tablets

In a fluidized-bed granulating dryer (FD-3S, POWREX), 62.5 g of Compound (5), 3738 g of lactose and 750.0 g of corn starch were mixed uniformly. In the dryer, granulation was carried out while spraying an aqueous solution in which 150 g of hydroxypropylcellulose (HPC-L) was dissolved. Then, drying was carried out in the fluidized-bed granulating dryer.

The obtained granules were crushed by a Power-Mill pulverizer (P-3, Showa Machinery Co., Ltd.) with a punching screen of 1.5 mmϕ to give pulverized powders. To 4136 g of the pulverized powders, 220 g of croscarmellose sodium and 44 g of magnesium stearate were added, which was mixed in a tumble mixer (TM-15, Showa Machinery Co., Ltd.) to yield granules for tabletting. Plain tablets were obtained by tabletting the obtained granules with a rotary tabletting machine (Correct 19K, Kikusui Seisakusho Co., Ltd.) with a punch of 8.5 mmϕ at the weight of 200 mg (tabletting pressure: 7 KN/punch).

Production of Film-Coated Tablets

The above coating agent was sprayed onto the obtained plain tablets in a Driacoater coating machine (DRC-500, POWREX) to yield 19000 film-coated tablets having the following prescription and containing 2.5 mg of Compound (5) per tablet.

| Prescription of plain tablets (Composition per tablet) | |
|---|---|
| 1) Compound (5) | 2.5 mg |
| 2) Lactose | 149.5 mg |
| 3) Corn starch | 30.0 mg |
| 4) Croscarmellose sodium | 10.0 mg |
| 5) Hydroxypropylcellulose | 6.0 mg |
| 6) Magnesium stearate | 2.0 mg |
| Total | 200.0 mg |

| Prescription of film-coated tablets (Composition per tablet) | |
|---|---|
| 1) Plain tablet | 200.0 mg |
| (Film ingredients) | |
| 2) Hydroxymethylcellulose2910 | 5.24 mg |
| 3) Macrogol 6000 | 1.05 mg |
| 4) Titanium oxide | 0.7 mg |
| 5) Yellow ferric oxide | 0.01 mg |
| Total | 207.0 mg |

PREPARATION EXAMPLE 6

Production of Film-Coated Tablets 19000 film-coated tablets, having the following prescription and containing 15 mg of Compound (5) per tablet, were produced in the same manner as in Preparation Example 5 except that the amount of Compound (5) and lactose used was 375.0 g and 3425 g, respectively.

| Prescription of plain tablets (Composition per tablet) | |
|---|---|
| 1) Compound (5) | 25.0 mg |
| 2) Lactose | 137.0 mg |
| 3) Corn starch | 30.0 mg |
| 4) Croscarmellose sodium | 10.0 mg |
| 5) Hydroxypropylcellulose | 6.0 mg |
| 6) Magnesium stearate | 2.0 mg |
| Total | 200.0 mg |

| Prescription of film-coated tablets (Composition per tablet) | |
|---|---|
| 1) Plain tablet | 200.0 mg |
| (Film ingredients) | |
| 2) Hydroxypropylcellulose2910 | 5.24 mg |
| 3) Macrogol 6000 | 1.05 mg |
| 4) Titanium oxide | 0.7 mg |
| 5) Yellow ferric oxide | 0.01 mg |
| Total | 207.0 mg |

PREPARATION EXAMPLE 7

Production of Film-Coated Tablets 19000 film-coated tablets, having the following prescription and containing 60 mg of Compound (5) per tablet, were produced in the same manner as in Preparation Example 5 except that the amount of Compound (5) and lactose used was 1500.0 g and 2300 g, respectively.

| Prescription of plain tablets (Composition per tablet) | |
|---|---|
| 1) Compound (5) | 60.0 mg |
| 2) Lactose | 92.0 mg |
| 3) Corn starch | 30.0 mg |
| 4) Croscarmellose sodium | 10.0 mg |
| 5) Hydroxypropylcellulose | 6.0 mg |
| 6) Magnesium stearate | 2.0 mg |
| Total | 200.0 mg |

| Prescription of film-coated tablets (Composition per tablet) | |
|---|---|
| 1) Plain tablet | 200.0 mg |
| (Film ingredients) | |
| 2) Hydroxymethylcellulose2910 | 5.24 mg |
| 3) Macrogol 6000 | 1.05 mg |
| 4) Titanium oxide | 0.7 mg |
| 5) Yellow ferric oxide | 0.01 mg |
| Total | 207.0 mg |

REFERENCE EXAMPLE 1A CULTIVATION OF SCHWANN CELLS

Schwann cells were prepared by subjecting the dorsal spinal root ganglion collected from 10 newborn SD rats to enzyme treatment using 0.25% trypsin containing 0.01% deoxyribonuclease (DNase, produced by Sigma), followed by cloning from the cell group obtained. Thus, cells were distributed into poly-L-lysine-coated petri dishes 60 mm in diameter and incubated in minimum essential media containing 10% fetal calf serum (FCS), 0.5% glucose, 20 µg/ml gentamicin and 2.5 µg/ml amphotericin B. After 3 days of incubation, the media were replaced with the same ones supplemented with the DNA synthesis inhibitor cytosine arabinoside, followed by two more days of incubation, to remove fibroblasts showing rapid growth. Then, the medium was replaced with a fresh one prepared by supplementing with 50 µg/ml of a bovine hypophysis extract (produced by Sigma) and $10^{-5}$ M forskolin (produced by Sigma) in lieu of $10^{-5}$ M DNA synthesis inhibitor, to thereby activate proliferation of Schwann cells. The thus-obtained Schwann cells were cultured using Dulbecco's modified Eagle medium (DMEM) supplemented with 10% FCS. Thus, Schwann cells were distributed onto poly-L-lysine-coated 48-well plates and cultured in a carbon dioxide incubator (37° C., 5% carbon dioxide) until confluence. After medium removal, cells were washed with DMEM containing 0.5% bovine serum albumin (Fraction V, produced by Sigma). DMEM supplemented with 0.5% bovine serum albumin and containing a predetermined concentration of the test compound was added to Schwann cells. The Schwann cells were cultured in a carbon dioxide incubator for 24 hours.

EXPERIMENTAL EXAMPLE 1

Neurotrophin Production/Secretion Promoting Activity

The culture fluid obtained in each run of Reference Example 1A was recovered and assayed for the neurotrophin content therein. NGF was assayed by the enzyme immunoassay method described by Murase et al. in Biochemistry International, vol. 22, p. 807 (1990). Thus, an anti-NGF antibody (100 µg/ml) (antibody obtained by using mouse NGF as the antigen and immunizing New Zealand albino rabbits therewith) was distributed in 10-µl portions in the wells of 96-well round bottom plates and antibody adsorption was allowed to proceed by 2 hours standing at room temperature. After removing the antibody, each well was washed three times with a washing solution. A 10-µl portion of the above recovered culture fluid or standard NGF solution was placed in each well and the plates were allowed to stand at room temperature for 2.5 hours. After three times washings of each well, 20 µl of biotinylated anti-NGF antibody (35 ng/ml) was added thereto, followed by overnight standing at 4° C. The biotinylated anti-NGF antibody was prepared by adding D-biotinyl-ε-aminocaproic acid N-hydroxysuccinimide ester (0.48 mg/µl, produced by Boehringer Mannheim) to IgG (35 µg/100 µl), allowing the reaction to proceed at room temperature for 2 hours and then terminating the reaction with 100 µl of 1 M Tris-hydrochloride buffer (pH 8.0). After washing the biotinylated anti-NGF antibody, 20 µl of β-D-galactosidase-labeled streptoavidin (produced by Boehringer Mannheim) was added, and the mixture was allowed to stand at room temperature for 1 hour. After washing, 30 µl of 4-methylumbelliferyl-β-D-galactoside (produced by Sigma) (10 µg/µl) was added to the substrate, the reaction was allowed to proceed at room temperature for 4 hours and then terminated by addition of 130 µl of 0.1 M glycine-sodium hydroxide buffer (pH 10.3), and the fluorescent intensity of the 4-methylumbelliferone produced was determined (Ex: 360 nm; Em: 450 nm). The amount of NGF was calculated based on a standard curve and expressed in terms of relative multiplicity in relation to the amount of NGF (control) produced and secreted by cells treated in the same manner without adding the test compound. BDNF was assayed in the same manner as in NGF assaying, using an anti-BDNF antibody (produced by Promega) and standard BDNF (produced by Peprotech).

Compounds (1) and (5) showed excellent NGF and BDNF production/secretion promoting activity at concentrations of $10^{-4}$ M to $10^{-8}$ M.

EXPERIMENTAL EXAMPLE 2

Neurotrophin Production/Secretion Promoting Activity in Rat Peripheral and Brain Tissues A diabetic neuropathy model was made by injecting streptozotocin (STZ) into the tail vein of male 6-week-old SD rats in a dose of 70 mg/kg body weight. After 4 weeks, 0.1 to 3 mg/kg body weight of compound (5) was orally administered for 4 weeks, and each tissue was collected. The collected tissue was supplemented with 25 to 40 times of disruption buffer (0.1 M Tris-hydrochloride buffer, pH 7.6, containing 1 M sodium chloride, 2% BSA, 2 mM EDTA, 80 trypsin units/L of aprotinin and 0.02% sodium azide) in terms of the wet tissue weight, which was subjected to sonication. After 30 minutes of centrifugation at 15,000 rpm, the supernatant was used as the sample and the NGF and BDNF contents were determined in the same manner as in Experimental Example 1.

Compound (5) showed excellent NGF and BDNF production/secretion promoting activity at such sites as the sciatic nerve and the hippocampus. The results are shown in Table 1.

TABLE 1

| Treatment | BDNF (ng/g tissue) | | NGF (pg/g tissue) | |
|---|---|---|---|---|
| | Sciatic nerve | Hippo-campus | Sciatic nerve | Hippo-campus |
| No treatment | 6.0 ± 1.1* | 3.4 ± 0.6* | 430 ± 127 | 621 ± 166 |
| Group dosed with STZ | 3.7 ± 0.9 | 2.7 ± 0.5 | 282 ± 173 | 524 ± 107 |
| Group dosed with STZ + compound (5) | 5.0 ± 0.6* | 3.5 ± 0.3* | 495 ± 143* | 738 ± 105* |

Mean ± SD (n = 8 to 9)
*: $p < 0.05$ vs STZ group (t-test)

EXPERIMENTAL EXAMPLE 3

A diabetic neuropathy model was made by injecting streptozotocin (STZ) into the tail vein of male 6-week-old SD rats in a dose of 70 mg/kg body weight. After 4 moths of housing, 10 mg/kg body weight/day of compound (5) which was suspended in 0.5% (w/v) methylcellulose was orally administered for 4 months. After administration, the rats were anesthetized with pentobarbital and the body temperature of the rats were kept 37° C. using a hotplate heated and an electric lamp.

Then, conduction velocities of motor nerves and sensory nerves were determined using an induction potential test device (Neuropack 2, produced by Nihon Kohden) in the following manner.

Determination of a Motor Nerve Conduction Velocity

Needle electrodes were placed at the thigh or the ankle of the rats. Then, the sciatic nerve or the tibial nerve was stimulated at, in principle, 1.6 mA and the action potential was recorded from the plantar muscle. The motor nerve conduction velocity was calculated from the distance and latencies of the two different stimulating sites.

Determination of a Sensory Nerve Conduction Velocity

Proximal or distal positions of the sural nerve of the rats were stimulated at, in principle, 0.8 mA and the potential was recorded at the plantar skin. The sensory nerve conduction velocity was calculated from the distance and latencies of the two different stimulating sites.

The results are shown in Table 2. In the table, MNCV and SVCV represent motor nerve conduction velocity and sensory nerve conduction velocity, respectively.

TABLE 2

| Treatment | MNCV (m/s) | SNCV (m/s) |
|---|---|---|
| No treatment | 53.2 ± 4.9## | 40.7 ± 5.5## |
| Group dosed with STZ | 38.6 ± 3.5 | 29.9 ± 2.5 |
| Group dosed with STZ + compound (5) | 54.9 ± 7.6** | 41.1 ± 7.9** |

Mean ± SD (n = 5 to 8)
**: $p < 0.01$ vs STZ group (Dunnet's test)
: $p < 0.01$ vs STZ group (t-test)

As shown in Table 2, the conduction velocities of motor nerve and sensory nerve were lowered in the group dosed with STZ as compared with the normal group. However, in the group dosed with compound (5), these nerve conduction velocities were recovered.

EXPERIMENTAL EXAMPLE 4

A diabetic neuropathy model was made by injecting streptozotocin (STZ) into the tail vein of male 6-week-old SD rats in a dose of 70 mg/kg body weight. After 4 months of housing, 10 mg/kg body weight/day of compound (5) which was suspended in 0.5% (w/v) methylcellulose was orally administered for 1 month. After administration, a hvderalgesia test was conducted using a pressure-stimulant algesiometer (produced by Ugo Basil) to determine the pain threshold of hindlimb.

While, the pons were collected from brain stem to determine the contents of neurotrophic factors. The BDNF contents were determined in the similar manner as in Experimental Example 2. The NT-3 contents were determined in the similar manner as in Experimental Example 2 except that an anti-NT-3 antibody (Brain Res. 1994, 12, pp. 143-146; Clin Chim Acta 1994, 227, pp. 23-36) was used.

The results are shown in Tables 3 and 4.

TABLE 3

| Treatment | Pain threshold (g) |
|---|---|
| No treatment | 117 ± 8## |
| Group dosed with STZ | 74 ± 8 |
| Group dosed with STZ + compound (5) | 109 ± 19** |

Mean ± SD (n = 10)
**: $p < 0.01$ vs STZ group (Dunnet's test)
: $p < 0.01$ vs STZ group (t-test)

TABLE 4

| Treatment | BDNF (pg/g tissue) | NT-3 (pg/g tissue) |
|---|---|---|
| No treatment | 3209 ± 883## | 323 ± 64## |
| Group dosed with STZ | 1447 ± 794 | 215 ± 58 |
| Group dosed with STZ + compound (5) | 4151 ± 1161** | 352 ± 118** |

Mean ± SD (n = 10)
**: $p < 0.01$ vs STZ group (Dunnet's test)
: $p < 0.01$ vs STZ group (t-test)

As shown in Table 3, the pain threshold was lowered in the group dosed with STZ as compared with the normal group, which showed hyperalgesia. However, in the group dosed with compound (5), hyperalgesia was ameliorated.

As shown in Table 4, the amounts of BDNF and NT-3 in pons were lowered in the group dosed with STZ as compared with the normal group. However, in the group dosed with compound (5), these amounts were increased.

EXAMPLE 1

To a mixture of 4-(4-chlorophenyl)-2-(2-methyl-1-imidazolyl)-5-oxazolepropanol (500 mg), 2-methylphenol (340 mg), tributylphosphine (640 mg) and tetrahydrofuran (20 ml) was added dropwise a toluene solution of diethyl azodicarboxylate (40%, 1.37 g) at room temperature, and the resulting mixture was stirred for 5 hours at the same temperature. After the reaction mixture was concentrated, the residue was subjected to silica gel column chromatography, and crystals of 4-(4-chlorophenyl)-2-(2-methyl-1-imidazolyl)-5-[3-(2-methylphenoxy)propyl]oxazole (385 mg, 60%) were obtained from an ethyl acetate-hexane (2:3, v/v)-eluted fraction. They were recrystallized from acetone-isopropyl ether. Colorless prisms. Melting point 110-111° C. NMR (CDCl$_3$) δ: 2.15-2.35 (2H, m), 2.24 (3H, s), 2.75 (3H, s), 3.18 (2H, t, J=7.5 Hz), 4.06 (2H, t, J=5.5 Hz), 6.76 (1H, d, J=8 Hz), 6.87 (1H, t, J=7.5 Hz), 6.99 (1H, d, J=1.5 Hz), 7.05-7.2 (2H, m), 7.34 (2H, d, J=8.5 Hz), 7.41 (1H, d, J=1.5 Hz), 7.61 (2H, d, J=8.5 Hz).

EXAMPLE 2

To a mixture of 4-(4-chlorophenyl)-2-(2-methyl-1-imidazolyl)-5-oxazolepropanol (500 mg), 4-methoxyphenol (390 mg), tributylphosphine (640 mg) and tetrahydrofuran (20 ml) was added dropwise a toluene solution of diethyl azodicarboxylate (40%, 1.37 g) at room temperature, and the resulting mixture was stirred for 3 hours. After the reaction mixture was concentrated, the residue was subjected to silica gel column chromatography, and crystals of 4-(4-chlorophenyl)-5-[3-(4-methoxylphenoxy)propyl]-2-(2-methyl-1-imidazolyl)oxazole (490 mg, 73%) were obtained from an ethyl acetate-hexane (2:3, v/v)-eluted fraction. They were recrystallized from isopropyl ether-hexane. Colorless needles. Melting point 53-54° C.

EXAMPLE 3

To a mixture of 4-(4-chlorophenyl)-2-(2-methyl-1-imidazolyl)-5-oxazolepropanol (500 mg), 3-methoxyphenol (390 mg), tributylphosphine (640 mg) and tetrahydrofuran (20 ml) was added dropwise a toluene solution of diethyl azodicarboxylate (40%, 1.37 g) at room temperature, and the resulting mixture was stirred for 3 hours. After the reaction mixture was concentrated, the residue was subjected to silica gel column chromatography, and 4-(4-chlorophenyl)-5-[3-(3-methoxylphenoxy)propyl]-2-(2-methyl-1-imidazolyl)oxazole (470 mg, 70%) was obtained as an oil from an ethyl acetate-hexane (2:3, v/v)-eluted fraction.

NMR (CDCl$_3$) δ: 1.9-2.1 (4H, m), 2.77 (3H, s), 3.02 (2H, t, J=7.5 Hz), 3.82 (3H, s), 4.06 (2H, t, J=6 Hz), 6.85-6.95 (4H, m), 7.00 (1H, d, J=1.5 Hz), 7.37 (2H, d, J=8.5 Hz), 7.46 (1H, d, J=1.5 Hz), 7.61 (2H, d, J=8.5 Hz)

EXAMPLE 4

To a mixture of 4-(4-chlorophenyl)-2-(2-methyl-1-imidazolyl)-5-oxazolepropanol (500 mg), 2-ethoxyphenol (435 mg), tributylphosphine (640 mg) and tetrahydrofuran (20 ml) was added dropwise a toluene solution of diethyl azodicarboxylate (40%, 1.37 g) at room temperature, and the resulting mixture was stirred for 18 hours. After the reaction mixture was concentrated, the residue was subjected to silica gel chromatography and crystals of 4-(4-chlorophenyl)-5-[3-(2-ethoxylphenoxy)propyl]-2-(2-methyl-1-imidazolyl)oxazole were obtained from an ethyl acetate-hexane (2:3, v/v)-eluted fraction. Recrystallization from ethyl acetate-hexane gave 390 mg (57%) of colorless needles. Melting point 96-97° C.

EXAMPLE 5

To a mixture of 4-(4-chlorophenyl)-2-(2-methyl-1-imidazolyl)-5-oxazolebutanol (300 mg), 2-methoxyphenol (340 mg), tributylphosphine (550 mg) and tetrahydrofuran (15 ml) was added dropwise a toluene solution of diethyl azodicarboxylate (40%, 1.18 g) at room temperature, and the resulting mixture was stirred for 24 hours. After the reaction mixture was concentrated, the residue was subjected to silica gel column chromatography, and crystals of 4-(4-chlorophenyl)-5-[4-(2-methoxylphenoxy)butyl]-2-(2-methyl-1-imidazolyl)oxazole (275 mg, 69%) were obtained from an ethyl acetate-hexane (2:3, v/v)-eluted fraction. They were recrystallized from ethyl acetate-isopropyl ether. Colorless needles. Melting point 72-73° C.

EXAMPLE 6

To a mixture of 4-(5-chloro-2-thienyl)-2-(2-methyl-1-imidazolyl)-5-oxazolebutanol (670 mg), methyl 4-hydroxybenzoate (320 mg), triphenylphosphine (551 mg) and tetrahydrofuran (10 ml) was added dropwise a toluene solution of diethyl azodicarboxylate (40%, 957 mg) at room temperature, and the resulting mixture was stirred for 2 hours. After the reaction mixture was concentrated, the residue was subjected to silica gel column chromatography, and crystals of methyl 4-[4-[4-(5-chloro-2-thienyl)-2-(2-methyl-1-imidazolyl)-5-oxazolyl]butoxy]benzoate (520 mg, 51%) were obtained from an ethyl acetate-hexane (1:1, v/v)-eluted fraction. They were recrystallized from ethyl acetate-isopropyl ether. Colorless prisms. Melting point 111-112° C.

EXAMPLE 7

To a mixture of 4-(5-chloro-2-thienyl)-2-(2-methyl-1-imidazolyl)-5-oxazolebutanol (500 mg), 4-cyanophenol (192 mg), triphenylphosphine (505 mg) and tetrahydrofuran (10 ml) was added dropwise a toluene solution of diethyl azodicarboxylate (40%, 836 mg) at room temperature, and the resulting mixture was stirred for 2 hours. After the reaction mixture was concentrated, the residue was subjected to silica gel column chromatography, and crystals of 4-(5-chloro-2-thienyl)-5-[4-(4-cyanophenoxy)butyl]-2-(2-methyl-1-imidazolyl)oxazole (650 mg) were obtained from an ethyl acetate-hexane (1:1, v/v)-eluted fraction. They were recrystallized from ethyl acetate-isopropyl ether to give pale yellow prisms (430 mg, 66%). Melting point 110-114° C.

EXAMPLE 8

A mixture of 4-[4-(5-chloro-2-thienyl)-2-(2-methyl-1-imidazolyl)-5-oxazolyl]butyl methanesulfonate (350 mg), 4-chlorophenol (259 mg), anhydrous potassium carbonate (276 mg) and N,N-dimethylformamide (5 ml) was stirred at 85-90° C. for 2 hours. The reaction mixture was diluted with 100 ml of ethyl acetate, and the resultant was washed with 100 ml of water and dried over anhydrous magnesium sulfate. After the organic layer was concentrated, the residue was subjected to silica gel column chromatography, and crystals of 5-[4-(4-chlorophenoxy)butyl]-4-(5-chloro-2-thienyl)-2-(2-methyl-1-imidazolyl)oxazole were obtained from an ethyl acetate-hexane (1:1, v/v)-eluted fraction and recrystallized from ethyl acetate-isopropyl ether to give pale yellow prisms (175 mg, 50%). Melting point 81-82° C.

EXAMPLE 9

To a mixture of 4-(4-chlorophenyl)-2-(2-methyl-1-imidazolyl)-5-oxazolebutanol (3.32 g), methyl 4-hydroxybenzoate (2.28 g), triphenylphosphine (3.93 g) and tetrahydrofuran (50 ml) was added dropwise a toluene solution of diethyl azodicarboxylate (40%, 6.53 g) at room temperature, and the resulting mixture was stirred for 1 hour. After the reaction mixture was concentrated, the residue was subjected to silica gel column chromatography, and crystals of methyl 4-[4-[4-(4-chlorophenyl)-2-(2-methyl-1-imidazolyl)-5-oxazolyl]butoxy]benzoate were obtained from an ethyl acetate-hexane (1:1, v/v)-eluted fraction and recrystallized from ethyl acetate-isopropyl ether to give colorless needles (3.81 g, 82%). Melting point 106-108° C.

EXAMPLE 10

To a mixture of methyl 4-[4-[4-(4-chlorophenyl)-2-(2-methyl-1-imidazolyl)-5-oxazolyl]butoxy]benzoate (930 mg) and tetrahydrofuran (10 ml) was added gradually lithium aluminum hydride (76 mg) under ice-cooling, and the resulting mixture was stirred for 1 hour. To the reaction mixture was carefully added 0.3 ml of water, the mixture was filtered, and the residue on the filter paper was washed with ethyl acetate. After the filtrate was concentrated and isopropyl ether was added to the residue, crystals of 4-(4-chlorophenyl)-5-[4-(4-hydroxymethylphenoxy)butyl]-2-(2-methyl-1-imidazolyl)oxazole (750 mg, 86%) were obtained. Recrystallization from ethyl acetate-isopropyl ether gave colorless prisms. Melting point 106-107° C.

EXAMPLE 11

To a mixture of methyl 4-[4-[4-(4-chlorophenyl)-2-(2-methyl-1-imidazolyl)-5-oxazolyl]butoxy]benzoate (1.86 g), tetrahydrofuran (20 ml) and ethanol (10 ml) was added 15 ml of a 1 N aqueous solution of sodium hydroxide, and the resulting mixture was stirred at 60-65° C. for 3 hours. The reaction mixture was concentrated and then diluted with a 10% aqueous solution of citric acid, and the resulting precipitate was filtered, washed with water and air-dried to give crystals of 4-[4-(4-chlorophenyl)-2-(2-methyl-1-imidazolyl)-5-oxazolyl]butoxy]benzoic acid. Recrystallization from tetrahydrofuran-isopropyl ether gave colorless prisms (1.15 g, 51%). Melting point 214-216° C.

EXAMPLE 12

A mixture of 3-[4-(4-chlorophenyl)-2-(2-methyl-1-imidazolyl)-5-oxazolyl]propyl methanesulfonate (800 mg), 4-trifluoromethoxyphenol (713 mg), anhydrous potassium carbonate (553 mg) and N,N-dimethylformamide (10 ml) was stirred at 85-90° C. for 2 hours. The reaction mixture was poured into 100 ml of water and extracted with ethyl acetate (100 ml×3). The organic layer was washed with a 0.5 N aqueous solution of sodium hydroxide (50 ml×2) and water (100 ml), and dried over anhydrous magnesium sulfate. After the organic layer was concentrated, the residue was subjected to silica gel column chromatography, and crystals of 4-(4-chlorophenyl)-2-(2-methyl-1-imidazolyl)-5-[3-(4-trifluoromethoxyphenoxy)propyl]oxazole were obtained from an ethyl acetate-hexane (1:1, v/v)-eluted fraction. Recrystallization from ethyl acetate-isopropyl ether gave pale yellow prisms (594 mg, 61%). Melting point 85-86° C.

EXAMPLE 13

A mixture of 3-[4-(4-chlorophenyl)-2-(2-methyl-1-imidazolyl)-5-oxazolyl]propyl methanesulfonate (800 mg), 4-cyanophenol (477 mg), anhydrous potassium carbonate (553 mg) and N,N-dimethylformamide (10 ml) was stirred at 85-90° C. for 2 hours. The reaction mixture was poured into 100 ml of water and extracted with ethyl acetate (100 ml×3). The organic layer was washed with a 0.5 N aqueous solution of sodium hydroxide (50 ml×2) and water (100 ml) and dried over anhydrous magnesium sulfate. After the organic layer was concentrated, the residue was subjected to silica gel column chromatography, and crystals of 4-(4-chlorophenyl)-5-[3-(4-cyanophenoxy)propyl]-2-(2-methyl-1-imidazolyl) oxazole were obtained from an ethyl acetate-hexane (1:1, v/v)-eluted fraction. Recrystallization from ethyl acetate-isopropyl ether gave pale yellow prisms (700 mg, 84%). Melting point 93-94° C.

EXAMPLE 14

A mixture of 3-[4-(4-chlorophenyl)-2-(2-methyl-1-imidazolyl)-5-oxazolyl]propyl methanesulfonate (1.05 g), 4-trifluoromethylphenol (650 mg), anhydrous potassium carbonate (574 mg) and N,N-dimethylformamide (10 ml) was stirred at 85-90° C. for 2 hours. The reaction mixture was poured into water (100 ml) and extracted with ethyl acetate (100 ml×3). The organic layer was washed with a 0.5 N aqueous solution of sodium hydroxide (50 ml×2) and water (100 ml) and dried over anhydrous magnesium sulfate. After the organic layer was concentrated, the residue was subjected to silica gel column chromatography, and crystals of 4-(4-chlorophenyl)-2-(2-methyl-1-imidazolyl)-5-[3-(4-trifluoromethylphenoxy)propyl]oxazole were obtained from an ethyl acetate-hexane (3:2, v/v)-eluted fraction. Recrystallization from ethyl acetate-isopropyl ether gave pale yellow prisms (299 mg, 24%). Melting point 80-82° C.

EXAMPLE 15

To a mixture of 4-(5-chloro-2-thienyl)-2-(2-methyl-1-imidazolyl)-5-oxazolebutanol (170 mg), 2-methoxyphenol (124 mg), tributylphosphine (202 mg) and tetrahydrofuran (5 ml) was added dropwise a toluene solution of diethyl azodicarboxylate (40%, 435 mg) at room temperature, and the resulting mixture was stirred for 14 hours. After the reaction mixture was concentrated, the residue was subjected to silica gel column chromatography, and crystals of 4-(5-chloro-2-thienyl)-2-(2-methyl-1-imidazolyl)-5-[3-(2-methoxyphenoxy)propyl]oxazole were obtained from an ethyl acetate-hexane (1:1, v/v)-eluted fraction. Recrystallization from ethyl acetate-hexane gave colorless prisms (64 mg, 29%). Melting point 81-82° C.

EXAMPLE 16

A mixture of ethyl 2-chloro-4-(5-chloro-2-thienyl)-5-oxazolebutanoate (1.50 g), powdered zinc (4.50 g) and acetic acid (30 ml) was stirred with heating under reflux for 1 hour. The insoluble material was filtered off, and the filtrate was concentrated. The residue was diluted with 100 ml of a saturated aqueous solution of sodium hydrogen carbonate, and extracted with ethyl acetate (50 ml×3). The organic layer was dried over anhydrous magnesium sulfate and then concentrated to give 1.18 g of an oil. This oil was dissolved in tetrahydrofuran (10 ml), to which was added gradually lithium aluminum hydride (127 mg) under ice-cooling, and the resulting mixture was stirred for 1 hour. Water (0.5 ml) was carefully added to the reaction mixture, the resulting mixture was filtered, and the residue on the filter paper was washed with ethyl acetate. The filtrate was concentrated to give 4-(5-chloro-2-thienyl)-5-oxazolebutanol as an oil (800 mg, 69%).

NMR (CDCl$_3$): 1.5-1.9 (5H, m), 2.91 (2H, t, J=7.0 Hz), 3.69 (2H, t, J=6 Hz), 6.89 (1H, d, J=3.5 Hz), 7.05 (1H, d, J=3.5 Hz), 7.76 (1H, s)

EXAMPLE 17

To a mixture of 4-(5-chloro-2-thienyl)-5-oxazolebutanol (800 mg), 2-methoxyphenol (770 mg), tributylphosphine (1.24 g) and tetrahydrofuran (10 ml) was added dropwise a toluene solution of diethyl azodicarboxylate (40%, 2.61 g) at room temperature, and the resulting mixture was stirred for 1 hour. After the reaction mixture was concentrated, the residue was subjected to silica gel column chromatography, and 4-(5-chloro-2-thienyl)-5-[4-(2-methoxyphenoxy)butyl]oxazole was obtained as an oil (420 mg, 37%) from an ethyl acetate-hexane (1:4, v/v)-eluted fraction.

NMR (CDCl$_3$) δ: 1.8-2.0 (4H, m), 2.96 (2H, t, J=7.0 Hz), 3.85 (3H, s), 4.05 (2H, t, J=6 Hz), 6.85-6.95 (5H, m), 7.04 (1H, d, J=4.5 Hz), 7.76 (1H, s)

EXAMPLE 18

A mixture of ethyl 5-bromo-5-(5-chloro-2-thiophencarbonyl)valerate (1.46 g), thiourea (0.64 g) and ethanol (10 ml) was stirred with heating under reflux for 2 hours. The reaction mixture was poured into 100 ml of water and extracted with ethyl acetate (100 ml×2). The organic layer was dried over anhydrous magnesium sulfate and concentrated to give 1.30 g of a yellow solid. This solid was dissolved in acetic acid (20 ml), to which was added 2,5-dimethoxytetrahydrofuran (518 mg). The mixture was stirred with heating under reflux for 1 hour. The reaction mixture was diluted with a 10% aqueous solution of sodium hydrogen carbonate (100 ml) and extracted with ethyl acetate (100 ml×2). The organic layer was dried over anhydrous magnesium sulfate and then concentrated to give 1.40 g of a yellow oil. This oil was dissolved in tetrahydrofuran (10 ml), to which was added gradually lithium aluminum hydride (152 mg) under ice-cooling. The mixture was stirred for 1 hour. Water (0.5 ml) was carefully added to the reaction mixture, the resulting mixture was filtered, and the residue on the filter paper was washed with ethyl acetate. The filtrate was concentrated to give 1.08 g of a yellow oil. To a mixture of this oil (1.08 g), 2-methoxyphenol (745 mg), tributylphosphine (1.20 g) and tetrahydrofuran (20 ml) was added a toluene solution of diethyl azodicarboxylate (40%, 2.61 g) at room temperature, and the resulting mixture was stirred for 1 hour. After the reaction mixture was concentrated, the residue was subjected to silica gel column chromatography, and crystals of 4-(5-chloro-2-thienyl)-5-[4-(2-methoxyphenoxy)butyl]-2-(1-pyrrolyl)thiazole were obtained from an ethyl acetate-hexane (1:4, v/v)-eluted fraction. Recrystallization from ethyl acetate-hexane gave pale yellow prisms (584 mg, 4-step overall yield 32%). Melting point 77-78° C.

EXAMPLE 19

To a mixture of 4-(4-chlorophenyl)-2-(1-imidazolyl)-5-oxazolepropanol (600 mg), 2-methoxyphenol (500 mg), tributylphosphine (800 mg) and tetrahydrofuran (10 ml) was added dropwise a toluene solution of diethyl azodicarboxylate (40%, 1.74 g) at room temperature, and the resulting mixture was stirred for 1 hour. After the reaction mixture was concentrated, the residue was subjected to silica gel column chromatography, and crystals of 4-(4-chlorophenyl)-2-(1-imidazolyl)-5-[3-(2-methoxyphenoxy)propyl]oxazole (272 mg, 34%) were obtained from an ethyl acetate-hexane (1:1, v/v)-eluted fraction. Recrystallization from ethyl acetate-hexane gave colorless prisms. Melting point 109-110° C.

EXAMPLE 20

A mixture of 4-(4-chlorophenyl)-2-(1-pyrazolyl)-5-oxazolepropanol (1.02 g), 2-methoxyphenol (1.20 g), cyanomethylenetributylphosphorane (2.0 g, produced by Tokyo Kasei) and tetrahydrofuran (20 ml) was stirred in a nitrogen atmosphere at 40-45° C. for 1 hour. After the reaction mixture was concentrated, the residue was subjected to silica gel column chromatography, and crystals of 4-(4-chlorophenyl)-5-[3-(2-methoxyphenoxy)propyl]-2-(1-pyrazolyl)oxazole (702 mg, 51%) were obtained from an ethyl acetate-hexane (1:2, v/v)-eluted fraction. Recrystallization from acetone-hexane gave pale yellow prisms. Melting point 103-104° C.

EXAMPLE 21

A mixture of 4-(4-chlorophenyl)-2-(1H-1,2,4-triazol-1-yl)-5-oxazolepropanol (0.61 g), 2-methoxyphenol (500 mg), cyanomethylenetributylphosphorane (1.00 g, produced by Tokyo Kasei) and tetrahydrofuran (10 ml) was stirred in a nitrogen atmosphere at 55-60° C. for 1 hour. After the reaction mixture was concentrated, the residue was subjected to silica gel column chromatography, and crystals of 4-(4-chlorophenyl)-5-[3-(2-methoxyphenoxy)propyl]-2-(1H-1,2,4-trizol-1-yl)oxazole (553 mg, 67%) were obtained from an ethyl acetate-hexane (1:3, v/v)-eluted fraction. Recrystallization from acetone-hexane gave pale yellow prisms. Melting point 106-107° C.

EXAMPLE 22

A mixture of ethyl 5-bromo-5-(4-chlorobenzoyl)valerate (17.4 g), thiourea (4.57 g) and ethanol (50 ml) was stirred with heating under reflux for 2 hours. The reaction mixture was poured into water (200 ml) and extracted with ethyl acetate (200 ml×2). The organic layer was dried over anhydrous magnesium sulfate and concentrated. The residue was recrystallized from ethanol to give ethyl 2-amino-4-(4-chlorophenyl)-5-thiazolebutanoate (14.6 g, 85%) as pale yellow prisms. Melting point 114-115° C.

EXAMPLE 23

To a mixture of ethyl 2-amino-4-(4-chlorophenyl)-5-thiazolebutanoate (6.50 g), anhydrous cupric chloride (4.03 g) and acetonitrile (50 ml) was added dropwise tert-butyl nitrite (3.09 g) under ice-cooling, and the resulting mixture was stirred at room temperature for 2 hours. The reaction mixture was poured into water (200 ml) and extracted with ethyl acetate (100 ml×2). The organic layer was dried over anhydrous magnesium sulfate and concentrated. The residue was subjected to silica gel column chromatography, and a yellow oil (6.00 g) was obtained from an ethyl acetate-hexane (1:4, v/v)-eluted fraction. To a mixture of this oil (6.00 g), 2-methylimidazole (3.00 g) and N,N-dimethylformamide (20 ml) was added gradually sodium hydride (60% in oil, 1.0 g) under ice-cooling, and the resulting mixture was stirred at 110-120° C. for 4 hours. The reaction mixture was poured into water (200 ml) and extracted with ethyl acetate (150 ml×3). The organic layer was dried over anhydrous magnesium sulfate and then concentrated, the residue was subjected to silica gel column chromatography, and ethyl 4-(4-chlorophenyl)-2-(2-methyl-1-imidazolyl)-5-thiazolebutanoate (2.00 g, 29%) was obtained as a yellow oil from an ethyl acetate-hexane (1:1, v/v)-eluted fraction.

NMR (CDCl$_3$) δ: 1.24 (3H, t, J=7 Hz), 1.95-2.15 (2H, m), 2.40 (2H, t, J=7 Hz), 2.71 (3H, s), 3.00 (2H, t, J=7 Hz), 4.12 (2H, q, J=7 Hz), 7.01 (1H, d, J=1.5 Hz), 7.35 (1H, d, J=1.5 Hz), 7.43 (2H, d, J=8.5 Hz), 7.58 (2H, d, J=8.5 Hz)

EXAMPLE 24

Ethyl 4-(4-chlorophenyl)-2-(2-methyl-1-imidazolyl)-5-thiazolebutanoate (2.00 g) was dissolved in 20 ml of tetrahydrofuran, to which was added gradually lithium aluminum hydride (195 mg) under ice-cooling. The resulting mixture was stirred for 1 hour. Water (0.5 ml) was carefully added to the reaction mixture, the resulting mixture was filtered, and the residue on the filter paper was washed with ethyl acetate. The filtrate was concentrated to give crystals of 4-(4-chlorophenyl)-2-(2-methyl-1-imidazolyl)-5-thiazolebutanol (1.28 g, 72%). Recrystallization from ethyl acetate-hexane gave pale yellow prisms. Melting point 98-99° C.

EXAMPLE 25

To a mixture of 4-(4-chlorophenyl)-2-(2-methyl-1-imidazolyl)-5-thiazolebutanol (600 mg), 2-methoxyphenol (434 mg), tributylphosphine (707 mg) and tetrahydrofuran (20 ml) was added dropwise a toluene solution of diethyl azodicarboxylate (40%, 1.52 g) at room temperature, and the resulting mixture was stirred for 1 hour. After the reaction mixture was concentrated, the residue was subjected to silica gel column chromatography, and crystals of 4-(4-chlorophenyl)-5-[4-(2-methoxyphenoxy)butyl]-2-(2-methyl-1-imidazolyl)thiazole were obtained from an ethyl acetate-hexane (1:1, v/v)-eluted fraction. Recrystallization from acetone-hexane gave pale yellow prisms (395 mg, 51%). Melting point 105-107° C.

EXAMPLE 26

To a mixture of 4-(4-chlorophenyl)-2-(2-methyl-imidazolyl)-5-thiazolebutanol (348 mg), 2-cyanophenol (238 mg), tributylphosphine (404 mg) and tetrahydrofuran (10 ml) was added 1,1'-(azodicarbonyl)dipiperidine (504 mg) at room temperature, and the resulting mixture was stirred at 60-70° C. for 1 hour. After the reaction mixture was concentrated, the residue was subjected to silica gel column chromatography, and crystals of 4-(4-chlorophenyl)-5-[4-(2-cyanophenoxy)butyl]-2-(2-methyl-1-imidazolyl)thiazole were obtained from an ethyl acetate-eluted fraction. Recrystallization from acetone-diethyl ether gave pale yellow prisms (193 mg, 43%). Melting point 109-110° C.

EXAMPLE 27

To a mixture of 4-(4-chlorophenyl)-2-(2-methyl-1-imidazolyl)-5-oxazolepropanol (635 mg), 2-cyanophenol (479 mg), tributylphosphine (808 mg) and tetrahydrofuran (15 ml) was added 1,1'-(azodicarbonyl)dipiperidine (1.08 g) at room temperature, and the resulting mixture was stirred at 60-70° C. for 1 hour. After the reaction mixture was concentrated, the residue was subjected to silica gel column chromatography, and crystals of 4-(4-chlorophenyl)-5-[3-(2-cyanophenoxy)propyl]-2-(2-methyl-1-imidazolyl)oxazole were obtained from an ethyl acetate-hexane (1:1, v/v)-eluted fraction. Recrystallization from acetone-isopropyl ether gave pale yellow prisms (677 mg, 82%). Melting point 136-137° C.

EXAMPLE 28

To a mixture of 4-(4-chlorophenyl)-2-(2-pyridinylsulfanyl)-5-oxazolepropanol (340 mg), 2-methoxyphenol (250 mg), tributylphosphine (400 mg) and tetrahydrofuran (10 ml) was added 1,1'-(azodicarbonyl)dipiperidine (500 mg) at room temperature, and the resulting mixture was stirred for 1 hour. After the reaction mixture was concentrated, the residue was subjected to silica gel column chromatography, and 4-(4-chlorophenyl)-5-[3-(2-methoxyphenoxy)propyl]-2-(2-pyridylsulfanyl)oxazole was obtained as an oil (251 mg, 57%) from an ethyl acetate-hexane (1:4, v/v)-eluted fraction.

NMR (CDCl$_3$): 2.20-2.35 (2H, m), 3.17 (2H, t, J=7 Hz), 3.84 (3H, s), 4.05 (2H, t, J=7 Hz), 6.80-7.00 (4H, m), 7.10-7.20 (1H, m), 7.25-7.40 (3H, m), 7.55-7.65 (3H, m), 8.44 (1H, d, J=4 Hz)

EXAMPLE 29

A mixture of methyl 2-chloro-4-(4-chlorophenyl)-5-oxazolepropionate (2.00 g), 2-mercaptopyrimidine (819 mg), anhydrous potassium carbonate (1.10 g) and N,N-dimethylformamide (10 ml) was heated to 100-110° C. and stirred for 4 hours. The reaction mixture was poured into water (100 ml) and extracted with ethyl acetate (100 ml×2). The organic layer was dried over anhydrous magnesium sulfate and then concentrated, the residue was subjected to silica gel column chromatography, and methyl 4-(4-chlorophenyl)-2-(2-pyrimidinylsulfanyl)-5-oxazolepropionate was obtained as a yellow oil (1.42 g, 57%) from an ethyl acetate-hexane (1:4, v/v)-eluted fraction.

NMR (CDCl$_3$): 2.79 (2H, t, J=7 Hz), 3.30 (2H, t, J=7 Hz), 3.67 (3H, s), 7.08 (1H, t, J=5 Hz), 7.41 (2H, d, J=8.5 Hz), 7.68 (2H, d, J=8.5 Hz), 7.53 (2H, d, J=5 Hz).

EXAMPLE 30

Methyl 4-(4-chlorophenyl)-2-(2-pyrimidinylsulfanyl)-5-oxazolepropionate (1.42 g) was dissolved in tetrahydrofuran (10 ml), to which was added gradually lithium aluminum hydride (100 mg) under ice-cooling. The resulting mixture was stirred for 1 hour. Water (0.2 ml) was carefully added to the reaction mixture, the resulting mixture was filtered, and the residue on the filter paper was washed with ethyl acetate. After the filtrate was concentrated, the residue was subjected to silica gel column chromatography, and crystals of 4-(4-chlorophenyl)-2-(2-pyrimidinylsulfanyl)-5-oxazolepropanol were obtained from an ethyl acetate-hexane (1:1, v/v)-eluted fraction. Recrystallization from acetone-isopropyl ether gave pale yellow prisms (210 mg, 23%). Melting point 99-101° C.

EXAMPLE 31

To a mixture of 2-(2-pyrimidinylsulfanyl)-4-(4-chlorophenyl)-5-oxazolepropanol (174 mg), 2-methoxyphenol (124 mg), tributylphosphine (202 mg) and tetrahydrofuran (5 ml) was added 1,1'-(azodicarbonyl)dipiperidine (252 mg) at room temperature, and the resulting mixture was stirred for 1 hour. After the reaction mixture was concentrated, the residue was subjected to silica gel column chromatography, and 4-(4-chlorophenyl)-5-[3-(2-methoxyphenoxy)propyl]-2-(2-pyrimidinylsulfanyl)oxazole was obtained as an oil (182 mg. 80%) from an ethyl acetate-hexane (1:3, v/v)-eluted fraction.

NMR (CDCl$_3$) δ: 2.20-2.40 (2H, m), 3.21 (2H, t, J=7 Hz), 3.85 (3H, s), 4.08 (2H, t, J=7 Hz), 6.80-6.95 (4H, m), 7.05 (1H, d, J=5 Hz), 7.34 (2H, d, J=8.5 Hz), 7.67 (2H, d, J=8.5 Hz), 8.48 (2H, d, J=5 Hz).

EXAMPLE 32

Ethyl 2-amino-4-(4-chlorophenyl)-5-thiazolebutanoate (3.25 g) was dissolved in tetrahydrofuran (10 ml), to which was added gradually lithium aluminum hydride (380 mg) under ice-cooling. The resulting mixture was stirred for 1 hour. Sodium sulfate decahydrate (2.0 g) was carefully added to the reaction mixture, the resulting mixture was stirred at room temperature for 30 minutes and then filtered. The residue on the filter paper was washed with ethyl acetate. After the filtrate was concentrated, the residue was subjected to silica gel column chromatography, and crystals of 2-amino-4-(4-chlorophenyl)-5-thiazolebutanol (1.80 g, 63%) were obtained from an ethyl acetate-hexane (3:1, v/v)-eluted fraction. Recrystallization from ethyl acetate-diethyl ether gave pale yellow prisms. Melting point 119-121° C.

EXAMPLE 33

To a mixture of 2-amino-4-(4-chlorophenyl)-5-thiazolebutanol (565 mg), 2-methoxyphenol (496 mg), tributylphosphine (808 mg) and tetrahydrofuran (10 ml) was added 1,1'-(azodicarbonyl)dipiperidine (750 mg) at room temperature, and the resulting mixture was stirred for 1 hour. After the reaction mixture was concentrated, the residue was subjected to silica gel column chromatography, and 579 mg of pale yellow prisms were obtained from an ethyl acetate-hexane (1:3, v/v)-eluted fraction. Melting point 57-59° C. (acetone-isopropyl ether). The results of elemental analysis suggested that these crystals were a compound resulting from 1:1 condensation of 2-amino-4-(4-chlorophenyl)-5-[3-(2-methoxyphenoxy)propyl]thiazole and tributylphosphine.

NMR (CDCl$_3$) δ: 0.92 (9H, t, J=7 Hz), 1.30-2.15 (20H, m), 2.80 (2H, t, J=7 Hz), 3.84 (3H, s), 3.98 (2H, t, J=6 Hz), 6.80-6.95 (4H, m), 7.27 (2H, d, J=8.5 Hz), 7.47 (2H, d, J=8.5 Hz).

To a mixture of these crystals (348 mg), anhydrous cupric chloride (150 mg) and acetonitrile (10 ml) was added dropwise tert-butyl nitrite (120 mg) under water-cooling, and the resulting mixture was stirred at room temperature for 2 hours. The reaction mixture was poured into 100 ml of water and extracted with ethyl acetate (150 ml×2). The organic layer was dried over anhydrous magnesium sulfate and then concentrated. The residue was subjected to silica gel column chromatography, and 2-chloro-4-(4-chlorophenyl)-5-[3-(2- methoxyphenoxy)propyl]thiazole (135 mg, 59%) was obtained as a yellow oil from an ethyl acetate-hexane (1:4, v/v)-eluted fraction.

NMR (CDCl$_3$) δ: 1.80-2.00 (4H, m), 2.96 (2H, t, J=7 Hz), 3.84 (3H, s), 4.00 (2H, t, J=6 Hz), 6.80-7.00 (4H, m), 7.35 (2H, d, J=8.5 Hz), 7.50 (2H, d, J=8.5 Hz)

EXAMPLE 34

Ethyl 2-chloro-4-(4-chlorophenyl)-5-oxazolepropionate (9.00 g) was dissolved in tetrahydrofuran (100 ml), the solution was cooled to −78° C., and a 1 N solution of diisobutylaluminum hydride in toluene (65 ml) was added dropwise with stirring. After completion of the dropping, the cooling bath was removed to raise the inner temperature to −20° C. Sodium sulfate decahydrate (10.0 g) was added to the reaction mixture, and the temperature was raised to room temperature. The reaction mixture was filtered, and the residue on the filter paper was washed with ethyl acetate. The filtrate was concentrated to give crystals of 2-chloro-4-(4-chlorophenyl)-5-oxazolepropanol (7.00 g, 86%).

NMR (CDCl$_3$) δ: 1.90-2.10 (2H, m), 2.99 (2H, t, J=7 Hz), 3.73 (2H, t, J=6 Hz), 7.38 (2H, d, J=8.5 Hz), 7.58 (2H, d, J=8.5 Hz)

EXAMPLE 35

To a mixture of 2-chloro-4-(4-chlorophenyl)-5-oxazolepropanol (1.28 g), 2-methoxyphenol (931 mg), tributylphosphine (1.52 g) and tetrahydrofuran (10 ml) was added 1,1'-(azodicarbonyl)dipiperidine (1.89 g) at room temperature, and the resulting mixture was stirred for 1 hour. After the reaction mixture was concentrated, the residue was subjected to silica gel column chromatography, and crystals of 2-chloro-4-(4-chlorophenyl)-5-[3-(2-methoxyphenoxy)propyl]oxazole were obtained from an ethyl acetate-hexane (1:4, v/v)-eluted fraction. Recrystallization from ethyl acetate-hexane gave colorless prisms (1.00 g, 56%). Melting point 81-82° C.

EXAMPLE 36

To a mixture of 2-chloro-4-(4-chlorophenyl)-5-[3-(2-methoxyphenoxy)propyl]oxazole (394 mg), 2-mercapto-1-methylimidazole (229 mg) and N,N-dimethylformamide (5 ml) was added sodium hydride (80 mg) under ice-cooling, and the resulting mixture was stirred at 80-90° C. for 2 hours. The reaction mixture was poured into water (100 ml) and extracted with ethyl acetate (100 ml×2). The organic layer was washed with water (100 ml) and dried over anhydrous magnesium sulfate. After the organic layer was concentrated, the residue was subjected to silica gel column chromatography, and crystals of 4-(4-chlorophenyl)-5-[3-(2-methoxyphenoxy)propyl]-2-(1-methyl-2-imidazolylsulfanyl)oxazole were obtained from an ethyl acetate-hexane (1:1, v/v)-eluted fraction. Recrystallization from acetone-isopropyl ether gave pale yellow prisms (200 mg, 34%). Melting point 118-119° C.

EXAMPLE 37

A mixture of 2-chloro-4-(4-chlorophenyl)-5-[3-(2-methoxyphenoxy)propyl]oxazole (300 mg), 3-mercapto-1-propanol (200 mg), anhydrous potassium carbonate (400 mg) and N,N-dimethylformamide (10 ml) was stirred at room temperature for 2 hours. The reaction mixture was poured into water (100 ml) and extracted with ethyl acetate (100 ml×2), and then the organic layer was washed with water (100 ml) and dried over anhydrous magnesium sulfate. After the organic layer was concentrated, the residue was subjected to silica gel column chromatography, and crystals of 4-(4-chlorophenyl)-2-(3-hydroxy-1-propylsulfanyl)-5-[3-(2-methoxyphenoxy)propyl]oxazole were obtained from an ethyl acetate-hexane (1:1, v/v)-eluted fraction. Recrystallization from acetone-isopropyl ether gave pale yellow prisms (201 mg, 59%). Melting point 77-78° C.

EXAMPLE 38

To a mixture of 2-chloro-4-(4-chlorophenyl)-5-[3-(2-methoxyphenoxy)propyl]oxazole (378 mg), DL-alaninol (150 mg) and tetrahydrofuran (10 ml) was added sodium hydride (80 mg) under ice-cooling, and the resulting mixture was stirred at room temperature for 2 hours. Trifluoroacetic anhydride (600 mg) was added to the reaction mixture, which was stirred at room temperature for another hour. Water (1.0 ml) was added to the reaction mixture, which was concentrated. The residue was subjected to silica gel column chromatography, and crystals of N-[2-[4-(4-chlorophenyl)-5-[3-(2-methoxyphenoxy)propyl]-2-oxazolyloxy]-1-methylethyl]trifluoroacetamide were obtained from an ethyl acetate-hexane (1:4, v/v)-eluted fraction. Recrystallization from ethyl acetate-hexane gave pale yellow prisms (222 mg, 43%). Melting point 92-95° C.

EXAMPLE 39

A mixture of 2-chloro-4-(4-chlorophenyl)-5-[3-(2-methoxyphenoxy)propyl]oxazole (378 mg), morpholine (435 mg) and 2-butanone (10 ml) was stirred with heating under reflux for 2 hours. The reaction mixture was poured into water (100 ml) and extracted with ethyl acetate (100 ml×2). The organic layer was washed with a 10% aqueous solution of citric acid (100 ml) and dried over anhydrous magnesium sulfate. After the organic layer was concentrated, the residue was recrystallized from ethyl acetate-hexane to give 4-(4-chlorophenyl)-2-(4-morpholinyl)-5-[3-(2-methoxyphenoxy)propyl]oxazole as pale yellow prisms (353 mg, 82%). Melting point 81-82° C.

EXAMPLE 40

A mixture of 2-chloro-4-(4-chlorophenyl)-5-[3-(2-methoxyphenoxy)propyl]oxazole (378 mg), ethyl isonipecotate (1.57 g) and 2-butanone (10 ml) was stirred with heating under reflux for 6 hours. The reaction mixture was diluted with ethyl acetate (100 ml), and the organic layer was washed with a 10% aqueous solution of citric acid (50 ml) and dried over anhydrous magnesium sulfate. After the organic layer was concentrated, the residue was recrystallized from ethyl acetate-hexane to give ethyl N-[4-(4-chlorophenyl)-5-[3-(2-methoxyphenoxy)propyl]-2-oxazolyl]isonipecotate as pale yellow prisms (345 mg, 69%). Melting point 80-81° C.

EXAMPLE 41

A mixture of 2-chloro-4-(4-chlorophenyl)-5-[3-(2-methoxyphenoxy)propyl]oxazole (378 mg), N-methylbenzylamine (870 mg) and isopropyl alcohol (10 ml) was stirred with heating under reflux for 12 hours. The reaction mixture was poured into a 10% aqueous solution of citric acid (100 ml) and extracted with ethyl acetate (100 ml×2), and the extract was dried over anhydrous magnesium sulfate. After the organic layer was concentrated, the residue was subjected to silica gel column chromatography, and crystals of 4-(4-chlorophenyl)-2-(N-methyl-N-benzylamino)-5-[3-(2-methoxyphenoxy)propyl]oxazole were obtained from an ethyl acetate-hexane (1:4, v/v)-eluted fraction. Recrystallization from acetone-hexane gave pale yellow prisms (351 mg, 76%). Melting point 56-59° C.

EXAMPLE 42

A mixture of 2-chloro-4-(4-chlorophenyl)-5-[3-(2-methoxyphenoxy)propyl]oxazole (378 mg), 4,5-diphenylimidazole (270 mg), anhydrous potassium carbonate (220 mg) and N,N-dimethylformamide (10 ml) was stirred at 100° C. for 12 hours. The reaction mixture was poured into water, the resulting solid precipitate was filtered and air-dried. Recrystallization of this solid from acetone-isopropyl ether gave 4-(4-chlorophenyl)-2-(4,5-diphenyl-1-imidazolyl)-5-[3-(2-methoxyphenoxy)propyl]oxazole as pale yellow prisms (220 mg, 46%). Melting point 118-119° C.

EXAMPLE 43

A mixture of 2-chloro-4-(4-chlorophenyl)-5-[3-(2-methoxyphenoxy)propyl]oxazole (378 mg), benzimidazole (177 mg), anhydrous potassium carbonate (207 mg) and N,N-dimethylformamide (10 ml) was stirred at 100° C. for 12 hours. The reaction mixture was poured into water and extracted with ethyl acetate (100 ml×2). The organic layer was dried over anhydrous magnesium sulfate and then concentrated. The residue was subjected to silica gel column chromatography, and crystals of 2-(1-benzimidazolyl)-4-(4-chlorophenyl)-5-[3-(2-methoxyphenoxy)propyl]oxazole were obtained from an ethyl acetate-hexane (1:2, v/v)-eluted fraction. Recrystallization from acetone-isopropyl ether gave pale yellow prisms (358 mg, 77%). Melting point 116-117° C.

EXAMPLE 44

A mixture of 2-chloro-4-(4-chlorophenyl)-5-[3-(2-methoxyphenoxy)propyl]oxazole (378 mg), 3-hydroxymethylpiperidine (1.29 g) and 2-butanone (10 ml) was stirred with heating under reflux for 12 hours. The reaction mixture was poured into 100 ml of water and extracted with ethyl acetate (100 ml×2). The organic layer was washed with 100 ml of water, dried over anhydrous magnesium sulfate and then concentrated. The residue was subjected to silica gel column chromatography, and 4-(4-chlorophenyl)-2-(3-hydroxymethyl-1-piperidinyl)-5-[3-(2-methoxyphenoxy)propyl]oxazole was obtained as an oil (102 mg, 27%) from an ethyl acetate-hexane (1:1, v/v)-eluted fraction.

NMR (CDCl$_3$) δ: 1.30-2.00 (6H, m), 2.10-2.30 (2H, m), 3.00 (2H, t, J=7 Hz), 3.20-3.40 (2H, m), 3.54 (2H, d, J=7 Hz), 3.60-3.80 (2H, m), 3.87 (3H, s), 4.06 (2H, t, J=6 Hz), 6.80-7.00 (4H, m), 7.27 (2H, d, J=8.5 Hz), 7.52 (2H, d, J=8.5 Hz).

EXAMPLE 45

A mixture of 2-chloro-4-(4-chlorophenyl)-5-[3-(2-methoxyphenoxy)propyl]oxazole (378 mg), N-methylethanolamine (750 mg) and 2-butanone (10 ml) was stirred with heating under reflux for 6 hours. The reaction mixture was poured into water (100 ml) and extracted with ethyl acetate (100 ml×2). The organic layer was washed with water (100 ml), dried over anhydrous magnesium sulfate and then concentrated. The residue was subjected to silica gel column chromatography, and 4-(4-chlorophenyl)-2-[N-(2-hydroxyethyl)-N-methylamino]-5-[3-(2-methoxyphenoxy)propyl]oxazole as obtained as an oil (108 mg, 26%) from an ethyl acetate-hexane (1:1, v/v)-eluted fraction.

NMR (CDCl$_3$): 2.10-2.30 (2H, m), 3.01 (2H, t, J=7 Hz), 3.5.7 (2H, t, J=7 Hz), 3.80-3.95 (2H, m), 3.87 (3H, s), 4.06 (2H, t, J=6 Hz), 6.80-7.00 (4H, m), 7.27 (2H, d, J=8.5 Hz), 7.50 (2H, d, J=8.5 Hz).

EXAMPLE 46

A mixture of 2-chloro-4-(4-chlorophenyl)-5-[3-(2-methoxyphenoxy)propyl]oxazole (378 mg), benzotriazole (238 mg), anhydrous potassium carbonate (276 mg) and N,N-dimethylformamide (10 ml) was stirred at 100° C. for 3 hours. The reaction mixture was poured into water and extracted with ethyl acetate (100 ml×2). The organic layer was washed with a 10% aqueous solution of citric acid (100 ml), dried over anhydrous magnesium sulfate and then concentrated. The residue was subjected to silica gel column chromatography, and crystals of 2-(1-benzotriazolyl)-4-(4-chlorophenyl)-5-[3-(2-methoxyphenoxy)propyl]oxazole were obtained from an ethyl acetate-hexane (1:4, v/v)-eluted fraction. Recrystallization from ethyl acetate gave pale yellow prisms (232 mg, 51%). Melting point 128-129° C.

EXAMPLE 47

A mixture of 2-chloro-4-(4-chlorophenyl)-5-[3-(2-methoxyphenoxy)propyl]oxazole (378 mg), 1-phenylpiperazine (810 mg) and 2-butanone (15 ml) was stirred with heating under reflux for 12 hours. The reaction mixture was poured into water (100 ml) and extracted with ethyl acetate (150 ml×2). The organic layer was washed with a 10% aqueous solution of citric acid (100 ml), dried over anhydrous magnesium sulfate and concentrated. The residue was subjected to silica gel column chromatography, and 4-(4-chlorophenyl)-5-[3-(2-methoxyphenoxy)propyl]-2-(4-phenyl-1-piperazinyl)oxazole was obtained as an oil (168 mg, 33%) from an ethyl acetate-hexane (1:4, v/v)-eluted fraction.

NMR (CDCl$_3$) δ: 2.15-2.30 (2H, m), 3.02 (2H, t, J=7 Hz), 3.20-3.30 (4H, m), 3.60-3.70 (4H, m), 3.87 (3H, s), 4.07 (2H, t, J=6 Hz), 6.80-7.00 (8H, m), 7.25-7.40 (3H, m), 7.27 (2H, d, J=8.5 Hz), 7.55 (2H, d, J=8.5 Hz).

EXAMPLE 48

To a mixture of (4-chlorophenyl)-2-(2-methyl-1-imidazolyl)-5-oxazolepropanol (100 mg), methyl 4-hydroxyphenylacetate (76 mg), tributylphosphine (93 mg) and tetrahydrofuran (5 ml) was added 1,1'-(azodicarbonyl)dipiperidine (116 mg) at room temperature, and the resulting mixture was stirred for 1 hour. After the reaction mixture was concentrated, the residue was subjected to silica gel column chromatography, and methyl 4-[3-[4-(4-chlorophenyl)-2-(2-methyl-1-imidazolyl)-5-oxazolyl]propoxy]phenylacetate was obtained as an oil (103 mg, 70%) from an ethyl acetate-hexane (1:1, v/v)-eluted fraction.

NMR (CDCl$_3$) δ: 2.15-2.30 (2H, m), 2.76 (3H, s), 3.15 (2H, t, J=7 Hz), 3.69 (3H, s), 4.03 (2H, t, J=6 Hz), 6.81 (2H, d, J=8.5 Hz), 6.99 (1H, d, J=1.5 Hz), 7.19 (2H, d, J=8.5 Hz), 7.35 (2H, d, J=8.5 Hz), 7.42 (1H, d, J=1.5 Hz), 7.60 (2H, d, J=8.5 Hz).

EXAMPLE 49

To a mixture of 4-(4-chlorophenyl)-2-(2-methyl-1-imidazolyl)-5-oxazolepropanol (300 mg), 4-phenoxyphenol (352 mg), tributylphosphine (382 mg) and tetrahydrofuran (15 ml) was added 1,1'-(azodicarbonyl)dipiperidine (478 mg) at room temperature, and the resulting mixture was stirred for 1 hour. After the reaction mixture was concentrated, the residue was subjected to silica gel column chromatography, and crystals of 4-(4-chlorophenyl)-2-(2-methyl-1-imidazolyl)-5-[3-(4-phenoxyphenoxy)propyl]oxazole were obtained from an ethyl acetate-hexane (1:1, v/v)-eluted fraction. Recrystallization from acetone-hexane gave pale yellow prisms (353 mg, 61%). Melting point 114-115° C.

EXAMPLE 50

To a mixture of 4-(4-chlorophenyl)-2-(2-methyl-1-imidazolyl)-5-oxazolepropanol (300 mg), 4-chloro-3-fluorophenol (352 mg), tributylphosphine (382 mg) and tetrahydrofuran (15 ml) was added 1,1'-(azodicarbonyl)dipiperidine (478 mg) at room temperature, and the resulting mixture was stirred for 1 hour. After the reaction mixture was concentrated, the residue was subjected to silica gel column chromatography, and crystals of 5-[3-(4-chloro-3-fluorophenoxy)propyl]-4-(4-chlorophenyl)-2-(2-methyl-1-imidazolyl)oxazole were obtained from an ethyl acetate-hexane (1:1, v/v)-eluted fraction. Recrystallization from acetone-hexane gave pale yellow prisms (272 g, 73%). Melting point 84-86° C.

EXAMPLE 51

A mixture of 2-chloro-4-(4-chlorophenyl)-5-[3-(2-methoxyphenoxy)propyl]oxazole (378 mg), an aqueous solution of dimethylamine (50%, 1.0 ml) and 2-butanone (10 ml) was stirred with heating under reflux for 12 hours. The reaction mixture was concentrated, the residue obtained was subjected to silica gel column chromatography, and 4-(4-chlorophenyl)-2-dimethylamino-5-[3-(2-methoxyphenoxy)propyl]oxazole was obtained as an oil (348 mg, 90%) from an ethyl acetate-hexane (1:4, v/v)-eluted fraction. Crystallization from acetone-hexane gave pale yellow prisms. Melting point 67-68° C.

EXAMPLE 52

To a mixture of 4-(4-fluorophenyl)-2-(2-methyl-1-imidazolyl)-5-oxazolobutanol (315 mg), 2-methylphenol (216 mg), tributylphosphine (405 mg) and tetrahydrofuran (5 ml) was added 1,1'-(azodicarbonyl)dipiperidine (505 mg) at room temperature, and the resulting mixture was stirred for 1 hour. After the reaction mixture was concentrated, the residue was subjected to silica gel column chromatography, and 4-(4-fluorophenyl)-2-(2-methyl-1-imidazolyl)-5-[4-(2-methylphenoxy)butyl]oxazole was obtained as an oil (367 mg, 91%) from an ethyl acetate-hexane (1:1, v/v)-eluted fraction. NMR (CDCl$_3$) δ: 1.90-2.10 (4H, m), 2.20 (3H, s), 2.78 (3H, s), 3.00 (2H, t, J=7 Hz), 4.02 (2H, t, J=6 Hz), 6.75-6.90 (2H, m), 7.01 (1H, d, J=1.5 Hz), 7.05-7.20 (4H, m), 7.47 (1H, d, J=1.5 Hz), 7.60-7.70 (2H, m).

EXAMPLE 53

To a mixture of 5-(4-fluoro-1-naphthyl)-2-(2-methyl-1-imidazolyl)-4-oxazolebutanol (180 mg), 2-methylphenol (108 mg), tributylphosphine (202 mg) and tetrahydrofuran (5 ml) was added 1,1'-(azodicarbonyl)dipiperidine (252 mg) at room temperature, and the resulting mixture was stirred for 1 hour. After the reaction mixture was concentrated, the residue was subjected to silica gel column chromatography, and 5-(4-fluoro-1-naphthyl)-2-(2-methyl-1-imidazolyl)-4-[4-(2-methylphenoxy)butyl]oxazole was obtained as an oil (180 mg, 80%) from an ethyl acetate-hexane (1:1, v/v)-eluted fraction.
NMR (CDCl$_3$) δ: 1.60-2.00 (4H, m), 2.20 (3H, s), 2.63 (2H, t, J=7 Hz), 2.78 (3H, s), 3.91 (2H, t, J=6 Hz), 6.65-6.75 (1H, m), 6.80-6.90 (1H, m), 7.01 (1H, d, J=1.5 Hz), 7.05-7.20 (3H, m), 7.45-7.55 (2H, m), 7.60-7.70 (2H, m), 7.85-7.95 (1H, m), 8.15-8.25 (1H, m).

EXAMPLE 54

To a mixture of 2-chloro-4-(4-chlorophenyl)-5-oxazolepropanol (40.7 g), 2-methylphenol (21.6 g), tributylphosphine (40.4 g) and tetrahydrofuran (300 ml) was added 1,1'-(azodicarbonyl)dipiperidine (40.0 g) gradually at room temperature, and the resulting mixture was stirred for 1 hour. After the reaction mixture was concentrated, the residue was subjected to silica gel column chromatography, and crystals of 2-chloro-4-(4-chlorophenyl)-5-[3-(2-methylphenoxy)propyl]oxazole (43.0 g, 79%) were obtained from an ethyl acetate-hexane (1:6, v/v)-eluted fraction. Recrystallization from ethyl acetate-hexane gave colorless prisms. Melting point 74-75° C.

EXAMPLE 55

A mixture of 2-chloro-4-(4-chlorophenyl)-5-[3-(2-methylphenoxy)propyl]oxazole (1.00 g), imidazole (680 mg), potassium carbonate (1.38 g) and N,N-dimethylformamide (5 ml) was stirred at 120-130° C. for 1 hour. The reaction mixture was poured into water (100 ml), and the solid precipitate was filtered, air-dried and recrystallized from acetone-isopropyl ether to give 4-(4-chlorophenyl)-2-(1-imidazolyl)-5-[3-(2-methylphenoxy)propyl]oxazole as pale yellow prisms (662 mg, 61%). Melting point 113-114° C.

EXAMPLE 56

A mixture of 2-chloro-4-(4-chlorophenyl)-5-[3-(2-methylphenoxy)propyl]oxazole (1.00 g), 2-ethylimidazole (960 mg), potassium carbonate (1.38 g) and N,N-dimethylformamide (10 ml) was stirred at 120-130° C. for 1 hour. The reaction mixture was poured into water (100 ml), and the solid precipitate was filtered, air-dried and recrystallized from acetone-isopropyl ether to give 4-(4-chlorophenyl)-2-(2-ethyl-1-imidazolyl)-5-[3-(2-methylphenoxy)propyl]oxazole as pale yellow prisms (438 mg, 38%). Melting point 91-92° C.

EXAMPLE 57

A mixture of 2-chloro-4-(4-chlorophenyl)-5-[3-(2-methoxylphenoxy)propyl]oxazole (1.00 g), 2-ethylimidazole (960 mg), potassium carbonate (1.38 g) and N,N-dimethylformamide (5 ml) was stirred at 120-130° C. for 1 hour. The reaction mixture was poured into water (100 ml), and the resulting precipitate was filtered, air-dried and recrystallized from acetone-isopropyl ether to give 4-(4-chlorophenyl)-2-(2-ethyl-1-imidazolyl)-5-[3-(2-methoxyphenoxy)propyl]oxazole as pale yellow prisms (618 mg, 53%). Melting point 78-79° C.

EXAMPLE 58

To a mixture of 4-(4-chlorophenyl)-2-(2-methyl-1-imidazolyl)-5-oxazolepropanol (635 mg), 3-methylphenol (432 mg), tributylphosphine (607 mg) and tetrahydrofuran (10 ml) was added 1,1'-(azodicarbonyl)dipiperidine (757 mg) at room temperature, and the resulting mixture was stirred for 1 hour. After the reaction mixture was concentrated, the residue was subjected to silica gel column chromatography, and crystals of 4-(4-chlorophenyl)-2-(2-methyl-1-imidazolyl)-5-[3-(3-methylphenoxy)propyl]oxazole were obtained from an ethyl acetate-hexane (1:1, v/v)-eluted fraction. Recrystallization from acetone-isopropyl ether gave colorless prisms (453 mg, 56%). Melting point 62-63° C.

EXAMPLE 59

To a mixture of 4-(4-chlorophenyl)-2-(2-methyl-1-imidazolyl)-5-oxazolepropanol (635 mg), 4-methylphenol (432 mg), tributylphosphine (607 mg) and tetrahydrofuran (5 ml) was added 1,1'-(azodicarbonyl)dipiperidine (757 mg) at room temperature, and the resulting mixture was stirred for 1 hour. After the reaction mixture was concentrated, the residue was subjected to silica gel column chromatography, and 4-(4-chlorophenyl)-2-(2-methyl-1-imidazolyl)-5-[3-(4-methylphenoxy)propyl]oxazole was obtained as an oil (475 mg, 58%) from an ethyl acetate-hexane (1:1, v/v)-eluted fraction.

NMR (CDCl$_3$) δ: 2.15-2.30 (2H, m), 2.76 (3H, s), 3.15 (2H, t, J=7 Hz), 3.69 (3H, s), 4.03 (2H, t, J=7 Hz), 6.76 (2H, d, J=8.5 Hz), 6.99 (1H, d, J=2.0 Hz), 7.08 (2H, d, J=8.5 Hz), 7.36 (2H, d, J=8.5 Hz), 7.42 (1H, d, J=2.0 Hz), 7.61 (2H, d, J=8.5 Hz).

EXAMPLE 60

To a mixture of 4-(4-chlorophenyl)-2-(2-methyl-1-imidazolyl)-5-oxazolepropanol (1.00 g), 2-isopropyloxyphenol (913 mg), tributylphosphine (1.00 g) and tetrahydrofuran (10 ml) was added 1,1'-(azodicarbonyl)dipiperidine (1.26 g) at room temperature, and the resulting mixture was stirred for 1 hour. After the reaction mixture was concentrated, the residue was subjected to silica gel column chromatography, and crystals of 4-(4-chlorophenyl)-2-(2-methyl-1-imidazolyl)-5-[3-[2-(2-propyloxy)phenoxy]propyl]oxazole were obtained from an ethyl acetate-hexane (1:1, v/v)-eluted fraction. Recrystallization from acetone-isopropyl ether gave colorless prisms (1.33 g, 93%). Melting point 76-77° C.

EXAMPLE 61

A mixture of 4-(4-chlorophenyl)-2-(2-methyl-1-imidazolyl)-5-[3-[2-(2-propyloxy)phenoxy]propyl]oxazole (200 mg), titanium(IV) chloride (380 mg) and methylene chloride (5 ml) was stirred at 0° C. for 1 hour. The reaction mixture was poured into a saturated aqueous solution of sodium hydrogen carbonate (10 ml) and extracted with ethyl acetate (10 ml×2). The organic layer was dried over anhydrous magnesium sulfate and then concentrated, and the residue was recrystallized from acetone-isopropyl ether to give 4-(4-chlorophenyl)-5-[3-(2-hydroxyphenoxy)propyl]-2-(2-methyl-1-imidazolyl)oxazole as colorless prisms (90 mg, 51%). Melting point 110-111° C.

EXAMPLE 62

To a mixture of 4-(4-chlorophenyl)-2-(2-methyl-1-imidazolyl)-5-oxazolepropanol (635 mg), 4-chloro-2-methylphenol (570 mg), tributylphosphine (809 mg) and tetrahydrofuran (10 ml) was added 1,1'-(azodicarbonyl)dipiperidine (1.01 g) at room temperature, and the resulting mixture was stirred for 1 hour. After the reaction mixture was concentrated, the residue was subjected to silica gel column chromatography, and crystals of 5-[3-(4-chloro-2-methylphenoxy)propyl]-4-(4-chlorophenyl)-2-(2-methyl-1-imidazolyl)oxazole were obtained from an ethyl acetate-hexane (1:1, v/v)-eluted fraction. Recrystallization from acetone-isopropyl ether gave pale yellow prisms (630 mg, 71%). Melting point 74-76° C.

EXAMPLE 63

To a mixture of 4-(4-chlorophenyl)-2-(2-methyl-1-imidazolyl)-5-oxazolepropanol (635 mg), 4-chloro-2-methoxyphenol (634 mg), tributylphosphine (609 mg) and tetrahydrofuran (10 ml) was added 1,1'-(azodicarbonyl)dipiperidine (756 mg) at room temperature, and the resulting mixture was stirred for 1 hour. After the reaction mixture was concentrated, the residue was subjected to silica gel column chromatography, and crystals of 5-[3-(4-chloro-2-methoxyphenoxy)propyl]-4-(4-chlorophenyl)-2-(2-methyl-1-imidazolyl)oxazole were obtained from an ethyl acetate-hexane (1:1, v/v)-eluted fraction. Recrystallization from acetone-isopropyl ether gave colorless prisms (573 mg, 63%). Melting point 85-87° C.

EXAMPLE 64

To a mixture of 4-(4-chlorophenyl)-2-(2-methyl-1-imidazolyl)-5-oxazolebutanol (1.32 g), 2-methylphenol (865 mg), tributylphosphine (1.21 g) and tetrahydrofuran (30 ml) was added 1,1'-(azodicarbonyl)dipiperidine (1.51 g) at room temperature, and the resulting mixture was stirred for 1 hour. After the reaction mixture was concentrated, the residue was subjected to silica gel column chromatography, and 4-(4-chlorophenyl)-2-(2-methyl-1-imidazolyl)-5-[4-(2-methylphenoxy)butyl]oxazole was obtained as crystals (1.61 g, 96%) from an ethyl acetate-hexane (1:1, v/v)-eluted fraction. Recrystallization from acetone-isopropyl ether gave colorless prisms. Melting point 71-72° C.

EXAMPLE 65

To a mixture of 4-(4-chlorophenyl)-2-(2-methyl-1-imidazolyl)-5-oxazolepentanol (690 mg), 2-methylphenol (432 mg), tributylphosphine (607 mg) and tetrahydrofuran (10 ml) was added 1,1'-(azodicarbonyl)dipiperidine (757 mg) at room temperature, and the resulting mixture was stirred for 1 hour. After the reaction mixture was concentrated, the residue was subjected to silica gel column chromatography, and crystals of 4-(4-chlorophenyl)-2-(2-methyl-1-imidazolyl)-5-[5-(2-methylphenoxy)pentyl]oxazole were obtained from an ethyl acetate-hexane (1:1, v/v)-eluted fraction. Recrystallization from diethyl ether-isopropyl ether gave pale yellow prisms (573 mg, 66%). Melting point 61-62° C.

EXAMPLE 66

To a mixture of 4-(4-chlorophenyl)-2-(2-methyl-1-imidazolyl)-5-oxazolehexanol (360 mg), 2-methylphenol (216 mg), tributylphosphine (405 mg) and tetrahydrofuran (5 ml) was added 1,1'-(azodicarbonyl)dipiperidine (504 mg) at room temperature, and the resulting mixture was stirred for 1 hour. After the reaction mixture was concentrated, the residue was subjected to silica gel column chromatography, and crystals of 4-(4-chlorophenyl)-2-(2-methyl-1-imidazolyl)-5-[6-(2-methylphenoxy)hexyl]oxazole were obtained from an ethyl acetate-hexane (1:1, v/v)-eluted fraction. Recrystallization from diethyl ether-hexane gave colorless prisms (280 mg, 62%). Melting point 70-71° C.

EXAMPLE 67

To a mixture of 4-(4-chlorophenyl)-2-(2-methyl-1-imidazolyl)-5-oxazolepropanol (318 mg), 4-tert-butylphenol (300 mg), tributylphosphine (405 mg) and tetrahydrofuran (10 ml) was added 1,1'-(azodicarbonyl)dipiperidine (370 mg) at room temperature, and the resulting mixture was stirred for 1 hour. After the reaction mixture was concentrated, the residue was subjected to silica gel column chromatography, and crystals of 4-(4-chlorophenyl)-5-[3-(4-tert-butylphenoxy)propyl]-2-(2-methyl-1-imidazolyl)oxazole were obtained from an ethyl acetate-hexane (1:1, v/v)-eluted fraction. Recrystallization from acetone-isopropyl ether gave pale yellow prisms (93 mg, 21%). Melting point 75-77° C.

EXAMPLE 68

To a mixture of 4-(4-chlorophenyl)-2-(2-methyl-1-imidazolyl)-5-oxazolepropanol (318 mg), 2,4-dimethylphenol (245 mg), tributylphosphine (303 mg) and tetrahydrofuran (10 ml) was added 1,1'-(azodicarbonyl)dipiperidine (370 mg) at room temperature, and the resulting mixture was stirred for 1 hour. After the reaction mixture was concentrated, the residue was subjected to silica gel column chromatography, and crystals of 4-(4-chlorophenyl)-5-[3-(2,4-dimethylphenoxy)propyl]-2-(2-methyl-1-imidazolyl)oxazole were obtained from an ethyl acetate-hexane (1:1, v/v)-eluted fraction. Recrystallization from acetone-isopropyl ether gave pale yellow prisms (168 mg, 39%). Melting point 76-77° C.

EXAMPLE 69

A mixture of 2-chloro-4-(4-chlorophenyl)-5-[3-(2-methoxyphenoxy)propyl]oxazole (1.00 g), ethyl 2-imidazolecarboxylate (990 mg), potassium carbonate (1.38 g) and N,N-dimethylformamide (10 ml) was stirred at 120-130° C. for 1 hour. The reaction mixture was poured into water (100 ml), and the resulting solid precipitate was filtered, air-dried and recrystallized from acetone-isopropyl ether to give ethyl 1-[4-(4-chlorophenyl)-5-[3-(2-methoxyphenoxy)propyl]-2-oxazolyl]imidazole-2-carboxylate as pale yellow prisms (290 mg, 23%). Melting point 90-91° C.

EXAMPLE 70

A mixture of 2-chloro-4-(4-chlorophenyl)-5-[3-(2-methylphenoxy)propyl]oxazole (1.00 g), 2-isopropylimidazole (661 mg), potassium carbonate (830 mg) and N,N-dimethylformamide (10 ml) was stirred at 120-130° C. for 1 hour. The reaction mixture was poured into water (100 ml) and extracted with ethyl acetate (10 ml×2). The organic layer was dried over anhydrous magnesium sulfate and then concentrated. The residue was subjected to silica gel column chromatography, and 4-(4-chlorophenyl)-2-(2-isopropyl-1-imidazolyl)-5-[3-(2-methylphenoxy)propyl]oxazole was obtained as an oil (333 mg, 28%) from an ethyl acetate-hexane (1:1, v/v)-eluted fraction.

NMR (CDCl$_3$) δ: 1.39 (6H, d, J=7 Hz), 2.24 (3H, s), 2.20-2.35 (2H, m), 3.19 (2H, t, J=7 Hz), 3.70-3.85 (1H, m), 4.07 (2H, t, J=7 Hz), 6.75-6.80 (1H, m), 6.80-6.95 (1H, m), 7.02 (1H, d, J=2.0 Hz), 7.10-7.20 (2H, m), 7.34 (2H, d, J=8.5 Hz), 7.37 (1H, d, J=2.05 Hz), 7.61 (2H, d, J=8.5 Hz)

EXAMPLE 71

A mixture of 2-chloro-4-(4-chlorophenyl)-5-[3-(2-methylphenoxy)propyl]oxazole (1.00 g), 2-phenylimidazole (432 mg), potassium carbonate (1.38 g) and N,N-dimethylformamide (10 ml) was stirred at 120-130° C. for 1 hour. The reaction mixture was poured into water (100 ml) and extracted with ethyl acetate (10 ml×2). The organic layer was dried over anhydrous magnesium sulfate and concentrated. The residue was subjected to silica gel column chromatography, and 4-(4-chlorophenyl)-5-[3-(2-methylphenoxy)propyl]-2-(2-phenyl-1-imidazolyl)oxazole was obtained as an oil (512 mg, 39%) from an ethyl acetate-hexane (1:1, v/v)-eluted fraction.

NMR (CDCl$_3$) δ: 1.90-2.10 (2H, m), 2.19 (3H, s), 3.03 (2H, t, J=7 Hz), 3.88 (2H, t, J=7 Hz), 6.65-6.75 (1H, m), 6.80-6.90 (1H, m), 7.05-7.20 (2H, m), 7.25-7.60 (11H, m)

EXAMPLE 72

A mixture of 2-chloro-4-(4-chlorophenyl)-5-[3-(2-methylphenoxy)propyl]oxazole (1.00 g), 3,5-dimethylpyrazole (1.00 g), potassium carbonate (1.38 g) and N,N-dimethylformamide (10 ml) was stirred at 120-130° C. for 1 hour. The reaction mixture was poured into water (100 ml), and the resulting solid precipitate was filtered, air-dried and recrystallized from acetone-isopropyl ether to give 4-(4-chlorophenyl)-2-(3,5-dimethyl-1-pyrazolyl)-5-[3-(2-methylphenoxy)propyl]oxazole as pale yellow prisms (187 mg, 16%). Melting point 103-104° C.

EXAMPLE 73

To a mixture of 4-(4-chlorophenyl)-2-(2-methyl-1-imidazolyl)-5-oxazolepropanol (318 mg), phenol (188 mg), tributylphosphine (405 mg) and tetrahydrofuran (10 ml) was added 1,1'-(azodicarbonyl)dipiperidine (400 mg) at room temperature, and the resulting mixture was stirred for 1 hour. After the reaction mixture was concentrated, the residue was subjected to silica gel column chromatography, and crystals of 4-(4-chlorophenyl)-2-(2-methyl-1-imidazolyl)-5-(3-phenoxypropyl)oxazole were obtained from an ethyl acetate-hexane (1:1, v/v)-eluted fraction. Recrystallization from diethyl ether-hexane gave colorless prisms (130 mg, 33%). Melting point 76-77° C.

EXAMPLE 74

To a mixture of 4-(4-chlorophenyl)-2-(2-methyl-1-imidazolyl)-5-oxazolepropanol (318 mg), 2,3-dimethylphenol (245 mg), tributylphosphine (405 mg) and tetrahydrofuran (10 ml) was added 1,1'-(azodicarbonyl)dipiperidine (504 mg) at room temperature, and the resulting mixture was stirred for 1 hour. After the reaction mixture was concentrated, the residue was subjected to silica gel column chromatography, and crystals of 4-(4-chlorophenyl)-2-(2-methyl-1-imidazolyl)-5-[3-(2,3-dimethylphenoxy)propyl]oxazole were obtained from an ethyl acetate-hexane (1:1, v/v)-eluted fraction. Recrystallization from diethyl ether-isopropyl ether gave pale yellow prisms (207 mg, 49%). Melting point 102-104° C.

EXAMPLE 75

To a mixture of 4-(4-chlorophenyl)-2-(2-methyl-1-imidazolyl)-5-oxazolepropanol (318 mg), 3,5-dimethylphenol (245 mg), tributylphosphine (405 mg) and tetrahydrofuran (10 ml) was added 1,1'-(azodicarbonyl)dipiperidine (504 mg) at room temperature, and the resulting mixture was stirred for 1 hour. After the reaction mixture was concentrated, the residue was subjected to silica gel column chromatography, and crystals of 4-(4-chlorophenyl)-2-(2-methyl-1-imidazolyl)-5-

[3-(3,5-dimethylphenoxy)propyl]oxazole were obtained from an ethyl acetate-hexane (1:1, v/v)-eluted fraction. Recrystallization from diethyl ether-hexane gave colorless prisms (340 mg, 81%). Melting point 96-97° C.

EXAMPLE 76

To a mixture of 4-(4-chlorophenyl)-2-(2-methyl-1-imidazolyl)-5-oxazolepropanol (318 mg), 2,6-dimethylphenol (245 mg), tributylphosphine (405 mg) and tetrahydrofuran (10 ml) was added 1,1'-(azodicarbonyl)dipiperidine (504 mg) at room temperature, and the resulting mixture was stirred for 1 hour. After the reaction mixture was concentrated, the residue was subjected to silica gel column chromatography, and crystals of 4-(4-chlorophenyl)-5-[3-(2,6-dimethylphenoxy)propyl]-2-(2-methyl-1-imidazolyl)oxazole were obtained from an ethyl acetate-hexane (1:1, v/v)-eluted fraction. Recrystallization from acetone-hexane gave colorless prisms (300 mg, 71%). Melting point 114-115° C.

EXAMPLE 77

To a mixture of 4-(4-chlorophenyl)-2-(2-methyl-1-imidazolyl)-5-oxazolepropanol (318 mg), 2-methyl-5-isopropylphenol (300 mg), tributylphosphine (405 mg) and tetrahydrofuran (10 ml) was added 1,1'-(azodicarbonyl)dipiperidine (504 mg) at room temperature, and the resulting mixture was stirred for 1 hour. After the reaction mixture was concentrated, the residue was subjected to silica gel column chromatography, and crystals of 4-(4-chlorophenyl)-2-(2-methyl-1-imidazolyl)-5-[3-(2-methyl-5-isopropylphenoxy)propyl]oxazole were obtained from an ethyl acetate-hexane (1:1, v/v)-eluted fraction. Recrystallization from diethyl ether-hexane gave colorless prisms (280 mg, 62%). Melting point 90-91° C.

EXAMPLE 78

To a mixture of 4-(4-chlorophenyl)-2-(2-methyl-1-imidazolyl)-5-oxazolepropanol (318 mg), 2-isopropylphenol (272 mg), tributylphosphine (405 mg) and tetrahydrofuran (10 ml) was added 1,1'-(azodicarbonyl)dipiperidine (504 mg) at room temperature, and the resulting mixture was stirred for 1 hour. After the reaction mixture was concentrated, the residue was subjected to silica gel column chromatography, and crystals of 4-(4-chlorophenyl)-2-(2-methyl-1-imidazolyl)-5-[3-(2-isopropylphenoxy)propyl]oxazole were obtained from an ethyl acetate-hexane (1:1, v/v)-eluted fraction. Recrystallization from diethyl ether-hexane gave colorless prisms (349 mg, 80%). Melting point 83-84° C.

EXAMPLE 79

To a mixture of 4-(4-chlorophenyl)-2-(2-methyl-1-imidazolyl)-5-oxazolepropanol (318 mg), 2-hydroxyindane (268 mg), tributylphosphine (405 mg) and tetrahydrofuran (10 ml) was added 1,1'-(azodicarbonyl)dipiperidine (400 mg) at room temperature, and the resulting mixture was stirred for 1 hour. After the reaction mixture was concentrated, the residue was subjected to silica gel column chromatography, and 4-(4-chlorophenyl)-5-[3-(5-indanyloxy)propyl]-2-(2-methyl-1-imidazolyl)oxazole was obtained as an oil (418 mg, 96%) from an ethyl acetate-hexane (1:1, v/v)-eluted fraction.

NMR (CDCl$_3$) δ: 2.00-2.20 (2H, m), 2.15-2.30 (2H, m), 2.76 (3H, s), 2.80-2.90 (4H, m), 3.15 (2H, t, J=7 Hz), 4.02 (2H, t, J=7 Hz), 6.60-6.70 (1H, m), 6.80-6.90 (1H, m), 7.00 (1H, d, J=2 Hz), 7.10 (1H, d, J=8 Hz), 7.36 (2H, d, J=8.5 Hz), 7.42 (1H, d, J=2 Hz), 7.62 (2H, d, J=8.5 Hz)

EXAMPLE 80

To a mixture of 4-(4-chlorophenyl)-2-(2-methyl-1-imidazolyl)-5-oxazolepropanol (318 mg), 1-hydroxytetralin (296 mg), tributylphosphine (405 mg) and tetrahydrofuran (10 ml) was added 1,1'-(azodicarbonyl)dipiperidine (400 mg) at room temperature, and the resulting mixture was stirred for 1 hour. After the reaction mixture was concentrated, the residue was subjected to silica gel column chromatography, and crystals of 4-(4-chlorophenyl)-2-(2-methyl-1-imidazolyl)-5-[3-(5,6,7,8-tetrahydro-1-naphthoxy)propyl]oxazole were obtained from an ethyl acetate-hexane (1:1, v/v)-eluted fraction. Recrystallization from acetone-hexane gave colorless prisms (387 mg, 86%). Melting point 125-126° C.

EXAMPLE 81

To a mixture of 4-(4-chlorophenyl)-2-(2-methyl-1-imidazolyl)-5-oxazolepropanol (318 mg), 2-hydroxytetralin (296 mg), tributylphosphine (405 mg) and tetrahydrofuran (10 ml) was added 1,1'-(azodicarbonyl)dipiperidine (400 mg) at room temperature, and the resulting mixture was stirred for 1 hour. After the reaction mixture was concentrated, the residue was subjected to silica gel column chromatography, and 4-(4-chlorophenyl)-2-(2-methyl-1-imidazolyl)-5-[3-(5,6,7,8-tetrahydro-2-naphthoxy)propyl]oxazole was obtained as an oil from an ethyl acetate-hexane (1:1, v/v)-eluted fraction. (358 mg, 80%).

NMR (CDCl$_3$) δ: 1.70-1.90 (4H, m), 2.15-2.30 (2H, m), 2.60-2.80 (4H, m), 2.77 (3H, s), 3.14 (2H, t, J=7 Hz), 4.01 (2H, t, J=7 Hz), 6.50-6.70 (2H, m), 6.90-7.00 (1H, m), 7.00 (1H, d, J=2 Hz), 7.36 (2H, d, J=8.5 Hz), 7.42 (1H, d, J=2 Hz), 7.62 (2H, d, J=8.5 Hz).

EXAMPLE 82

To a mixture of 4-(4-methoxyphenyl)-2-(2-methyl-1-imidazolyl)-5-oxazolebutanol (655 mg), 2-methylphenol (432 mg), tributylphosphine (810 mg) and tetrahydrofuran (10 ml) was added 1,1'-(azodicarbonyl)dipiperidine (757 mg) at room temperature, and the resulting mixture was stirred for 1 hour. After the reaction mixture was concentrated, the residue was subjected to silica gel column chromatography, and crystals of 4-(4-methoxyphenyl)-2-(2-methyl-1-imidazolyl)-5-[4-(2-methylphenoxy)butyl]oxazole were obtained from an ethyl acetate-hexane (1:1, v/v)-eluted fraction. Recrystallization from diethyl ether-hexane gave pale yellow prisms (532 mg, 64%). Melting point 59-60° C.

EXAMPLE 83

A mixture of 2-chloro-4-(4-chlorophenyl)-5-[3-(2-methoxyphenoxy)propyl]oxazole (500 mg), 2-propylimidazole (1.10 g), potassium carbonate (1.38 g) and N,N-dimethylformamide (10 ml) was stirred at 120-130° C. for 4 hours. The reaction mixture was poured into water (100 ml), the resulting solid precipitate was filtered, air-dried and recrystallized from acetone-hexane to give 4-(4-chlorophenyl)-5-[3-(2-methoxyphenoxy)propyl]-2-(2-propyl-1-imidazolyl)oxazole as pale yellow prisms (233 mg, 39%). Melting point 89-90° C.

EXAMPLE 84

A mixture of 2-chloro-4-(4-chlorophenyl)-5-[3-(2-methoxyphenoxy)propyl]oxazole (500 mg), 2-undecylimidazole (500 mg), potassium carbonate (1.38 g) and N,N-dimethylformamide (10 ml) was stirred at 120-130° C. for 4 hours. The reaction mixture was poured into water (100 ml) and extracted with ethyl acetate (100 ml×2). The organic layer was dried over anhydrous magnesium sulfate and concentrated. The residue was recrystallized from diethyl ether-hexane to give 4-(4-chlorophenyl)-5-[3-(2-methoxyphenoxy)propyl]-2-(2-undecyl-1-imidazolyl)oxazole as pale yellow prisms (100 mg, 13%). Melting point 53-54° C.

EXAMPLE 85

A mixture of 2-chloro-4-(4-chlorophenyl)-5-[3-(2-methylphenoxy)propyl]oxazole (500 mg), methyl 2-imidazolepropionate (500 mg), potassium carbonate (690 mg) and N,N-dimethylformamide (10 ml) was stirred at 120-130° C. for 6 hours. The reaction mixture was poured into 100 ml of water and extracted with ethyl acetate (100 ml×2). The organic layer was dried over anhydrous magnesium sulfate and concentrated. The residue was subjected to silica gel column chromatography, and crystals of methyl 1-[4-(4-chlorophenyl)-5-[3-(2-methylphenoxy)propyl]-2-oxazolyl]-2-imidazolepropionate were obtained from an ethyl acetate-hexane (1:1, v/v)-eluted fraction. Recrystallization from ethyl acetate-isopropyl ether gave pale yellow prisms (350 mg, 53%). Melting point 82-83% C.

EXAMPLE 86

To a mixture of 4-(4-chlorophenyl)-2-(2-methyl-1-imidazolyl)-5-oxazolepropanol (318 mg), 3,4,5-trimethylphenol (272 mg), tributylphosphine (405 mg) and tetrahydrofuran (10 ml) was added 1,1'-(azodicarbonyl)dipiperidine (400 mg) at room temperature, and the resulting mixture was stirred for 1 hour. After the reaction mixture was concentrated, the residue was subjected to silica gel column chromatography, and crystals of 4-(4-chlorophenyl)-2-(2-methyl-1-imidazolyl)-5-[3-(3,4,5-trimethylphenoxy)propyl]oxazole were obtained from an ethyl acetate-hexane (1:1, v/v)-eluted fraction. Recrystallization from acetone-hexane gave colorless prisms (222 mg, 51%). Melting point 75-76° C.

EXAMPLE 87

To a mixture of 4-(4-chlorophenyl)-2-(2-methyl-1-imidazolyl)-5-oxazolepropanol (318 mg), 2,4,6-trimethylphenol (273 mg), tributylphosphine (405 mg) and tetrahydrofuran (10 ml) was added 1,1'-(azodicarbonyl)dipiperidine (400 mg) at room temperature, and the resulting mixture was stirred for 1 hour. After the reaction mixture was concentrated, the residue was subjected to silica gel column chromatography, and crystals of 4-(4-chlorophenyl)-2-(2-methyl-1-imidazolyl)-5-[3-(2,4,6-trimethylphenoxy)propyl]oxazole were obtained from an ethyl acetate-hexane (1:1, v/v)-eluted fraction. Recrystallization from acetone-hexane gave colorless prisms (82 mg, 20%). Melting point 110-111° C.

EXAMPLE 88

To a mixture of 4-(4-chlorophenyl)-2-(2-methyl-1-imidazolyl)-5-oxazolepropanol (318 mg), 2,3-dimethoxylphenol (308 mg), tributylphosphine (405 mg) and tetrahydrofuran (10 ml) was added 1,1'-(azodicarbonyl)dipiperidine (400 mg) at room temperature, and the resulting mixture was stirred for 1 hour. After the reaction mixture was concentrated, the residue was subjected to silica gel column chromatography, and crystals of 4-(4-chlorophenyl)-5-[3-(2,3-dimethoxyphenoxy)propyl]-2-(2-methyl-1-imidazolyl)oxazole were obtained from an ethyl acetate-hexane (1:1, v/v)-eluted fraction. Recrystallization from acetone-hexane gave colorless prisms (359 mg, 79%). Melting point 104-105° C.

EXAMPLE 89

To a mixture of 4-(4-chlorophenyl)-2-(2-methyl-1-imidazolyl)-5-oxazolepropanol (318 mg), 3,4,5-trimethoxylphenol (368 mg), tributylphosphine (405 mg) and tetrahydrofuran (10 ml) was added 1,1'-(azodicarbonyl)dipiperidine (400 mg) at room temperature, and the resulting mixture was stirred for 1 hour. After the reaction mixture was concentrated, the residue was subjected to silica gel column chromatography, and crystals of 4-(4-chlorophenyl)-2-(2-methyl-1-imidazolyl)-5-[3-(3,4,5-trimethoxyphenoxy)propyl]oxazole were obtained from an ethyl acetate-hexane (1:1, v/v)-eluted fraction. Recrystallization from acetone-hexane gave pale yellow prisms (346 mg, 71%). Melting point 146-147° C.

EXAMPLE 90

To a mixture of 4-(4-chlorophenyl)-2-(2-methyl-1-imidazolyl)-5-oxazolepropanol (318 mg), 2,6-dimethoxylphenol (308 mg), tributylphosphine (405 mg) and tetrahydrofuran (10 ml) was added 1,1'-(azodicarbonyl)dipiperidine (400 mg) at room temperature, and the resulting mixture was stirred for 1 hour. After the reaction mixture was concentrated, the residue was subjected to silica gel column chromatography, and crystals of 4-(4-chlorophenyl)-5-[3-(2,6-dimethoxyphenoxy)propyl]-2-(2-methyl-1-imidazolyl)oxazole were obtained from an ethyl acetate-hexane (1:1, v/v)-eluted fraction. Recrystallization from acetone-hexane gave pale yellow prisms (336 mg, 74%). Melting point 83-84° C.

EXAMPLE 91

To a mixture of 4-(4-chlorophenyl)-2-(2-methyl-1-imidazolyl)-5-oxazolepropanol (800 mg), 2-methylsulfanylphenol (560 mg), tributylphosphine (809 mg) and tetrahydrofuran (20 ml) was added 1,1'-(azodicarbonyl)dipiperidine (800 mg) at room temperature, and the resulting mixture was stirred for 1 hour. After the reaction mixture was concentrated, the residue was subjected to silica gel column chromatography, and crystals of 4-(4-chlorophenyl)-2-(2-methyl-1-imidazolyl)-5-[3-(2-methylsulfanylphenoxy)propyl]oxazole were obtained from an ethyl acetate-hexane (1:1, v/v)-eluted fraction. Recrystallization from acetone-hexane gave pale yellow prisms (664 mg, 60%). Melting point 118-119° C.

EXAMPLE 92

To a mixture of 4-(4-chlorophenyl)-2-(2-methyl-1-imidazolyl)-5-oxazolepropanol (953 mg), methyl 3-(2-hydroxyphenyl)propionate (1.08 g), tributylphosphine (1.21 g) and tetrahydrofuran (20 ml) was added 1,1'-(azodicarbonyl)dipiperidine (1.20 g) at room temperature, and the resulting mixture was stirred for 1 hour. After the reaction mixture was concentrated, the residue was subjected to silica gel column chromatography, and crystals of methyl 3-[2-[3-[4-(4-chlorophenyl)-2-(2-methyl-1-imidazolyl)-5-oxazolyl]propoxy]phenyl]propionate were obtained from an ethyl acetate-hexane (1:1, v/v)-eluted fraction. Recrystallization from acetone-hexane gave pale yellow prisms (1.05 g, 73%). Melting point 91-92° C.

EXAMPLE 93

To a mixture of methyl 3-[2-[3-[4-(4-chlorophenyl)-2-(2-methyl-1-imidazolyl)-5-oxazolyl]propoxy]phenyl]propionate (400 mg) and tetrahydrofuran (10 ml) was added gradually lithium aluminum hydride (40 mg) under ice-cooling, and the resulting mixture was stirred for 1 hour. Sodium sulfate decahydrate (400 mg) was carefully added to the reaction mixture, which was filtered. The residue on the filter paper was washed with ethyl acetate. The filtrate was concentrated, and hexane was added to the residue to give crystals of 4-(4-chlorophenyl)-5-[3-(2-(3-hydroxypropyl)phenoxy)propyl]-2-(2-methyl-1-imidazolyl)oxazole (264 mg, 65%). Recrystallization from ethyl acetate-hexane gave colorless prisms. Melting point 119-120° C.

EXAMPLE 94

To a mixture of methyl 3-[2-[3-[4-(4-chlorophenyl)-2-(2-methyl-1-imidazolyl)-5-oxazolyl]propoxy]phenyl]propionate (400 mg), tetrahydrofuran (5 ml) and ethanol (5 ml) was added 5 ml of a 1 N aqueous solution of sodium hydroxide, and the resulting mixture was stirred at room temperature for 3 hours. The reaction mixture was poured into water (100 ml), and the mixture was neutralized with 1 N hydrochloric acid. The resulting solid precipitate was filtered, washed with water and air-dried to give crude crystals of 3-[2-[3-[4-(4-chlorophenyl)-2-(2-methyl-1-imidazolyl)-5-oxazolyl]propoxy]phenyl]propionic acid. Recrystallization from tetrahydrofuran-hexane gave colorless prisms (260 mg, 54%). Melting point 184-185° C.

EXAMPLE 95

To a mixture of methyl 2-amino-4-(4-chlorophenyl)-5-thiazolepropionate (6.00 g), anhydrous cupric chloride (4.03 g) and acetonitrile (40 ml) was added dropwise tert-butyl nitrite (3.09 mg) under water-cooling, and the resulting mixture was stirred at room temperature for 2 hours. The reaction mixture was poured into water (200 ml) and extracted with ethyl acetate (150 ml×2). The organic layer was dried over anhydrous magnesium sulfate and concentrated. The residue was subjected to silica gel column chromatography, and a yellow oil (3.16 g) was obtained from an ethyl acetate-hexane (1:4, v/v)-eluted fraction. This oil was dissolved in tetrahydrofuran (50 ml), to which was added dropwise diisobutylaluminum hydride (1.0 M solution in hexane, 25 ml) with stirring at −78° C. The temperature was then raised to −20° C., sodium sulfate decahydrate (1.0 g) was added, and the mixture was allowed to return to room temperature with stirring and then filtered. The filtrate was concentrated to give 2-chloro-4-(4-chlorophenyl)-5-thiazolepropanol as an oil (2.02 g, 70%).

NMR (CDCl$_3$) δ: 1.80-2.00 (2H, m), 3.00 (2H, t, J=7.0 Hz), 3.70 (2H, t, J=6.0 Hz), 7.40 (2H, d, J=8.5 Hz), 7.53 (2H, d, J=8.5 Hz)

EXAMPLE 96

To a mixture of 2-chloro-4-(4-chlorophenyl)-5-thiazolepropanol (1.90 g), 2-methylphenol (1.30 g), tributylphosphine (2.43 g) and tetrahydrofuran (30 ml) was added 1,1'-(azodicarbonyl)dipiperidine (2.50 g) at room temperature, and the resulting mixture was stirred for 1 hour. After the reaction mixture was concentrated, and the residue was subjected to silica gel column chromatography. The ethyl acetate-hexane (1:1, v/v)-eluted fraction was concentrated to give a yellow oil, which was dissolved in N,N-dimethylformamide (10 ml). 2-Methylimidazole (1.64 g) and potassium carbonate (2.76 g) were added to the reaction mixture, which was stirred at 120-130° C. for 4 hours. The reaction mixture was poured into water (100 ml), and the resulting solid precipitate was filtered, air-dried and recrystallized from acetone-hexane to give 4-(4-chlorophenyl)-2-(2-methyl-1-imidazolyl)-5-[3-(2-methylphenoxy)propyl]thiazole as pale yellow prisms (394 mg, 14%). Melting point 112-113° C.

EXAMPLE 97

A mixture of ethyl 4-[4-(5-chloro-2-thienyl)-2-oxo-4-oxazolin-5-yl]butanoate (12.5 g), phosphorus oxychloride (24.5 g) and pyridine (3.16 g) was heated to 120-130° C. and stirred for 45 minutes. The reaction mixture was poured into ice-water (200 ml) and extracted with ethyl acetate (150 ml×2). The organic layer was washed in sequence with a 10% aqueous solution of sodium hydrogen carbonate (100 ml) and a saturated aqueous solution of sodium chloride (100 ml) and dried over anhydrous magnesium sulfate. The organic layer was concentrated, the residue was subjected to silica gel column chromatography, and ethyl 2-chloro-4-(5-chloro-2-thienyl)-5-oxazolebutanoate was obtained as a yellow oil (5.79 g, 48%) from an ethyl acetate-hexane (1:4, v/v)-eluted fraction.

NMR (CDCl$_3$): 1.15 (3H, t, J=7 Hz), 1.90-2.05 (2H, m), 2.29 (2H, t, J=7.0 Hz), 2.81 (2H, t, J=7 Hz), 4.04 (2H, q, J=7. Hz), 6.79 (1H, d, J=4 Hz), 6.97 (1H, d, J=4 Hz)

EXAMPLE 98

A mixture of ethyl 2-chloro-4-(5-chloro-2-thienyl)-5-oxazolebutanoate (4.34 g), 2-methylimidazole (3.54 g), potassium carbonate (5.97 g) and N,N-dimethylformamide (20 ml) was stirred at 120-130° C. for 2 hours. The reaction mixture was poured into water (100 ml) and extracted with ethyl acetate (150 ml×2). The organic layer was dried over anhydrous magnesium sulfate. The organic layer was then concentrated. The residue was subjected to silica gel column chromatography, and crystals of ethyl 4-(5-chloro-2-thienyl)-2-(2-methyl-1-imidazolyl)-5-oxazolebutanoate (4.10 g, 83%) were obtained from an ethyl acetate-hexane (1:1, v/v)-eluted fraction. Recrystallization from hexane-ethyl acetate gave pale yellow prisms. Melting point 89-90° C.

EXAMPLE 99

Ethyl 4-(5-chloro-2-thienyl)-2-(2-methyl-1-imidazolyl)-5-oxazolebutanoate (1.80 g) was dissolved in 20 ml of tetrahydrofuran, to which was added gradually lithium aluminum hydride (210 mg) under ice-cooling. The resulting mixture was stirred for 1 hour. Water (0.5 ml) was carefully added to the reaction mixture, the resulting mixture was filtered, and the residue on the filter paper was washed with ethyl acetate. The filtrate was concentrated to give crystals of 4-(5-chloro-2-thienyl)-2-(2-methyl-1-imidazolyl)-5-oxazolebutanol. Recrystallization from hexane-ethyl acetate gave pale yellow prisms (497 mg, 31%). Melting point 77-79° C.

EXAMPLE 100

A mixture of ethyl 4-[4-(4-fluorophenyl)-2-oxo-4-oxazolin-5-yl]butanoate (7.00 g), phosphorus oxychloride (14.7 g) and pyridine (1.89 g) was heated to 120-130° C. and stirred for 45 minutes. The reaction mixture was poured into ice water (200 ml) and extracted with ethyl acetate (150 ml×2). The organic layer was washed in sequence with a 10% aqueous solution of sodium hydrogen carbonate (100 ml) and a saturated aqueous solution of sodium chloride (100 ml), and then dried over anhydrous magnesium sulfate. The organic layer was concentrated, the residue was subjected to silica gel column chromatography, and ethyl 2-chloro-4-(4-fluorophenyl)-5-oxazolebutanoate was obtained as a yellow oil (4.23 g, 57%) from an ethyl acetate-hexane (1:4, v/v)-eluted fraction.

NMR (CDCl$_3$) δ: 1.24 (3H, t, J=7 Hz), 1.90-2.05 (2H, m), 2.39 (2H, t, J=7 Hz), 2.91 (2H, t, J=7 Hz), 4.12 (2H, q, J=7. Hz), 7.05-7.15 (2H, m), 7.55-7.65 (2H, m).

EXAMPLE 101

Ethyl 2-chloro-4-(4-fluorophenyl)-5-oxazolebutanoate (3.11 g), 2-methylimidazole (2.46 g), potassium carbonate (4.15 g) and N,N-dimethylformamide (25 ml) was stirred at 120-130° C. for 2 hours. The reaction mixture was poured into water (100 ml) and extracted with ethyl acetate (150 ml×2). The organic layer was dried over anhydrous magnesium sulfate. The organic layer was concentrated, the residue was subjected to silica gel column chromatography, and ethyl 4-(4-fluorophenyl)-2-(2-methyl-1-imidazolyl)-5-oxazolebutanoate was obtained as an oil (3.47 g, 57%) from an ethyl acetate-hexane (1:1, v/v)-eluted fraction. Conversion to the hydrochloride and the subsequent recrystallization from hexane-ethylacetate gave pale yellow prisms. Melting point 140-145° C.

EXAMPLE 102

Ethyl 4-(4-fluorophenyl)-2-(2-methyl-1-imidazolyl)-5-oxazolebutanoate (2.31 g) was dissolved in 20 ml of tetrahydrofuran, to which was added gradually lithium aluminum hydride (269 mg) under ice-cooling. The resulting mixture was stirred for 1 hour. Water (0.5 ml) was carefully added to the reaction mixture. The resulting mixture was filtered, and the residue on the filter paper was washed with ethyl acetate. The filtrate was concentrated to give crystals of 4-(4-fluorophenyl)-2-(2-methyl-1-imidazolyl)-5-oxazolebutanol. Recrystallization from ethyl acetate gave pale yellow prisms (885 mg, 47%). Melting point 97-98° C.

EXAMPLE 103

To a mixture of 2-(2-methyl-1-imidazolyl)-4-(4-trifluoromethylphenyl)-5-oxazolepropanol (700 mg), 2-methylphenol (432 mg), tributylphosphine (607 mg) and tetrahydrofuran (10 ml) was added 1,1'-(azodicarbonyl)dipiperidine (750 mg) at room temperature, and the resulting mixture was stirred for 1 hour. After the reaction mixture was concentrated, the residue was subjected to silica gel column chromatography, and crystals of 2-(2-methyl-1-imidazolyl)-5-[3-(2-methylphenoxy)propyl]-4-(4-trifluoromethylphenyl)oxazole were obtained from an ethyl acetate-hexane (2:3, v/v)-eluted fraction. Recrystallization from acetone-isopropyl ether gave colorless prisms (591 mg, 67%). Melting point 101-102° C.

EXAMPLE 104

To a mixture of 4-(3,4-dichlorophenyl)-2-(2-methyl-1-imidazolyl)-5-oxazolepropanol (352 mg), 2-methylphenol (216 mg), tributylphosphine (405 mg) and tetrahydrofuran (10 ml) was added 1,1'-(azodicarbonyl)dipiperidine (450 mg) at room temperature, and the resulting mixture was stirred for 1 hour. After the reaction mixture was concentrated, the residue was subjected to silica gel column chromatography, and crystals of 4-(3,4-dichlorophenyl)-2-(2-methyl-1-imidazolyl)-5-[3-(2-methylphenoxy)propyl]oxazole were obtained from an ethyl acetate-hexane (2:3, v/v)-eluted fraction. Recrystallization from acetone-isopropyl ether gave colorless prisms (271 mg, 61%). Melting point 116-117° C.

EXAMPLE 105

To a mixture of 4-(4-chlorophenyl)-2-(2-methyl-1-imidazolyl)-5-oxazolepropanol (317 mg), 3-cyanophenol (238 mg), tributylphosphine (405 mg) and tetrahydrofuran (10 ml) was added 1,1'-(azodicarbonyl)dipiperidine (400 mg) at room temperature, and the resulting mixture was stirred for 1 hour. After the reaction mixture was concentrated, the residue was subjected to silica gel column chromatography, and crystals of 4-(4-chlorophenyl)-5-[3-(3-cyanophenoxy)propyl]-2-(2-methyl-1-imidazolyl)oxazole (311 mg, 74%) were obtained from an ethyl acetate-hexane (2:3, v/v)-eluted fraction. Recrystallization from ethyl acetate-isopropyl ether gave colorless prisms (200 mg, 47%). Melting point 78-79° C.

EXAMPLE 106

To a mixture of 4-(4-chlorophenyl)-2-(2-methyl-1-imidazolyl)-5-oxazolepropanol (317 mg), 4-cyano-2-methoxyphenol (300 mg), tributylphosphine (405 mg) and tetrahydrofuran (10 ml) was added 1,1'-(azodicarbonyl)dipiperidine (400 mg) at room temperature, and the resulting mixture was stirred for 1 hour. After the reaction mixture was concentrated, the residue was subjected to silica gel column chromatography, and crystals of 4-(4-chlorophenyl)-5-[3-(4-cyano-2-methoxyphenoxy)propyl]-2-(2-methyl-1-imidazolyl)oxazole (413 mg, 92%) were obtained from an ethyl acetate-hexane (2:3, v/v)-eluted fraction. Recrystallization from ethyl acetate-isopropyl ether gave colorless prisms (313 mg, 70%). Melting point 131-132° C.

EXAMPLE 107

To a mixture of 4-(4-chlorophenyl)-2-(2-methyl-1-imidazolyl)-5-oxazolepropanol (317 mg), 4-fluoro-2-methylphenol (190 mg), tributylphosphine (405 mg) and tetrahydrofuran (10 ml) was added 1,1'-(azodicarbonyl)dipiperidine (400 mg) at room temperature, and the resulting mixture was stirred for 1 hour. After the reaction mixture was concentrated, the residue was subjected to silica gel column chromatography, and crystals of 4-(4-chlorophenyl)-5-[3-(4-fluoro-2-methylphenoxy)propyl]-2-(2-methyl-1-imidazolyl)oxazole (303 mg, 71%) were obtained from an ethyl acetate-hexane (2:3, v/v)-eluted fraction. Recrystallization from ethyl acetate-isopropyl ether gave colorless prisms (202 mg, 47%). Melting point 74-75° C.

EXAMPLE 108

3-[4-(4-Chlorophenyl)-2-(2-methyl-1-imidazolyl)-5-oxazolyl]propyl methanesulfonate (400 mg), diethyl 4-hydroxybenzylphosphonate (365 mg), potassium carbonate (276 mg) and N,N-dimethylformamide (10 ml) was stirred at 100° C. for 4 hours. The reaction mixture was poured into water (100 ml) and extracted with ethyl acetate (100 ml×2). The organic layer was dried over anhydrous magnesium sulfate, and concentrated. The residue was subjected to silica gel column chromatography, and diethyl 4-[3-[4-(4-chlorophenyl)-2-(2-methyl-1-imidazolyl)-5-oxazolyl]propyloxy]benzylphosphonate was obtained as a yellow oil (526 mg, 97%) from an ethyl acetate-eluted fraction.

NMR (CDCl$_3$) δ: 1.24 (6H, t, J=7 Hz), 2.15-2.30 (2H, m), 2.76 (3H, s), 3.09 (2H, d, J=21 Hz), 3.15 (2H, t, J=7 Hz), 3.9-4.1 (6H, m), 6.81 (2H, d, J=8.5 Hz), 7.00 (1H, d, J=1.5 Hz), 7.15-7.25 (2H, m), 7.36 (2H, d, J=8.5 Hz), 7.44 (1H, d, J=1.5 Hz), 7.61 (2H, d, J=8.5 Hz)

EXAMPLE 109

3-[4-(4-Chlorophenyl)-2-(2-methyl-1-imidazolyl)-5-oxazolyl]propyl methanesulfonate (400 mg), 2-chloro-6-methylphenol (285 mg), potassium carbonate (276 mg) and N,N-dimethylformamide (10 ml) was stirred at 100° C. for 1 hour. The reaction mixture was poured into water (100 ml) and extracted with ethyl acetate (100 ml×2). The organic layer was washed with water, dried over anhydrous magnesium sulfate, and concentrated to give crystals of 5-[3-(2-chloro-6-methylphenyl)propyloxy]-4-(4-chlorophenyl)-2-(2-methyl-1-imidazolyl)oxazole (350 mg, 79%). Recrystallization from acetone-isopropyl ether gave pale yellow prisms. Melting point 115-116° C.

EXAMPLE 110

3-[4-(4-Chlorophenyl)-2-(2-methyl-1-imidazolyl)-5-oxazolyl]propyl methanesulfonate (400 mg), 4-hydroxyphenylacetonitrile (200 mg), potassium carbonate (276 mg) and N,N-dimethylformamide (10 ml) was stirred at 100° C. for 4 hours. The reaction mixture was poured into water (100 ml) and extracted with ethyl acetate (100 ml×2). The organic layer was washed with water, dried over anhydrous magnesium sulfate, and concentrated. The residue was subjected to silica gel column chromatography, and 2-[4-[3-[4-(4-chlorophenyl)-2-(2-methyl-1-imidazolyl)-5-oxazolyl]propyloxy]phenyl]acetonitrile was obtained as a yellow oil (380 mg, 89%) from an ethyl acetate-hexane (2:1, v/v)-eluted fraction.

NMR (CDCl$_3$) δ: 2.15-2.30 (2H, m), 2.76 (3H, s), 3.16 (2H, t, J=7 Hz), 4.03 (2H, t, J=6 Hz), 6.83 (2H, d, J=8.5 Hz), 6.99 (1H, d, J=1.5 Hz), 7.22 (2H, d, J=8.5 Hz), 7.34 (2H, d, J=8.5 Hz), 7.42 (1H, d, J=1.5 Hz), 7.60 (2H, d, J=8.5 Hz)

EXAMPLE 111

To a mixture of 4-(4-chlorophenyl)-2-(2-methyl-1-imidazolyl)-5-oxazolepropanol (318 mg), 5,5,8,8-tetramethyl-5,6,7,8-tetrahydro-2-naphthalenol (409 mg), tributylphosphine (405 mg) and tetrahydrofuran (10 ml) was added 1,1'-(azodicarbonyl)dipiperidine (500 mg) at room temperature, and the resulting mixture was stirred for 1 hour. After the reaction mixture was concentrated, the residue was subjected to silica gel column chromatography, and 4-(4-chlorophenyl)-2-(2-methyl-1-imidazolyl)-5-[3-(5,5,8,8-tetramethyl-5,6,7,8-tetrahydro-2-naphthalenyloxy)propyl]oxazole was obtained as a yellow oil (400 mg, 79%) from an ethyl acetate-hexane (1:1, v/v)-eluted fraction.

NMR (CDCl$_3$) δ: 1.26 (12H, s), 1.67 (4H, s), 2.15-2.30 (2H, m), 2.75 (3H, s), 3.15 (2H, t, J=7 Hz), 4.03 (2H, t, J=6 Hz), 6.67 (1H, dd, J=3, 8.5 Hz), 6.80 (1H, d, J=3 Hz), 6.98 (1H, d, J=1.5 Hz), 7.22 (1H, d, J=8.5 Hz), 7.34 (2H, d, J=8.5 Hz), 7.41 (1H, d, J=1.5 Hz), 7.62 (2H, d, J=8.5 Hz)

EXAMPLE 112

To a mixture of 4-(4-chlorophenyl)-2-(2-methyl-1-imidazolyl)-5-oxazolepropanol (4.00 g), (4-hydroxy-3-methylphenyl)acetate (2.96 g), tributylphosphine (3.64 g) and tetrahydrofuran (50 ml) was added gradually 1,1'-(azodicarbonyl) dipiperidine (3.75 g) at room temperature, and the resulting mixture was stirred for 1 hour. After the reaction mixture was concentrated, the residue was subjected to silica gel column chromatography, and crystals of [4-[3-[4-(4-chlorophenyl)-2-(2-methyl-1-imidazolyl)-5-oxazolyl]propyloxy]-3-methylphenyl]acetate (5.00 g, 85%) were obtained from an ethyl acetate-hexane (2:3, v/v)-eluted fraction. Recrystallization from acetone-hexane gave colorless prisms (4.60 g, 78%). Melting point 99-100° C.

EXAMPLE 113

A mixture of [4-[3-[4-(4-chlorophenyl)-2-(2-methyl-1-imidazolyl)-5-oxazolyl]propyloxy]-3-methylphenyl]acetate (4.30 g), 37% hydrochloride (3 ml), and methanol (150 ml) was stirred at room temperature for 1 hour. The reaction mixture was concentrated, which was poured into a 10% aqueous solution of sodium hydrogen carbonate. The precipitated crystals were filtered, washed with pure water and air-dried to give crystals of 4-[3-[4-(4-chlorophenyl)-2-(2-methyl-1-imidazolyl)-5-oxazolyl]propyloxy]-3-methylphenol (3.90 g, 99%). Recrystallization from tetrahydrofuran-hexane gave colorless prisms (2.56 g, 65%). Melting point 175-176° C.

EXAMPLE 114

A mixture of methyl 3-[2-oxo-4-(4-trifluoromethylphenyl)-4-oxazolin-5-yl]propionate (3.90 g), phosphorus oxychloride (11.5 g) and pyridine (0.98 g) was heated to 100-105° C. and stirred for 1 hour. The reaction mixture was added dropwise to heated water (100 ml) of 30° C. and extracted with ethyl acetate (150 ml×2). The organic layer was washed with a saturated aqueous solution of sodium chloride (100 ml), and dried over anhydrous magnesium sulfate. The organic layer was concentrated, the residue was subjected to silica gel column chromatography, and methyl 2-chloro-4-(4-trifluoromethylphenyl)-5-oxazolepropionate was obtained as a yellow oil (2.66 g, 64%) from an ethyl acetate-hexane (1:4, v/v)-eluted fraction.

NMR (CDCl$_3$) δ: 2.77 (2H, t, J=7 Hz), 3.24 (2H, t, J=7 Hz), 3.70 (3H, S), 7.68 (2H, d, J=8.5 Hz), 7.78 (2H, d, J=8.5 Hz)

EXAMPLE 115

A mixture of methyl 3-[4-(3,4-dichlorophenyl)-2-oxo-4-oxazolin-5-yl]propionate (9.0 g), phosphorus oxychloride (26.2 g) and pyridine (2.25 g) was heated to 100-105° C. and stirred for 1 hour. The reaction mixture was added dropwise to heated water (100 ml) of 30° C. and extracted with ethyl acetate (150 ml×2). The organic layer was washed with a saturated aqueous solution of sodium chloride (100 ml), and dried over anhydrous magnesium sulfate. The organic layer was concentrated, the residue was subjected to silica gel column chromatography, and methyl 2-chloro-4-(3,4-dichlorophenyl)-5-oxazolepropionate was obtained as a yellow oil (5.00 g, 52%) from an ethyl acetate-hexane (1:4, v/v)-eluted fraction.

NMR (CDCl$_3$) δ: 2.76 (2H, t, J=7 Hz), 3.20 (2H, t, J=7 Hz), 3.70 (3H, S), 7.49 (2H, d, J=1 Hz), 7.79 (1H, d, J=1 Hz)

EXAMPLE 116

A mixture of methyl 2-chloro-4-(4-trifluoromethylphenyl)-5-oxazolepropionate (1.33 g), 2-methylimidazole (1.33 g), potassium carbonate (2.00 g), and N-methylpyrrolidone (10 ml) was stirred at 110° C. for 2 hours. The reaction mixture was poured into ice water (100 ml). The precipitated crystals were filtered, washed with water and air-dried to give crystals of methyl 2-(2-methyl-1-imidazolyl)-4-(4-trifluoromethylphenyl)-5-oxazolepropionate. Recrystallization from ethyl acetate-hexane gave pale yellow prisms (1.07 g, 71%). Melting point 94-95° C.

EXAMPLE 117

A mixture of methyl 2-chloro-4-(3,4-dichlorophenyl)-5-oxazolepropionate (1.00 g), 2-methylimidazole (0.82 g), potassium carbonate (0.69 g), and N,N-dimethylformamide (20 ml) was stirred at 120° C. for 1 hour. The reaction mixture was poured into ice water (100 ml). The precipitated crystals were filtered, washed in sequence with water and isopropyl ether, and air-dried to give crystals of methyl 4-(3,4-dichlorophenyl)-2-(2-methyl-1-imidazolyl)-5-oxazolepropionate. Recrystallization from ethyl acetate-isopropyl ether gave pale yellow prisms (0.82 g, 72%). Melting point 116-117° C.

EXAMPLE 118

Methyl 2-(2-methyl-1-imidazolyl)-4-(4-trifluoromethylphenyl)-5-oxazolepropionate (1.00 g) was dissolved in toluene (15 ml). To the obtained solution was added dropwise a mixture of a 70% toluene solution (1.20 g) of sodium dihydrobis(2-methoxyethoxy)aluminate, and toluene (5 ml) at 0° C., which was stirred at 0° C. for 30 minutes. To the reaction mixture was carefully added a 10% aqueous solution of (+)-sodium potassium tartrate sesquihydrate (50 ml), which was stirred at room temperature for 1 hour. The precipitated crystals were filtered, washed in sequence with a 10% aqueous solution of (+)-sodium potassium tartrate sesquihydrate, pure water, and isopropyl ether, and air-dried to give crystals of 2-(2-methyl-1-imidazolyl)-4-(4-trifluoromethylphenyl)-5-oxazolepropanol (0.75 g, 81%). Recrystallization from ethyl acetate-isopropyl ether gave pale yellow prisms. Melting point 127-129° C.

EXAMPLE 119

Methyl 4-(3,4-dichlorophenyl)-2-(2-methyl-1-imidazolyl)-5-oxazolepropionate (0.67 g) was dissolved in toluene (5 ml). To the obtained solution was added dropwise a mixture of a 70% toluene solution (0.81 g) of sodium dihydrobis(2-methoxyethoxy)aluminate, and toluene (5 ml) at 0° C., which was stirred at 0° C. for 1 hour. To the reaction mixture was carefully added a 10% aqueous solution of (+)-sodium potassium tartrate sesquihydrate (50 ml), which was stirred at room temperature for 1 hour. The precipitated crystals were filtered, washed in sequence with a 10% aqueous solution of (+)-sodium potassium tartrate sesquihydrate, pure water, and isopropyl ether, and air-dried to give crystals of 4-(3,4-dichlorophenyl)-2-(2-methyl-1-imidazolyl)-5-oxazolepropanol (0.46 g, 74%). Recrystallization from acetone-hexane gave pale yellow prisms. Melting point 140-141° C.

EXAMPLE 120

To a mixture of 4-(4-chlorophenyl)-2-(2-methyl-1-imidazolyl)-5-(3-(2-methylphenoxy)propyl)oxazole (1.0 g) and acetone (10 ml), conc. hydrochloride (0.3 ml) was added, which was allowed to stand at room temperature. The precipitated crystals were filtered (0.97 g). Recrystallization from ethanol gave 4-(4-chlorophenyl)-2-(2-methyl-1-imidazolyl)-5-(3-(2-methylphenoxy)propyl)oxazole hydrochloride.

Elemental analysis (for $C_{23}H_{22}ClN_3O\cdot HCl\cdot\frac{1}{3}H_2O$)
Calculated: C, 61.35; H, 5.30; N, 9.33
Found: C, 61.61; H, 5.24; N, 9.37
NMR (CDCl$_3$) δ: 2.20 (3H, s), 2.25-2.38 (2H, m), 3.17 (3H, s), 3.25 (2H, t, J=7.2 Hz), 4.08 (2T, t, J=5.2 Hz), 6.76 (1H, d, J=8.2 Hz), 6.88 (1H, t, J=7.2 Hz), 7.13 (2H, t, J=7.2 Hz), 7.37-7.43 (3H, m), 7.52-7.61 (3H, m)

EXAMPLE 121

To a mixture of 2-chloro-4-(4-chlorophenyl)-5-oxazolepropanol (40.7 g), 2-methylphenol (21.6 g), tributylphosphine (40.4 g) and tetrahydrofuran (300 ml) was added gradually 1,1'-(azodicarbonyl)dipiperidine (50.4 g) at room temperature, and the resulting mixture was stirred for 1 hour. After the reaction mixture was filtrated, the remaining solid was washed with ethyl acetate. The filtrate and the washings were combined, which was concentrated. The residue was subjected to silica gel column chromatography, and crystals of 2-chloro-4-(4-chlorophenyl)-5-[3-(2-methylphenoxy)]oxazole (38.5 g, 71%) were obtained from an ethyl acetate-hexane (1:6, v/v)-eluted fraction. Recrystallization from ethyl acetate-hexane gave colorless prisms. Melting point 74-75° C.

EXAMPLE 122

A mixture of 2-chloro-4-(4-chlorophenyl)-5-[3-(2-methylphenoxy)propyl]oxazole (30.0 g), 2-methylimidazole (20.6 g), potassium carbonate (34.6 g), and N,N-dimethylformamide (50 ml) was stirred at 125° C. for 1 hour. The reaction mixture was poured into ice water (500 ml). The precipitated crystals were filtered, washed in sequence with water and isopropyl ether, and air-dried to give crude crystals of 4-(4-chlorophenyl)-2-(2-methyl-1-imidazolyl)-5-[3-(2-methylphenoxy)propyl]oxazole (34.5 g).

In the same manner, crude crystals of 4-(4-chlorophenyl)-2-(2-methyl-1-imidazolyl)-5-[3-(2-methylphenoxy)propyl]oxazole (27.0 g) were obtained from 2-chloro-4-(4-chlorophenyl)-5-[3-(2-methylphenoxy)propyl]oxazole (14.0 g). The similar reaction was conducted again to obtain crude crystals of 4-(4-chlorophenyl)-2-(2-methyl-1-imidazolyl)-5-[3-(2-methylphenoxy)propyl]oxazole (17.0 g) from 2-chloro-4-(4-chlorophenyl)-5-[3-(2-methylphenoxy)propyl]oxazole (14.0 g).

The crude crystals of 4-(4-chlorophenyl)-2-(2-methyl-1-imidazolyl)-5-[3-(2-methylphenoxy)propyl]oxazole (total 78.5 g) obtained by these three reactions were subjected to recrystallization three times, once from acetone-hexane, twice from acetone-isopropyl ether to give 4-(4-chlorophenyl)-2-(2-methyl-1-imidazolyl)-5-[3-(2-methylphenoxy)propyl]oxazole as colorless prisms (53.0 g, total yields 66%). Melting point 111-112° C.

The powder X-ray diffraction pattern of the present crystals, which was determined using RINT Ultima+2100 type powder X-ray diffractometer (produced by Rigakudenki) and using as a ray resource Cu-Kα ray (Voltage: 40 KV;

Electric current: 50 mA), is shown in FIG. 1.

Data of powder X-ray diffraction (main peaks)

| Angle of diffraction: 2θ(°) | Spacing: d value (angstrom) |
|---|---|
| 12.3 | 7.21 |
| 13.4 | 6.62 |
| 18.0 | 4.93 |
| 21.2 | 4.18 |
| 25.8 | 3.45 |
| 26.5 | 3.36 |

REFERENCE EXAMPLE 1

To a mixture of 2-chlorothiophene (36.0 g) and adipic acid monoethyl ester chloride (36.9 g) was added gradually aluminum chloride (50.8 g) with stirring under ice-cooling, and the resulting mixture was stirred at room temperature for 2 hours. The reaction mixture was poured into ice water (1 L) and extracted with diethyl ether (200 ml×2). The organic layer was washed with a 10% aqueous solution of sodium hydrogen carbonate (200 ml), dried over anhydrous magnesium sulfate, and concentrated to give ethyl 6-(5-chloro-2-thienyl)-6-oxohexanoate as an oil (52.5 g, quantitative).

NMR (CDCl$_3$) δ: 1.26 (3H, t, J=7 Hz), 1.60-1.90 (4H, m), 2.55-2.80 (2H, m), 2.80-2.90 (2H, m), 4.13 (2H, q, J=7 Hz), 6.96 (1H, d, J=4 Hz), 7.49 (1H, d, J=4 Hz).

REFERENCE EXAMPLE 2

Ethyl 6-(5-chloro-2-thienyl)-6-oxohexanoate (50.0 g) was dissolved in methylene chloride (150 ml), to which was added dropwise bromine (24.5 g) with stirring at room temperature. The mixture was stirred at room temperature for 1 hour, a 10% aqueous solution of sodium sulfite was then carefully added until disappearance of the red color of bromine, which was extracted with diethyl ether (200 ml×2). The organic layer was washed with a 10% aqueous solution of sodium hydrogen carbonate (100 ml), dried over anhydrous magnesium sulfate, and concentrated to give ethyl 5-bromo-6-(5-chloro-2-thienyl)-6-oxohexanoate as an oil (64.4 g, >99%).

NMR (CDCl$_3$) δ: 1.25 (3H, t, J=7 Hz), 1.55-2.00 (4H, m), 2.00-2.30 (2H, m), 2.39 (2H, t, J=7 Hz), 4.13 (2H, q, J=7 Hz), 4.90 (1H, dd, J=6/8 Hz), 6.99 (1H, d, J=4 Hz), 7.62 (1H, d, J=4 Hz).

REFERENCE EXAMPLE 3

A mixture of ethyl 5-bromo-6-(5-chloro-2-thienyl)-6-oxohexanoate (64.4 g), sodium formate (60.0 g) and methanol (150 ml) was stirred with heating under reflux for 16 hours. The reaction mixture was diluted with ethyl acetate (500 ml) and washed with water (200 ml×2). The organic layer was dried over anhydrous magnesium sulfate and concentrated. The residue was subjected to silica gel column chromatography, and ethyl 6-(5-chloro-2-thienyl)-5-hydroxy-6-oxohexanoate was obtained as a yellow oil (21.6 g, 41%) from an ethyl acetate-hexane (1:4, v/v)-eluted fraction.

NMR (CDCl$_3$) δ: 1.24 (3H, t, J=7 Hz), 1.55-2.05 (4H, m), 2.37 (2H, t, J=7 Hz), 3.48 (1H, d, J=6 Hz), 4.12 (2H, q, J=7 Hz), 4.81 (1H, bs), 7.01 (1H, d, J=4 Hz), 7.59 (1H, d, J=4 Hz).

REFERENCE EXAMPLE 4

To a mixture of ethyl 6-(5-chloro-2-thienyl)-5-hydroxy-6-oxohexanoate (21.6 g), pyridine (6.4 g) and tetrahydrofuran (100 ml) was added dropwise phenyl chlorocarbonate (12.7 g) with stirring under ice-cooling. After the resulting mixture was stirred at room temperature for 16 hours, the reaction mixture was concentrated, diluted with ethyl acetate (400 ml) and washed with water (200 ml). The organic layer was dried over anhydrous magnesium sulfate, and concentrated to give ethyl 6-(5-chloro-2-thienyl)-6-oxo-5-phenoxycarbonyloxy-hexanoate as a yellow oil (30.5 g, quantitative).

NMR(CDCl$_3$) δ: 1.25 (3H, t, J=7 Hz), 1.85-2.00 (4H, m), 2.00-2.15 (2H, m), 4.15 (2H, q, J=7.0 Hz), 5.56 (1H, t, J=6 Hz), 7.00 (1H, d, J=4 Hz), 7.15-7.45 (5H, m), 7.70 (1 h, d, J=4 Hz).

REFERENCE EXAMPLE 5

A mixture of ethyl 6-(5-chloro-2-thienyl)-6-oxo-5-phenoxycarbonyloxyhexanoate (30.5 g), ammonium acetate (28.6 g) and acetic acid (100 ml) was stirred with heating under reflux for 2 hours. The reaction mixture was poured into 500 ml of water, and the resulting solid precipitate was collected, washed with water and isopropyl ether and air-dried to give crystals of ethyl 4-[4-(5-chloro-2-thienyl)-2-oxo-4-oxazolin-5-yl]butanoate (13.6 g, 58%). Recrystallization from acetone-isopropyl ether gave pale yellow prisms. Melting point 95-96° C.

REFERENCE EXAMPLE 6

To a mixture of fluorobenzene (37.3 g) and adipic acid monoethyl ester chloride (18.0 g) was added gradually aluminum chloride (26.6 g) with stirring under ice-cooling, and the resulting mixture was stirred at room temperature for 2 hours. The reaction mixture was poured into ice water (500 ml) and extracted with diethyl ether (200 ml×2). The organic layer was washed with a 10% aqueous solution of sodium hydrogen carbonate (200 ml), dried over anhydrous magnesium sulfate, and concentrated to give ethyl 6-(4-fluorophenyl)-6-oxohexanoate as an oil (14.1 g, 57%).

NMR (CDCl$_3$) δ: 1.25 (3H, t, J=7 Hz), 1.6-1.9 (4H, m), 2.30-2.40 (2H, m), 2.90-3.00 (2H, m), 4.13 (2H, q, J=7 Hz), 7.05-7.15 (1H, m), 8.00-8.10 (1H, m).

REFERENCE EXAMPLE 7

Ethyl 6-(4-fluorophenyl)-6-oxohexanoate (14.0 g) was dissolved in methylene chloride (100 ml), and bromine (8.87 g) was added dropwise with stirring at room temperature. After an hour of stirring at room temperature, a 10% aqueous solution of sodium sulfite was carefully added until disappearance of the red color of bromine, and the mixture was then extracted with diethyl ether (100 ml×2). The organic layer was washed with a 10% aqueous solution of sodium hydrogen carbonate (100 ml), dried over anhydrous magnesium sulfate, and concentrated to give ethyl 5-bromo-6-(4-fluorophenyl)-6-oxohexanoate as an oil (17.6 g, quantitative).

NMR (CDCl$_3$) δ: 1.25 (3H, t, J=7 Hz), 1.6-1.9 (2H, m), 2.15-2.30 (2H, m), 2.40 (2H, t, J=7 Hz), 4.13 (2H, q, J=7 Hz), 5.09 (1H, dd, J=6/8 Hz), 7.05-7.15 (2H, m), 8.0-8.1 (2H, m).

REFERENCE EXAMPLE 8

A mixture of ethyl 5-bromo-6-(4-fluorophenyl)-6-oxohexanoate (17.6 g), sodium formate (16.9 g) and methanol (150 ml) was stirred with heating under reflux for 16 hours. The reaction mixture was diluted with ethyl acetate (500 ml), and washed with water (200 ml×2). The organic layer was dried over anhydrous magnesium sulfate and then concentrated, the residue was subjected to silica gel column chromatography, and ethyl 6-(4-fluorophenyl)-5-hydroxy-6-oxohexanoate was obtained as a yellow oil (13.8 g, 96%) from an ethyl acetate-hexane (1:4, v/v)-eluted fraction.

NMR (CDCl$_3$) δ: 1.23 (3H, t, J=7 Hz), 1.5-2.0 (4H, m), 2.30-2.45 (2H, m), 3.64 (1H, ns), 4.13 (2H, q, J=7 Hz), 5.05 (1H, dd, J=3/8 Hz), 7.0-7.2 (2H, m), 7.9-8.1 (2H, m).

REFERENCE EXAMPLE 9

To a mixture of ethyl 6-(4-fluorophenyl)-5-hydroxy-6-oxohexanoate (13.5 g), pyridine (4.40 g) and tetrahydrofuran (100 ml) was added dropwise phenyl chlorocarbonate (8.67 g) with stirring under ice-cooling. The mixture was stirred at room temperature for 16 hours. This reaction mixture was concentrated, diluted with ethyl acetate (400 ml) and washed with water (200 ml). The organic layer was dried over anhydrous magnesium sulfate, and concentrated to give ethyl 6-(4-fluorophenyl)-6-oxo-5-phenoxycarbonyloxyhexanoate as a yellow oil (18.1 g, 93%).

NMR (CDCl$_3$) δ: 1.24 (3H, t, J=7 Hz), 1.8-2.0 (4H, m), 2.30-2.45 (2H, m), 4.12 (2H, q, J=7.0 Hz), 5.82 (1H, dd, J=5/8 Hz), 7.1-7.4 (7H, m), 7.9-8.1 (2H, m)

REFERENCE EXAMPLE 10

A mixture of ethyl 6-(4-fluorophenyl)-6-oxo-5-phenoxycarbonyloxyhexanoate (18.0 g), ammonium acetate (17.8 g) and acetic acid (100 ml) was stirred with heating under reflux for 2 hours. The reaction mixture was poured into water (500 ml) and extracted with ethyl acetate (200 ml×2), and the extract was washed with water (200 ml). The organic layer was dried over anhydrous magnesium sulfate and concentrated. The residue was subjected to silica gel column chromatography, and ethyl 4-[4-(4-fluorophenyl)-2-oxo-4-oxazolin-5-yl]butanoate was obtained as an oil (7.67 g, 56%) from an ethyl acetate-hexane (1:1, v/v)-eluted fraction.

NMR (CDCl$_3$) δ: 1.23 (3H, t, J=7 Hz), 1.9-2.1 (2H, m), 2.35-2.45 (2H, m), 2.70 (2H, t, J=7 Hz), 4.11 (2H, q, J=7.0 Hz), 7.1-7.2 (2H, m), 7.35-7.45 (2H, m), 10.30 (1H, bs)

REFERENCE EXAMPLE 11

To a mixture of 1-fluoronaphthalene (20.0 g) and adipic acid monoethyl ester chloride (27.5 g) was added gradually aluminum chloride (38.5 g) with stirring under ice-cooling, and the resulting mixture was stirred at room temperature for 2 hours. The reaction mixture was poured into ice water (500 ml) and extracted with diethyl ether (200 ml×2). The organic layer was washed with a 10% aqueous solution of sodium hydrogen carbonate (200 ml), dried over anhydrous magnesium sulfate, and concentrated to give ethyl 6-(4-fluoro-1-naphthyl)-6-oxohexanoate as an oil (27.7 g, 67%).

NMR (CDCl$_3$) δ: 1.25 (3H, t, J=7 Hz), 1.6-2.0 (4H, m), 2.37 (2H, t, J=7 Hz), 3.07 (2H, t, J=7 Hz), 4.13 (2H, q, J=7 Hz), 7.15 (1H, dd, J=8/10 Hz), 7.55-7.65 (2H, m), 7.89 (1H, dd, J=5/8 Hz), 8.1-8.2 (2H, m), 8.5-8.6 (1H, m).

REFERENCE EXAMPLE 12

Ethyl 6-(4-fluoro-1-naphthyl)-6-oxohexanoate (27.7 g) was dissolved in methylene chloride (100 ml), and bromine (14.6 g) was added dropwise with stirring at room temperature. After an hour of stirring at room temperature, a 10% aqueous solution of sodium sulfite was carefully added until disappearance of the red color of bromine, which was extracted with diethyl ether (300 ml×2). The organic layer was washed with a 10% aqueous solution of sodium hydrogen carbonate (100 ml), dried over anhydrous magnesium sulfate, and concentrated to give ethyl 5-bromo-6-(4-fluoro-1-naphthyl)-6-oxohexanoate as an oil (34.9 g, quantitative).

NMR (CDCl$_3$) δ: 1.26 (3H, t, J=7 Hz), 1.6-2.0 (4H, m), 2.42 (2H, t, J=7 Hz), 4.15 (2H, q, J=7 Hz), 5.21 (1H, dd, J=6/8 Hz), 7.15 (1H, dd, J=8/10 Hz), 7.60-7.80 (2H, m), 7.92 (1H, dd, J=5/8 Hz), 8.1-8.2 (1H, m), 8.5-8.6 (1H, m)

REFERENCE EXAMPLE 13

A mixture of ethyl 5-bromo-6-(4-fluoro-1-naphthyl)-6-oxohexanoate (34.3 g), sodium formate (34.0 g) and methanol (150 ml) was stirred with heating under reflux for 16 hours. The reaction mixture was diluted with ethyl acetate (500 ml) and washed with water (200 ml×2). The organic layer was dried over anhydrous magnesium sulfate and concentrated. The residue was subjected to silica gel column chromatography, and ethyl 6-(4-fluoro-1-naphthyl)-5-hydroxy-6-oxohexanoate was obtained as a yellow oil (19.0 g, 65%) from an ethyl acetate-hexane (1:4, v/v)-eluted fraction.

NMR (CDCl$_3$) δ: 1.13 (3H, t, J=7 Hz), 1.5-2.0 (4H, m), 2.15-2.30 (2H, m), 3.89 (1H, d, J=6 Hz), 4.00 (2H, q, J=7 Hz), 7.20 (1H, dd, J=8/10 Hz), 7.6-7.8 (2H, m), 7.83 (1H, dd, J=5/8 Hz), 8.1-8.2 (1H, m), 8.5-8.6 (1H, m)

REFERENCE EXAMPLE 14

To a mixture of ethyl 6-(4-fluoro-1-naphthyl)-5-hydroxy-6-oxohexanoate (19.0 g), pyridine (5.50 g) and tetrahydrofuran (100 ml) was added dropwise phenyl chlorocarbonate (10.8 g) with stirring under ice-cooling. After 16 hours of stirring at room temperature, the reaction mixture was concentrated, diluted with ethyl acetate (400 ml) and washed with water (200 ml). The organic layer was dried over anhydrous magnesium sulfate, and concentrated to give ethyl 6-(4-fluoro-1-naphthyl)-6-oxo-5-phenoxycarbonyloxyhexanoate as a yellow oil (26.3 g, 96%).

NMR (CDCl$_3$) δ: 1.18 (3H, t, J=7 Hz), 1.8-2.0 (4H, m), 2.25-2.35 (2H, m), 4.07 (2H, q, J=7.0 Hz), 5.86 (1H, t, J=6 Hz), 7.25-7.35 (4H, m), 7.35-7.45 (2H, m), 7.60-7.70 (2H, m), 7.98 (1H, dd, J=5/8 Hz), 8.15-8.20 (1H, m), 8.50-8.55 (1H, m)

REFERENCE EXAMPLE 15

A mixture of ethyl 6-(4-fluoro-1-naphthyl)-6-oxo-5-phenoxycarbonyloxyhexanoate (18.0 g), ammonium acetate (17.8 g) and acetic acid (100 ml) was stirred with heating under reflux for 2 hours. The reaction mixture was poured into water (500 ml) and extracted with ethyl acetate (200 ml×2), and the extract was washed with water (200 ml). The organic layer was dried over anhydrous magnesium sulfate and concentrated. The residue was subjected to silica gel column chromatography, and crystals of ethyl 4-[4-(4-fluoro-1-naphthyl)-2-oxo-4-oxazolin-5-yl]butanoate (3.64 g, 18%) were obtained from an ethyl acetate-hexane (2:3, v/v)-eluted fraction. Recrystallization from hexane-ethyl acetate gave pale yellow prisms. Melting point 70-73° C. Crystals of ethyl 5-[4-(4-fluoro-1-naphthyl)-2-oxo-4-oxazolin-4-yl]butanoate (4.09 g, 18%) were obtained from an ethyl acetate-hexane (3:2, v/v)-eluted fraction. Recrystallization from hexane-ethyl acetate gave pale yellow prisms. Melting point 77-79° C.

REFERENCE EXAMPLE 16

A mixture of ethyl 4-[5-(4-fluoro-1-naphthyl)-2-oxo-4-oxazolin-4-yl]butanoate (3.09 g), phosphorus oxychloride (6.00 g) and pyridine (0.80 g) was heated to 120-130° C. and stirred for 45 minutes. The reaction mixture was poured into 100 ml of ice water and extracted with ethyl acetate (100 ml×2). The organic layer was washed in sequence with a 10% aqueous solution of sodium hydrogen carbonate (50 ml) and a saturated aqueous solution of sodium chloride (50 ml), and dried over anhydrous magnesium sulfate. The organic layer was concentrated, the residue was subjected to silica gel column chromatography, and ethyl 2-chloro-5-(4-fluoro-1-naphthyl)-4-oxazolebutanoate was obtained as a yellow oil (903 mg, 28%) from an ethyl acetate-hexane (1:4, v/v)-eluted fraction.

NMR (CDCl$_3$) δ: 1.13 (3H, t, J=7 Hz), 1.9-2.05 (2H, m), 2.29 (2H, t, J=7 Hz), 2.55 (2H, t, J=7 Hz), 3.99 (2H, q, J=7. Hz), 7.21 (1H, dd, J=6/8 Hz), 7.47 (1H, dd, J=6/8 Hz), 7.6-7.7 (2H, m), 7.8-7.9 (1H, m), 8.1-8.2 (1H, m).

REFERENCE EXAMPLE 17

A mixture of ethyl 2-chloro-5-(4-fluoro-1-naphthyl)-4-oxazolebutanoate (700 mg), 2-methylimidazole (821 mg), potassium carbonate (1.38 g) and N,N-dimethylformamide (10 ml) was stirred at 120-130° C. for 2 hours. The reaction mixture was poured into water (100 ml) and extracted with ethyl acetate (150 ml×2). The organic layer was dried over anhydrous magnesium sulfate and concentrated. The residue was subjected to silica gel column chromatography, and ethyl 5-(4-fluoro-1-naphthyl)-2-(2-methyl-1-imidazolyl)-4-oxazolebutanoate was obtained as an oil (675 mg, 77%) from an ethyl acetate-hexane (1:1, v/v)-eluted fraction.

NMR (CDCl$_3$) δ: 1.16 (3H, t, J=7 Hz), 1.95-2.1 (2H, m), 2.32 (2H, t, J=7 Hz), 2.78 (3H, s), 2.80 (2H, t, J=7 Hz), 4.02 (2H, q, J=7. Hz), 7.00 (1H, d, J=2 Hz), 7.20 (1H, dd, J=8/10 Hz), 7.44 (1H, dd, J=6/8 Hz), 7.54 (1H, d, J=2 Hz), 7.55-7.65 (2H, m), 8.0-8.1 (1H, m), 8.15-8.2 (1H, m)

REFERENCE EXAMPLE 18

Ethyl 5-(4-fluoro-1-naphthyl)-2-(2-methyl-1-imidazolyl)-4-oxazolebutanoate (401 mg) was dissolved in 10 ml of tetrahydrofuran, to which was added gradually lithium aluminum hydride (50 mg) under ice-cooling, and the mixture was stirred for 1 hour. Water (0.1 ml) was carefully added to the reaction mixture, which was filtered. The residue on the filter paper was washed with ethyl acetate. The filtrate was concentrated to give crystals of 5-(4-fluoro-1-naphthyl)-2-(2-methyl-1-imidazolyl)-4-oxazolebutanol. Recrystallization from acetone-diethyl ether gave colorless prisms (294 mg, 82%). Melting point 107-109° C.

REFERENCE EXAMPLE 19

A mixture of 2-bromo-4'-trifluoromethyl acetophenone (40.0 g), sodium formate (40.0 g) and methanol (200 ml) was stirred with heating under reflux for 6 hours. The reaction mixture was concentrated and poured into water (500 ml). The precipitated crystals were filtered, washed with water, and air-dried to give crystals of 2-hydroxy-4'-trifluoromethyl acetophenone (24.5 g, 80%). Melting point 112-114° C.

REFERENCE EXAMPLE 20

To a mixture of 2-hydroxy-4'-trifluoromethyl acetophenone (24.0 g), pyridine (10.3 g) and tetrahydrofuran (200 ml) was added dropwise phenyl chlorocarbonate (20.4 g) under ice-cooling, which was stirred at room temperature for 1 hour. The reaction mixture was concentrated, which was poured into water (500 ml), and extracted with ethyl acetate (150 ml×2). The organic layer was washed with water and then a saturated aqueous solution of sodium chloride, which was dried over anhydrous magnesium sulfate and concentrated. The residue was subjected to crystallization by addition of isopropyl ether (100 ml) to give crystals of 2-oxo-2-(4-trifluoromethylphenyl)ethyl phenyl carbonate (18.9 g, 53%). Melting point 134-135° C.

REFERENCE EXAMPLE 21

A mixture of 2-oxo-2-(4-trifluoromethylphenyl)ethyl phenyl carbonate (18.0 g), ammonium acetate (20 g) and acetic acid (100 ml) was stirred with heating under reflux for 1 hour. The reaction mixture was concentrated, and poured into ice water (200 ml). The solid precipitates were filtered, washed with water, and air-dried to give crystals of 4-(4-trifluoromethylphenyl)-2-oxazolone (10.8 g, 85%). Melting point decomposed at 250° C. or more.

REFERENCE EXAMPLE 22

A mixture of 4-(4-trifluoromethylphenyl)-2-oxazolone (10.8 g), methyl acrylate (8.10 g), boron trifluoride diethyl ether complex (6.86 g) and toluene (50 ml) was stirred with heating under reflux for 3 hours. The reaction mixture was concentrated, and poured into ice water (200 ml). The solid precipitates were filtered, washed with water, and air-dried. Recrystallization from isopropyl alcohol-isopropyl ether gave methyl 3-[2-oxo-4-(4-trifluoromethylphenyl)-4-oxazolin-5-yl]propionate as pale yellow prisms (4.00 g, 27%). Melting point 156-157° C.

REFERENCE EXAMPLE 23

A mixture of 2-bromo-3',4'-dichloroacetophenone (78.0 g), sodium formate (68.0 g) and methanol (300 ml) was stirred with heating under reflux for 16 hours. The reaction mixture was concentrated and poured into water (1 L). The solid precipitates were filtered, washed with water and then isopropyl ether, and air-dried. The residue was dried under reduced pressure to give crystals of 2-hydroxy-3',4'-dichloroacetophenone (25.0 g, 42%). Recrystallization from ethyl acetate-hexane gave pale yellow prisms. Melting point 115-118° C.

REFERENCE EXAMPLE 24

A mixture of 2-hydroxy-3',4'-dichloroacetophenone (10.3 g), potassium cyanide (8.1 g) and 2-propanol (100 ml) was heated to 50° C., to which was added dropwise acetic acid (6.0 g) gradually and stirred at 50° C. for 2 hours. The reaction mixture was concentrated and poured into ice water (200 ml). The solid precipitates were filtered, washed with water, and air-dried to give crystals of 4-(3',4'-dichlorophenyl)-2-oxazolone (6.0 g, 52%). Recrystallization from tetrahydrofuran-hexane gave pale yellow prisms. Melting point 262-263° C.

REFERENCE EXAMPLE 25

A mixture of 4-(3',4'-dichlorophenyl)-2-oxazolone (8.9 g), methyl acrylate (13.2 g), boron trifluoride diethyl ether complex (8.5 g) and toluene (100 ml) was stirred with heating under reflux for 12 hours. The reaction mixture was concentrated, and poured into ice water (500 ml). The solid precipitates were filtered, washed with water, and air-dried to give crystals of methyl 3-[2-oxo-4-(3',4'-dichlorophenyl)-4-oxazolin-5-yl]propionate (9.0 g, 75%). Recrystallization from ethyl acetate-hexane gave pale yellow prisms. Melting point 129-130° C.

INDUSTRIAL APPLICABILITY

The preparation of the invention has neurotrophin production/secretion promoting activity and low toxicity and can be used, for example as a prophylactic/therapeutic agent for peripheral neuropathy (e.g. diabetic neuropathy, cancer therapy-induced neuropathy), a prophylactic/therapeutic agent for diabetic cardiomyopathy, a prophylactic/therapeutic agent for peripheral nerve injury, a prophylactic/therapeutic agent for spinal injury, a prophylactic/therapeutic agent for amyotrophic lateral sclerosis (ALS), a prophylactic/therapeutic agent for multiple sclerosis, a prophylactic/therapeutic agent for cerebral ischemic diseases, a prophylactic/therapeutic agent for senile dementia of Alzheimer type, a prophylactic/therapeutic agent for Parkinson's disease or Huntington's chorea, a prophylactic/therapeutic agent for depression, a prophylactic/therapeutic agent for inflammatory bowel disease, an ameliorating agent for chronic pain, an ameliorating agent for peripheral neuropathy, or an ameliorating agent for cerebral metabolic disorder.

The invention claimed is:

1. A method for treating senile dementia of Alzheimer's disease in a mammal in need thereof, which comprises administering to said mammal an effective amount of an azole derivative of the formula:

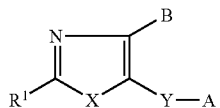

wherein $R^1$ represents an imidazolyl group which may optionally be substituted; A represents (i) a phenoxy group substituted with an alkyl group which may optionally be substituted or (ii) a phenoxy group substituted with a $C_{1-4}$ alkoxy; B represents a phenyl group which may optionally be substituted; X represents oxygen atom; and Y represents a divalent hydrocarbon group, or a salt thereof.

2. A method according to claim 1, wherein A is a phenoxy group substituted with an alkyl group which may optionally be substituted.

3. A method according to claim 1, wherein Y is a divalent aliphatic hydrocarbon group.

4. A method according to claim 1, wherein the azole derivative is 4-(4-chlorophenyl)-5-[3-(2-methoxyphenoxy)propyl]-2-(2-methyl-1-imidazolyl)oxazole, 4-(4-chlorophenyl)-5-[3-(3-methoxyphenoxy)propyl]-2-(2-methyl-1-imidazolyl)oxazole, 4-(4-chlorophenyl)-5-[3-(4-methoxyphenoxy)propyl]-2-(2-methyl-1-imidazolyl) oxazole, or 4-(4-chlorophenyl)-2-(2-methyl-1-imidazolyl)-5-[3-(2-methylphenoxy)propyl]oxazole.

5. A method according to claim 1, wherein the azole derivative is of the formula:

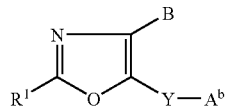

wherein $R^1$ represents an imidazolyl group which may optionally be substituted; $A^b$ represents an phenoxy group which is substituted by an alkyl group; B represents a phenyl group which may optionally be substituted; and Y represents a divalent hydrocarbon group, or a salt thereof.

6. A method according to claim 5, wherein $R^1$ is an imidazolyl group which may optionally be substituted by a $C_{1-10}$ alkyl.

7. A method according to claim 5, wherein B is a phenyl group which may optionally be substituted by halogens.

8. A method according to claim 5, wherein Y is a divalent aliphatic hydrocarbon group.

9. A method according to claim 8, wherein Y is a divalent $C_{1-4}$ aliphatic hydrocarbon group.

10. A method according to claim 5, wherein the azole derivative is 4-(4-Chlorophenyl)-2-(2-methyl-1-imidazolyl)-5-[3-(2-methylphenoxy)propyl]oxazole or a salt thereof.

11. A method according to claim 5, wherein the azole derivative is 4-(4-Chlorophenyl)-2-(2-methyl-1-imidazolyl)-5-[3-(3-methylphenoxy)propyl]oxazole or a salt thereof.

* * * * *